(12) United States Patent
Kubota et al.

(10) Patent No.: US 7,186,701 B2
(45) Date of Patent: Mar. 6, 2007

(54) DEHYDRATING AGENT AND METHOD FOR DEHYDRATING MOIST ARTICLE USING THE AGENT AND DEHYDRATED ARTICLE OBTAINED BY THE METHOD

(75) Inventors: Michio Kubota, Okayama (JP); Tomoyuki Nishimoto, Okayama (JP); Hajime Aga, Okayama (JP); Shigeharu Fukuda, Okayama (JP); Toshio Miyake, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 649 days.

(21) Appl. No.: 10/466,438

(22) PCT Filed: Jan. 17, 2002

(86) PCT No.: PCT/JP02/00288

§ 371 (c)(1),
(2), (4) Date: Jul. 16, 2003

(87) PCT Pub. No.: WO02/057011

PCT Pub. Date: Jul. 25, 2002

(65) Prior Publication Data

US 2006/0008791 A1 Jan. 12, 2006

(30) Foreign Application Priority Data

Jan. 19, 2001 (JP) ............................. 2001-010991

(51) Int. Cl.
*A61K 31/702* (2006.01)
*C08B 37/00* (2006.01)

(52) U.S. Cl. .................. 514/54; 536/1.11; 536/4.1; 536/123.1; 502/400; 502/402

(58) Field of Classification Search ................ 502/400, 502/402; 514/54; 536/1.11, 4.1, 123.1
See application file for complete search history.

(56) References Cited

U.S. PATENT DOCUMENTS

| 4,788,237 A | 11/1988 | Le-Khac |
| 4,810,827 A | 3/1989 | Mitsuhashi et al. |
| 4,812,444 A | 3/1989 | Mitsuhashi et al. |
| 5,026,566 A | 6/1991 | Roser |
| 5,175,279 A | 12/1992 | Kurane et al. |
| 5,889,179 A | 3/1999 | Cote et al. |

FOREIGN PATENT DOCUMENTS

| EP | 00600730 | * | 6/1994 |
| EP | 0600730 A1 | | 6/1994 |
| EP | 1229112 A1 | | 8/2002 |
| EP | 1284286 A1 | | 2/2003 |
| GB | 2173400 | | 10/1986 |
| WO | WO-01/090338 | | 5/2001 |
| WO | WO-02/010361 | | 7/2001 |

OTHER PUBLICATIONS

Cote, G. et al Eur. J. Biochem., 1994, 226, 631-648.*
Goodman and Gilman's "The Pharmacological Basis of Therapeutics", 10th Ed., 1996, p. 54.*
Database WPI; Section Ch, Week 198701; Derwent Publications Ltd., XP002270691; JP 61 265063; 1986.
Database WPI; Section Ch, Week 198137; Derwent Publications Ltd., XP002270692; JP 61 265063; 1981.
Database WPI; Section Ch, Week 199428; Derwent Publications Ltd., XP002270693; JP 06 165700; 1984.
Akira, Yoshino; Abstract of JP 8134447; "Gelatinous Watering Material"; 1996.
Cote, Gregory L. et al "Enzymically produced cyclic α-1,3-linked and α-1,6-linked oligosaccharides of D-glucose" European Journal o fBiochemistry, (1994) vol. 226, pp. 631-648.
Journal of Japanese Society of Nutrition and food Science, vol. 43, No. 1, pp. 23-29, (1990) considered english abstract.
Kazuya Yamamoto, et al "Purification and Some Properties of Dextrin Dextranase from Acetobacter capsulatus ATCC 11894" Bioscience Biotechnology and Biochemistry, vol. 56, pp. 169-173, (1992).
Tsuneyuki Oku, et al "Metabolic Fate of Ingested [$^{14}$C]-Maltitol in Man" Journal of Nutritional Science and Vitaminology, vol. 37, pp. 529-544 (1991).

* cited by examiner

*Primary Examiner*—Shaojia Anna Jiang
*Assistant Examiner*—Ganapathy Krishnan
(74) *Attorney, Agent, or Firm*—Browdy and Neimark, PLLC

(57) ABSTRACT

The present invention has the object to dehydrate hydrous matters without denaturing or deteriorating them by using a dehydrating agent comprising an anhydrous cyclotetrasaccharide, and provides a dehydrating agent comprising the cyclotetrasaccharide; a method for dehydrating hydrous matters through a step of incorporating, contacting or coexisting the cyclotetrasaccharide into, with, or in the hydrous matters; and dehydrated products obtainable thereby.

2 Claims, 33 Drawing Sheets

DEHYDRATING AGENT AND METHOD FOR DEHYDRATING MOIST ARTICLE USING THE AGENT AND DEHYDRATED ARTICLE OBTAINED BY THE METHOD

TECHNICAL FIELD

The present invention relates to a dehydrating agent comprising, as an effective ingredient, a saccharide having the structure of cyclo{→6)-α-D-glucopyranosyl-(1→3)-α-D-glucopyranosyl-(1→6)-α-D-glucopyranosyl-(1→3)-α-D-glucopyranosyl-(1} (referred to as "cyclotetrasaccharide" based on the structure, throughout the specification hereinafter); a method for dehydrating hydrous matters using the same; and dehydrated products prepared by the method.

BACKGROUND ART

As disclosed in Japanese Patent Kokai Nos. 136,240/87, 152,536/87, 152,537/87, 170,221/94, etc., by the present inventors, methods for dehydrating hydrous matters using saccharides are those which exert dehydrating powers of anhydrous saccharides by allowing them to entrap moisture and to be converted into their hydrous crystalline forms. Unlike heat drying, these methods do not require severe conditions and have features that they convert hydrous matters into dehydrated products without denaturing or deteriorating them.

However, it was revealed that, among the above methods, the one disclosed in Japanese Patent Kokai No. 152,536/87, where anhydrous aldohexoses such as anhydrous glucose and anhydrous galactose are used, has poor preservation stability of dehydrated products because, in spite of their relatively high dehydration powers, the saccharides are highly reactive or easily react with amino acids, peptides, etc., and cause browning reaction. It was also found that such anhydrous aldohexoses are not converted into any hydrous form even under a relatively high humid condition and have only a poor dehydrating power. As for the methods using anhydrous maltose and palatinose, which are respectively disclosed in Japanese Patent Kokai Nos. 136,240/87 and 152,537/87, it was found that there still remains anxiety about stability of dehydrated products when preserved for a relatively long period of time, because of their inherent reducibilities, though they are relatively low. In addition, these methods have the demerit that they require a relatively large amount of anhydrous maltose or palatinose as a dehydrating agent because these saccharides have only a relatively-low-moisture-entrapping power as low as about 5% (w/w) to each of their weights.

Since the non-reducing anhydrous glycosyl fructosides such as anhydrous raffinose, anhydrous erlose, and anhydrous melezitose, which are disclosed in Japanese Patent Kokai No. 152,537/87, have no reducing power, these saccharides would be neither react with amino acids and peptides nor cause browning reaction, and they also have advantageous stability for a relatively long period of time. The above saccharides, however, have an intramolecular fructoside bond poor in acid tolerance, speculating that they should not necessarily be appropriately used as dehydrating agents for acid hydrous matters. Accordingly, there still remains anxiety about the stability of dehydrated products produced thereby. While anhydrous α,α-trehalose, disclosed in Japanese Patent Kokai No. 170,221/94, has no reducing power and satisfactory stabilizes dehydrated products for a relatively long period of time. Due to an activity of entrapping a relatively large amount of moisture as high as about 10% (w/w), α,α-trehalose would be more suitably used than the above-mentioned other saccharide. The method, however, still needs a relatively large amount of anhydrous α,α-trehalose for dehydration, and therefore another dehydrating agent having a higher moisture and/or drying efficiency have been in great demand.

DISCLOSURE OF INVENTION

To overcome the demerits in conventional dehydration methods using saccharides, the present inventors have screened natural non-reducing saccharides in an anhydrous form and energetically studied to establish an improved dehydrating agent and uses thereof.

The present inventors previously established a method for producing cyclotetrasaccharide, which had been known to be only prepared in a laboratory demonstration, at a lesser cost and on an industrial scale from material amylaceous saccharides. They also revealed that cyclotetrasaccharide exists at least in the form of a mono-, penta- or hexa-hydrous crystal as a hydrous crystalline form; or of an anhydrous crystal or anhydrous amorphous as an anhydrous form. Later, they further found that cyclotetrasaccharide in the form of an anhydrous crystal, monohydrous crystal, or anhydrous amorphous absorbs moisture and easily changes into its crystalline, penta- or hexa-hydrous form, as a hydrous form.

The present inventors further studied on applying the above features to dehydrating agents and resulted in a finding that the above-mentioned cyclotetrasaccharide in the form of an anhydrous crystal, monohydrous crystal, or anhydrous amorphous, has a satisfactory dehydrating ability; the dehydrated products produced therewith are highly stable. Thus, such a cyclotetrasaccharide can be widely applicable and more suitably used as a dehydrating agent as compared with conventional saccharides. In other words, the present inventors found that a cyclotetrasaccharide with dehydrating ability, i.e., a saccharide selected from cyclotetrasaccharides in the form of an anhydrous crystal, monohydrous crystal, or anhydrous amorphous can be incorporated into, contacted with, or coexisted in hydrous matters such as hydrous food products and hydrous pharmaceuticals to be converted into crystalline cyclotetrasaccharide, penta- or hexa-hydrate, whereby the cyclotetrasaccharide entraps a relatively large amount of moisture as a crystal water, acts as a dehydrating agent with a remarkably high dehydration power, and has a satisfactory stability. Thus, they found that such a cyclotetrasaccharide can be extensively used in hydrous matters including acid hydrous matters and confirmed that the cyclotetrasaccharide facilitates the production of dehydrated products such as high-quality dehydrated food products with satisfactory flavor, and dehydrated pharmaceuticals with satisfactory activity and stability. Thus the present inventors accomplished this invention.

The present invention is characterized in that it was made by appropriately selecting the desired cyclotetrasaccharide which had not been focused on its use as a dehydrating agent, particularly, it was firstly made by the present invention the method for dehydrating hydrous matters by incorporating, contacting, or coexisting a cyclotetrasaccharide with dehydrating ability into, with, or in hydrous matters.

BEST MODE FOR CARRYING OUT THE INVENTION

Figure 1:
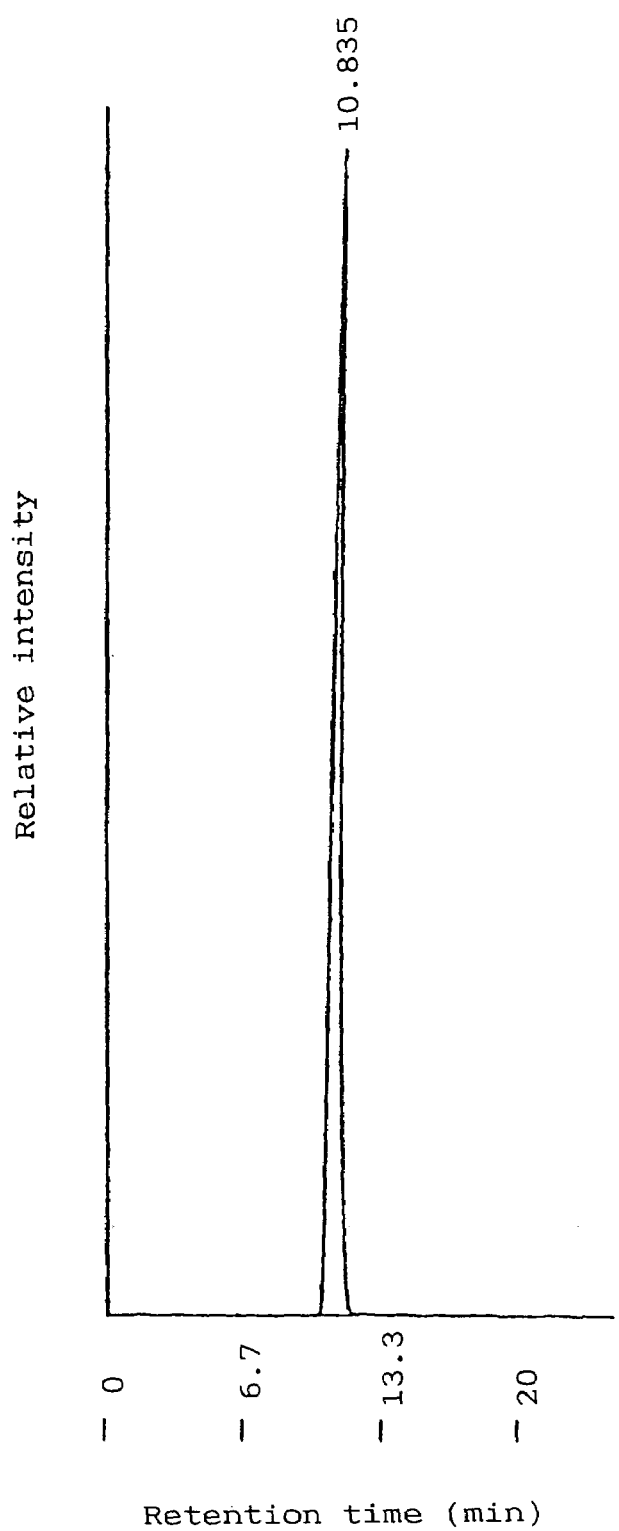
FIG. 1 is an elution pattern of a saccharide, obtained by the enzymatic reaction with α-isomaltosyl-transferring enzyme, when determined on high-performance liquid chromatography.

The method for dehydrating hydrous matters according to the present invention is advantageously applied to those which contain water, particularly, to those which contain free water but not bound water such as a crystal water. For example, the method can be advantageously applied to reduce the water content in the inner atmosphere of moisture-proof containers, which hermetically house dried food products, through a step of coexisting the dehydrating agent of the present invention therein; or to reduce the free water content of hydrous matters through a step of incorporating or contacting the dehydrating agent into or with such hydrous matters, for example, food products, cosmetics, pharmaceuticals, industrial chemicals, and their materials and processing intermediates.

When a cyclotetrasaccharide with dehydrating ability is allowed to contact with or coexisted in the above hydrous matters, such a cyclotetrasaccharide strongly entraps water, as a crystal water of crystalline cyclotetrasaccharide, penta- or hexa-hydrate, in an amount of about 11 to 15% (w/w) (the term "% (w/w)" is abbreviated as "%" throughout the specification) to the weight of the cyclotetrasaccharide used, from the hydrous matters, the level of which is 2.2–3-times higher than that of anhydrous maltose and 1.1–1.5-times higher than that of anhydrous α,α-trehalose; and effectively lowers the water content of the hydrous matters and dehydrates and/or dries them.

It was revealed that the coexistence of a cyclotetrasaccharide with dehydrating ability, in such a manner of injecting the saccharide into moisture permeable small bags such as paper bags and placing the resultants in moisture-proof containers which enclose hermetically dried foods such as seasoned layers and cookies, highly lowers the relative humidity within the containers and stably keeps the high quality of dried foods or powdery products for a relatively long period of time. In this case, the cyclotetrasaccharide does not either become sticky, melt to flow, or stain the dried foods or the containers even during or after entrapping water and being converted into crystalline cyclotetrasaccharide, penta- or hexa-hydrate.

As for high moisture content food products, for example, those in the form of a liquid or paste such as brandies, vinegars, royal jellies, fresh creams, and mayonnaises, they can be quite easily processed into high quality dehydrated food products having only a substantially reduced water content such as food products in the form of a massecuite or powder, through the steps of incorporating a cyclotetrasaccharide with dehydrating ability into such high moisture content products to effect dehydration while the saccharide being converted into its crystal, penta- or hexa-hydrate.

In that case, when the cyclotetrasaccharide is added to food materials in an amount sufficient to dehydrate the water in the food materials, the cyclotetrasaccharide is partly converted into crystalline cyclotetrasaccharide, penta- or hexa-hydrate. As a result, the resulting dehydrated food products, where the free water content is reduced, are prevented from quality change and deterioration due to bacterial contamination, hydrolysis, acidification, or browning; and their satisfactory quality, flavor, and taste will be retained for a relatively long period of time.

The dehydrating method of the present invention has the character that, since the cyclotetrasaccharide used in the present invention is a non-reducing saccharide and is free of severe conditions such as heat drying, high water content products in the form of a liquid or paste can be easily converted into dehydrated food products with satisfactory flavor and taste and a reduced water content. Cyclotetrasaccharide per se is a non-toxic and harmless sweetener having a sweetening power of about 20% of that of sucrose, and is free of side effect.

In the case of applying the dehydrating method to aqueous solutions of lymphokines or antibiotics and to pasty pharmaceuticals such as ginseng extracts and turtle extracts, they can be quite easily converted into high quality dehydrated pharmaceuticals with substantially reduced water content, for example, pharmaceuticals in the form of a massecuite or powder, by incorporating a cyclotetrasaccharide with dehydrating ability into the above aqueous solutions and the pasty pharmaceuticals to convert the cyclotetrasaccharide into its crystal, penta- or hexa-hydrate. According to the dehydrating method, high quality and stable dehydrated pharmaceuticals are prepared because it does not require severe conditions such as heat drying and the cyclotetrasaccharide functions as a dehydrating agent and a stabilizer for the effective ingredients of pharmaceuticals.

For example, solid preparations can be arbitrarily prepared by placing in vials a cyclotetrasaccharide with a sufficiently high level of dehydrating ability, injecting into the vials an aqueous solution containing a physiologically active substance(s) such as a lymphokine or hormone, and sealing the vials. In this case, the cyclotetrasaccharide dehydrates the aqueous solution and also absorbs/dries the gas spaces of the vials. The dehydrated solid pharmaceuticals have the features that they are preparable through a relatively easy processing, retain their high quality for a relatively long period of time, and easily dissolve in water in use.

High quality, stable solid preparations can be prepared by mixing a prescribed amount of an aqueous solution containing a physiologically active substance(s) with the cyclotetrasaccharide with a sufficiently high level of dehydrating ability under stirring conditions, and directly placing and sealing the resulting power in a container. Further, the solid preparations can be arbitrarily processed in a usual manner into granules or tablets for use.

Unlike conventionally known dehydrating agents such as a silica gel or calcium oxide, the dehydrating agent of the present invention, comprising a cyclotetrasaccharide with dehydrating ability, is a non- or low-caloric saccharide dehydrating agent that is edible and substantially non-assimilable when ingested orally, and it can be advantageously used as a stabilizer for physiologically active substances.

The cyclotetrasaccharide and the one with dehydrating ability used in the present invention should not be restricted to their origins and processes. As described later, a cyclotetrasaccharides with dehydrating ability, for example, those in an anhydrous crystalline- or anhydrous amorphous-form, can be preferably used because they absorb moisture to be converted into crystalline cyclotetrasaccharide, penta- or hexa-hydrate. Similarly, crystalline cyclotetrasaccharide, monohydrate, also absorbs moisture to be converted into crystalline cyclotetrasaccharide, penta- or hexa-hydrate, resulting in an exertion of dehydrating action. Accordingly, the cyclotetrasaccharide with dehydrating ability used in the present invention should not be limited to cyclotetrasaccharide in a completely anhydrous form and includes, for example, those in a hydrous form as long as they have dehydrating ability without any inconvenience. Thus, the cyclotetrasaccharide with dehydrating ability used in the present invention can be defined by evaluating the moisture content of the saccharide using a conventional method such as the Karl Fischer method. Of course, the moisture content of the cyclotetrasaccharide as the effective ingredient of the dehydrating agent of the present invention should preferably be as low as possible, desirably, less than 4%, more desirably, less than 3%. Even a cyclotetrasaccharide with a moisture content of 4% or higher but less than 10% has dehydrating ability, however, such a saccharide merely has a relatively lower function and efficiency as a dehydrating agent.

Prior to establishing the present invention, the present inventors studied methods for producing cyclotetrasaccharides with dehydrating ability, particularly, anhydrous crystalline cyclotetrasaccharide; crystalline cyclotetrasaccharide, monohydrate; and anhydrous amorphous cyclotetrasaccharide.

Methods for producing such cyclotetrasaccharides include, for example, an enzymatic method using amylaceous substances as materials; a method where hydrolytic enzymes, i.e., alternanase is allowed to act on alternan, as disclosed in *European Journal of Biochemistry*, Vol. 226, pp. 641–648 (1994); a method of converting panose prepared from starch into cyclotetrasaccharide using α-isomaltosyl-transferring enzyme, as disclosed in Japanese Patent Application Nos. 229,557/2000 and 234,937/2000; and a method of producing cyclotetrasaccharide from starch using α-isomaltosylglucosaccharide-forming enzyme and α-isomaltosyl-transferring enzyme in combination. In addition, as disclosed in the specifications of the above applications prior to the present application, the present inventors revealed that, as a method for producing cyclotetrasaccharide, such an enzymatic method using amylaceous substances which are more abundant and cheaper than alternan, can be advantageously used for industrial scale production because it produces the desired cyclotetrasaccharide at a relatively high efficiency and a lesser cost. Also they firstly revealed that cyclotetrasaccharide exists, for example, in the form of a penta- or hexa-hydrate crystal, anhydrous crystal, monohydrous crystal, or anhydrous amorphous crystal.

Examples of microorganisms which form α-isomaltosyl-glucosaccharide-forming enzyme and α-isomaltosyl-transferring enzyme include *Bacillus globisporus* C9 strain and *Bacillus globisporus* C11 strain, which were deposited on Apr. 25, 2000, and have been maintained in International Patent Organism Depositary National Institute of Advanced Industrial Science and Technology Tsukuba Central 6, 1-1, Higashi 1-Chome Tsukuba-shi, Ibaraki-ken, 305-8566, Japan, under the accession numbers of FERM BP-7143 and FERM BP-7144, respectively.

The present inventors further studied the process for producing anhydrous crystalline cyclotetrasaccharide and then established the following; a process comprising the steps of, for example, preparing an aqueous solution of cyclotetrasaccharide, produced from amylaceous substances using any of the above-mentioned enzymatic methods, into a high concentrated syrup with a concentration of over 2.0% but less than 12%, keeping the concentrate at a temperature of 50–180° C. in the presence of a seed crystal of anhydrous crystalline cyclotetrasaccharide, crystallizing anhydrous crystalline cyclotetrasaccharide, and pulverizing the resulting crystals.

A powdery crystalline cyclotetrasaccharide, monohydrate, is prepared, for example, by adequately drying a powdery cyclotetrasaccharide, penta- or hexa-hydrate, at a temperature of about 100° C. to about 180° C.

To produce anhydrous amorphous cyclotetrasaccharide, for example, an aqueous solution of cyclotetrasaccharide obtained by any of the above-mentioned methods is lyophilized or dried at a temperature of about 100° C. to about 180° C. and at a normal pressure or in vacuo, and pulverizing the resultant. The above aqueous solution of cyclotetrasaccharide can be prepared into an about 40–85% syrup, lyophilized or dried in vacuo, and pulverized; or can be directly processed into a powder form by the spraying- and the drying-methods such as the high pressure nozzle method or the rotatory disk method.

As the method for pulverization, apart from the above spraying and drying methods, for example, conventional methods such as block pulverization method, extrusion granulation method, and fluidized-bed granulation method can be appropriately employed.

The powdery cyclotetrasaccharide with dehydrating ability thus obtained is a non-reducing, free-flowing, white powder with a high quality, low sweetness, and is low in moisture content or substantially anhydrous; usually, the moisture content is less than 4%, preferably, less than 3% when determined on the Karl Fisher method. The powder can be made into an anhydrous crystalline powder, crystalline monohydrate powder, or anhydrous amorphous powder.

Depending on use, the powdery cyclotetrasaccharide with dehydrating ability can be arbitrarily sized. In the case of preparing small portions or tablets such as of medicaments, a cyclotetrasaccharide with a smaller particle size is more preferably used because the smaller the particle size of cyclotetrasaccharide the more the effective ingredients can be homogeneously dispersed. The particle size of the dehydrating agent of the present invention can be appropriately controlled by conventional means for classification using meshes, etc.; usually those with a particle size of 20–500 μm, preferably, 50–200 μm can be arbitrarily used.

Any powdery cyclotetrasaccharides with dehydrating ability can be used in the present invention as long as they are anhydrous cyclotetrasaccharides which exert a strong dehydrating action during their conversion into crystalline cyclotetrasaccharide, penta- or hexa-hydrate. For example, preferably used are those which comprise anhydrous cyclotetrasaccharide supplemented with, as a seed, crystalline cyclotetrasaccharide, penta- or hexa-hydrate, in the least possible amount, usually, in an amount of less than 5%, preferably, less than 1%.

When incorporated into hydrous matters such as food products, cosmetics, pharmaceuticals, and industrial chemicals, the powdery cyclotetrasaccharides with dehydrating ability thus obtained act as a strong dehydrating agent for hydrous matters in such a manner of entrapping and holding the free water in the hydrous matters as a crystal water of crystalline cyclotetrasaccharide, penta- or hexa-hydrate.

Appropriate examples, which the dehydrating agent of the present invention is advantageously applicable to, include those wherein the agent is placed in moisture-proof containers to dehydrate or dry the inner atmosphere in the containers, and methods for producing high-quality dehydrated products in the form of a massecuite, powder, or solid by contacting the agent with hydrous matters susceptible to change in quality or deterioration during heat drying or drying in vacuo.

Examples of the above application of the dehydrating agent to dehydrate or dry hydrous matters include those for preventing seasoned layers, cookies, etc., from absorbing moisture. According to the present invention, a cyclotetrasaccharide with dehydrating ability can be used in such a manner of incorporating it into the following powdery products susceptible to absorbing moisture and solidifying, and then sealing the products in containers to lower the relative humidity within the containers and prevent the adhesion or solidification of the products, resulting in an exertion of their high quality and satisfactory free-flowing ability just after their processings: cereal powders such as rice powders, wheat flours, and soy bean flours; processed serials such as a hattaiko (a flour of heated and ground rice or wheat), kinako (a soy bean powder), and ground sesame; premix flours such as a premix of pudding and hot cake mix; fine granular crystalline seasonings such as salts and sugars; seasoning powders such as a powdered soy sauce, powdered miso, powdered vinegar for sushi, premix of soup stock powder, and powdered complex seasoning; powdered spices such as a powdered garlic, powdered cinnamon, powdered nutmeg, powdered pepper, and powdered sage; and other powdered products such as a powdered yeast extract, powdered milk, powdered yoghurt, powdered cheese, powdered juice, powdered herb, powdered vitamin, powdered soup, powdered bouillon, fish flour, blood meal, bone meal, powdered preparation of lactic acid bacteria, powdered enzyme preparation, and granular digestive.

In the case of applying the dehydrating agent of the present invention to dehydrate hydrous matters, for example, the agent can be arbitrarily used to dehydrate a variety of hydrous matters such as organs, tissues, and cells of animals, plants, and microorganisms, as well as their ground products, extracts, ingredients, and preparations.

In the case of applying the dehydrating agent of the present invention to food products and their materials and intermediates, dehydrated food products with satisfactory stability, flavor, and taste can be easily processed from those in the form of a liquid or paste, for example, agricultural products such as a fresh fruit, juice, vegetable extract, soybean milk, sesame paste, nut paste, raw bean's paste, gelatinized starch paste, and wheat flour; fishery products such as a paste of sea urchin, oyster extract, and paste of Japanese pilchard; livestock products such as a fresh egg, lecithin, milk, milk serum, cream, yoghurt, butter, and cheese; hydrous seasonings such as a maple syrup, honey, miso, soy sauce, mayonnaises, dressing, bonito extract, meat extract, tangle extract, mushroom extract, licorice extract, stevia extract, and their enzyme treated products and seasoning liquids for pickling; alcohols such as a Japanese sake, wine, brandy, whisky, and medicated liquor; beverages for preference such as a green tea, tea, and coffee; hydrous spices such as an extract of mint, Japanese horseradish, garlic, mustard, Japanese pepper, cinnamon, sage, laurel, pepper, and citrus; hydrous colors such as *Rubia tinctorum* L.; hydrous emulsifiers prepared, for example, from sucrose fatty acid esters, glycerin fatty acid esters, and sorbitan fatty acid esters; and preservation liquids such as smoke solutions and fermented liquids.

Among the dehydrated products thus obtained, the powdered products of agriculture, fishery, and livestock; powdered flavors; powdered colors; powdered emulsifiers; and powdered preservatives can be arbitrarily used as natural bulk flavors with satisfactory flavor and taste or processing materials in seasonings such as mayonnaises and soup premixes, confectioneries such as hard candies and cakes, and premixes such as hot cake mixes and instant juices.

In the case of applying the dehydrating agent of the present invention to pharmaceuticals and their materials and processing intermediates, dehydrated pharmaceuticals and health foods with satisfactory stability and high quality without losing the effective ingredients and activities in the following liquid or paste products: Examples of such are liquids containing lymphokines such as $\alpha$-, $\beta$- or $\gamma$-interferon, tumor necrosis factor-$\alpha$ (TNF-$\alpha$), tumor necrosis factor-$\beta$ (TNF-$\beta$), macrophage migration inhibitory factor, colony-stimulating factor, transfer factor and interleukin 2; liquids containing hormones such as insulin, growth hormone, prolactin, erythropoietin, and follicle-stimulating hormone; liquids containing biological preparations such as BCG vaccine, Japanese encephalitis vaccine, measles vaccine, live polio vaccine, smallpox vaccine, tetanus toxoid, *Trimeresurus* antitoxin, and human immunoglobulin; liquids containing antibiotics such as penicillin, erythromycin, chloramphenicol, tetracycline, streptomycin, and kanamycin sulfate; liquids containing vitamins such as thiamine, riboflavin, L-ascorbic acid, cod liver oil, carotenoid, ergosterol, and tocopherol; liquids containing enzymes such as lipase, elastase, urokinase, protease, $\beta$-amylase, isoamylase, glucanase, and lactase; extracts such as ginseng extract, snapping turtle extract, chlorella extract, aloe extract, and propolis extract; pastes of viable microorganisms such as viruses, lactic acid bacteria, and yeasts; and other liquid or paste products such as royal jellies.

Similarly as in the above food products and pharmaceuticals, the dehydrating agent of the present invention is applied to cosmetics and their materials and processing intermediates such as fresh eggs, lecithin, creams, honeys, licorice extracts, flavors, colors, and enzymes to dehydrate them into high quality, dehydrated cosmetics which are advantageously used as skin-beautifying agents, hair-beautifying agents, and hair restorers.

In the case of applying the dehydrating agent to enzyme preparations to be dehydrated, the obtained preparations can be arbitrarily used as catalysts for processing food products, pharmaceuticals, and industrial materials; or as therapeutic agents, digestives, or enzyme detergents.

The methods for incorporating, contacting or coexisting the cyclotetrasaccharide with dehydrating ability into, with, or in hydrous matters are mixing, kneading, dissolving, penetrating, dispersing, applying, spraying, and injecting, which are appropriately selected before completing the dehydration of the hydrous matters.

Depending on the water content of hydrous matters to be dehydrated and the properties of the desired dehydrated matters, it is varied the amount of a cyclotetrasaccharide with dehydrating ability to be incorporated into, or contacted with or coexisted in hydrous matters. If necessary, prior to incorporate, contact or coexist the cyclotetrasaccharide with dehydrating ability into, with, or in hydrous matters, the hydrous matters are preferably partially dehydrated or concentrated with other conventional dehydrating methods. Usually, 0.001–200 parts by weight, preferably, 0.01–50 parts by weight of the cyclotetrasaccharide is used to one part by weight of a hydrous matter.

To improve the quality of the resulting dehydrated products such as food products, cosmetics, and pharmaceuticals, appropriate flavors, colors, taste-imparting materials, stabilizers, and fillers can be arbitrarily used in combination. Particularly, since the dehydrating method of the present invention is a quite effective dehydration method using a cyclotetrasaccharide with strong dehydrating ability, the aforesaid stabilizers should not be limited to lower molecular weight compounds such as antioxidants. The following water-soluble high molecular weight compounds, whose dehydration have been deemed difficult, can be arbitrarily used as such stabilizers; soluble starch, dextrin, pullulan, elsinan, dextran, xanthan gum, gum arabic, locust bean gum, guar gum, tragacanth gum, tamarind gum, carboxy methyl cellulose, hydroxy ethyl cellulose, pectin, agar, gelatin, albumin, and casein.

In the case of using the above water-soluble high molecular compounds, for example, they are first homogeneously dissolved in hydrous matters in a liquid or paste form, then a cyclotetrasaccharide with dehydrating ability is incorporated into the resulting mixtures by the methods such as mixing and kneading to obtain dehydrated products with fine cyclotetrasaccharide crystals, penta- or hexa-hydrate.

The above dehydrated matters quite advantageously, stably retain the flavor and effective ingredients from the hydrous matters because the ingredients are prevented from dispersion and deterioration by either the coating with films of the high molecular substances; the encapsulation in microcapsules, surrounded with the films, together with the fine cyclotetrasaccharide crystals, penta- or hexa-hydrate; or the stabilization of flavor ingredients or effective ingredients by forming inclusion compounds using a cyclotetrasaccharide with dehydrating ability. In this case, if necessary, $\alpha$-, $\beta$- or $\gamma$-cyclodextrin, capable of forming inclusion compounds of flavor ingredients, can be arbitrarily used as the water-soluble high molecular substances.

The cyclodextrins usable in the present invention should not be limited to those with a high purity but arbitrarily include those with a low purity, which are hard to be dehydrated and pulverized, for example, glucose derivatives of cyclodextrins and partial starch hydrolyzates in the form of a hydrolyzed starch syrup rich in maltodextrins and containing different types of cyclodextrins.

The methods used for producing the dehydrated products according to the present invention, particularly, those for pulverized dehydrated products are variable. For example, a cyclotetrasaccharide with dehydrating ability is incorporated to homogeneity into hydrous matters with a relatively high moisture content such as food products, cosmetics, pharmaceuticals, and their materials and processing intermediates to give a moisture content of about 50% or lower, preferably, about 10 to 40% to the total weight of the resulting dehydrated products. The resulting mixtures are then allowed to stand in a vat at a temperature of about 10° C. to about 50° C., for example, at ambient temperature, for about 0.1 to about 5 days to be solidified into blocks through the conversion of the cyclotetrasaccharide into crystalline cyclotetrasaccharide, penta- or hexa-hydrate, followed by cutting and pulverizing the blocks. If necessary, drying and classifying steps can follow a pulverization step such as cutting and pulverizing.

By applying a spraying method, pulverized products can be directly produced. For example, the methods below can be suitably used as an industrial scale production method of the powdery dehydrated products of the present invention: A method comprising the steps of spraying a prescribed amount of a liquid or paste hydrous matter over a cyclotetrasaccharide with dehydrating ability under free-flowing conditions to contact them each other, granulating the resulting mixture, and optionally aging the resulting granules at about 30° C. to about 60° C. for about 0.1 to about 10 hours to convert the cyclotetrasaccharide into crystalline cyclotetrasaccharide, penta- or hexa-hydrate; or a method comprising the steps of mixing and kneading a liquid or pasty hydrous matter with a cyclotetrasaccharide with dehydrating ability, and then instantly or after initiating the conversion of the cyclotetrasaccharide into crystalline cyclotetrasaccharide, penta- or hexa-hydrate, and optionally spraying the resultant into a powder and optionally aging similarly as above to convert the remaining cyclotetrasaccharide into crystalline cyclotetrasaccharide, penta- or hexa-hydrate.

The powdery dehydrated products thus obtained can be arbitrarily used intact or, if necessary, in combination with fillers, adjuvants, binders, stabilizers, etc., or after processed into an appropriate form such as a granule, tablet, capsule, rod, plate, or cubic.

Since starch generally requires a relatively large amount of water for swelling and gelatinizing, the resulting swelled and gelatinized starch is highly susceptible to bacterial contamination. The cyclotetrasaccharide with dehydrating ability can be effectively used as a dehydrating agent for such gelatinized starch. For example, gelatinized starch such as "gyuhi" (a rice paste with sugar) can be prevented from bacterial contamination by incorporating a cyclotetrasaccharide with dehydrating ability thereunto to substantially reduce the water content thereof.

The cyclotetrasaccharide with dehydrating ability can be easily mixed to homogeneity with gelatinized starch and acts as a retrogradation preventive as described later, and it can prolong the shelf-life of processed foods containing gelatinized starch by a large margin.

In applying a cyclotetrasaccharide with dehydrating ability over the surface of high moisture content food products, which are susceptible to bacterial contamination, such as a peeled banana, orange, sliced steamed/boiled sweet-potato, split jack, hairtail, raw noodle, boiled noodle, and rice confectionery, the cyclotetrasaccharide contacts the food products by sprinkling over the surface of the food products to convert the cyclotetrasaccharide into crystalline cyclotetrasaccharide, penta- or hexa-hydrate, resulting in a substantial reduction of the water content on the surface of the food products and an improvement of their shelf-life and quality. For this reason the cyclotetrasaccharide with dehydrating ability can be advantageously used as a food preservative, stabilizer, or quality-improving agent. In this case, the shelf-life of the above food products can be further prolonged by optionally using lactic acid, citric acid, or ethanol; or by vacuum package, gas-filling package, or refrigeration.

Since the cyclotetrasaccharide with dehydrating ability has a relatively high affinity to alcohols, it can be arbitrarily used as a dehydrating agent for water contained in alcohols and alcohol-soluble products such as methanol, ethanol, butanol, propylene glycol, glycerine, and polyethylene glycol.

For example, alcohols such as sake, shochu (a distilled spirit), wine, brandy, whisky, and vodka can be advantageously processed into a massecuite or powder which retains the effective ingredients and flavors of these alcohols by dehydrating the alcohols using a cyclotetrasaccharide with dehydrating ability to form crystalline cyclotetrasaccharide, penta- or hexa-hydrate, while allowing to incorporate their effective ingredients and flavors into the crystal. The powdery alcohols thus obtained can be used in confectioneries and premixes which are mixed with water into beverages before use.

When coexisted in dehydrated hydrous matters, the cyclotetrasaccharide with dehydrating ability used in the present invention functions as a dehydrating agent or stabilizer and also exerts an effect as an agent for imparting high-quality sweetness, body, or adequate viscosity.

By mixing a cyclotetrasaccharide with dehydrating ability with an alcohol solution such as of iodine and then with an aqueous solution containing a water-soluble high molecule, etc., the cyclotetrasaccharide is converted into its crystal, penta- or hexa-hydrate, resulting in stabilizing the effective ingredients such as iodine without volatilizing and deteriorating them, and facilitating the production of ointments in a massecuite form having an adequate viscosity, extendibility, and adhesion.

Food products such as powdery fats and oils, spices, flavors, and food colors; cosmetics; and pharmaceuticals such as powdery vitamins and hormones are advantageously obtainable by soaking or mixing water-containing-oil-soluble substances, emulsions, or latexes in or with the cyclotetrasaccharide with dehydrating ability to convert a cyclotetrasaccharide with dehydrating ability into its crystal, penta- or hexa-hydrate.

In such a case, the cyclotetrasaccharide with dehydrating ability functions as a dehydrating agent and as a stabilizer, property-retaining agent, filler, or carrier even after converted into cyclotetrasaccharide crystal, penta- or hexa-hydrate.

The cyclotetrasaccharide with dehydrating ability used in the present invention can be advantageously used even in food products containing oil-soluble substances, which are incompatible with water, such as chocolates and creams. In this case, the cyclotetrasaccharide is used not only as a dehydrating agent but used for improving processibility, meltability in mouth, flavor and taste. The products thus obtained have a feature of stably retaining their high quality for a relatively long period of time.

As described above, the present invention was made based on the finding that a cyclotetrasaccharide with dehydrating ability strongly absorbs moisture from hydrous matters, and that the resulting dehydrated products are highly stable. When used as a dehydrating agent, the cyclotetrasaccharide with dehydrating ability dehydrates hydrous matters in a liquid or paste form and facilitates to produce high quality pharmaceuticals and cosmetics with reduced moisture content without deteriorating or volatilizing the taste or the flavor of the hydrous matters by the characteristic enclosing action of the cyclotetrasaccharide.

The following are the preferred examples for use according to the present invention:

The cyclotetrasaccharide with dehydrating ability used in the present invention has a relatively low sweetness and can be also used as a seasoning free from caries inducibility and increment of blood cholesterol- and/or blood sugar-levels. If necessary, the cyclotetrasaccharide can be used, for example, by mixing with other sweetener(s) such as a powdered syrup, glucose, isomerized sugar, sucrose, maltose, α,α-trehalose, honey, maple sugar, sorbitol, maltitol, dihydrocharcone, stevioside, α-glycosyl stevioside, rebaudioside, glycyrrhizin, thaumatin, L-aspartyl L-phenylalanine methyl ester, acesulfame K, sucralose, saccharin, glycine, and alanine; and fillers such as dextrin, starch, and lactose.

The cyclotetrasaccharide with dehydrating ability is a non-reducing saccharide which has a high quality sweetness inherent to cyclotetrasaccharide; well harmonizes with other tastable materials having sour-, acid-, salty-, astringent-, delicious-tastes, and bitter-tastes; and has a relatively high acid- and heat-resistance. Thus, the cyclotetrasaccharide can be favorably used in food products in general as a sweetener, taste-improving agent, quality-improving agent, or flavor-improving agent.

The cyclotetrasaccharide can be used as a dehydrating agent in seasonings such as a soy sauce, powdered soy sauce, "miso", "funmatsu-miso" (a powdered miso), "moromi" (a refined sake), "hishio" (a refined soy sauce), "furikake" (a seasoned fish meal), mayonnaise, dressing, vinegar, "sanbai-zu" (a sauce of sugar, soy sauce and vinegar), "funmatsu-sushi-su" (powdered vinegar for sushi), "chuka-no-moto" (an instant mix for Chinese dish), "tentsuyu" (a sauce for Japanese deep-fat fried food), "mentsuyu" (a sauce for Japanese vermicelli), sauce, catsup, "yakiniku-no-tare" (a sauce for Japanese grilled meat), curry roux, instant stew mix, instant soup mix, "dashi-no-moto" (an instant stock mix), "mirin" (a sweet sake), "shin-mirin" (a synthetic mirin), table sugar, and coffee sugar. Also, the cyclotetrasaccharide can be arbitrarily used as a sweetener, taste-improving agent, quality-improving agent, or taste/flavor-improving agent. Further, the cyclotetrasaccharide can be freely used as a dehydrating agent, sweetener, taste-improving agent, quality-improving agent, or taste/flavor-improving agent in "wagashi" (Japanese cakes) such as "senbei" (a rice cracker), "arare-mochi" (a rice-cake cube), "okoshi" (a millet-and-rice cake), "gyuhi" (a rice paste with sugar), "mochi" (a rice paste) or the like, "manju" (a bun with a bean-jam), "uiro" (a sweet rice jelly), "an" (a bean jam) or the like, "yokan" (a sweet jelly of beans), "mizu-yokan" (a soft adzuki-bean jelly), "kingyoku" (a kind of yokan), jelly, pao de Castella, and "amedama" (a Japanese toffee); confectioneries such as a bun, biscuit, cracker, cookie, pie, pudding, butter cream, custard cream, cream puff, waffle, sponge cake, doughnut, chocolate, chewing gum, caramel, nougat, and candy; frozen desserts such as an ice cream and sherbet; syrups such as "kajitsu-no-syrup-zuke" (a preserved fruit) and "korimitsu" (a sugar syrup for shaved ice); pastes such as a flour paste, peanut paste, and fruit paste; processed fruits and vegetables such as a jam, marmalade, "syrup-zuke" (fruit pickles), and "toka" (conserves); pickles and pickled products such as "fukujin-zuke" (red colored radish pickles), "bettara-zuke" (a kind of whole fresh radish pickles), "senmai-zuke" (a kind of sliced fresh radish pickles) and "rakkyo-zuke" (pickled shallots); premixes for pickles and pickled products such as "takuan-zuke-no-moto" (a premix for pickled radish) and "hakusai-zuke-no-moto" (a premix for fresh white rape pickles); meat products such as a ham and sausage; products of fish meat such as a fish ham, fish sausage, "kamaboko" (a steamed fish paste), "chikuwa" (a kind of fish paste), and "tenpura" (a Japanese deep-fat fried fish paste); "chinmi" (relishes) such as "uni-no-shiokara" (salted guts of sea urchin), "ika-no-shiokara" (salted guts of squid), "su-konbu" (processed tangle), "saki-surume" (dried squid strips) and "fugu-no-mirin-boshi" (a dried mirin-seasoned swellfish); "denpu" (a fish meet boiled down, seasoned, and dried) such as those of cod, sea bream, and shrimp; "tsukudani" (foods boiled down in soy sauce) such as those of layer, edible wild plants, dried squid, fish, and shellfish; daily dishes such as "nimame" (a cooked bean), potato salad, and "konbu-maki" (a tangle roll); milk products; canned and bottled products such as those of meat, fish meat, fruit, and vegetable; alcoholic beverages such as a synthetic sake, wine, and liquors; soft drinks such as coffee, tea, cocoa, juice, carbonated beverage, sour milk beverage, and beverage containing lactic acid bacteria; and instant food products such as an instant pudding mix, instant hot cake mix, "sokuseki-shiruco" (an instant mix of adzuki-bean soup with rice cake), and instant soup mix.

The following explain the process for producing the cyclotetrasaccharides usable in the present invention and properties thereof:

Experiment 1

Preparation of Cyclotetrasaccharide from Culture

A liquid culture medium consisting of 5% (w/v) of "PINE-DEX #1", a partial starch hydrolysate commercialized by Matsutani Chemical Ind., Tokyo, Japan, 1.5% (w/v) of "ASAHIMEAST", a yeast extract commercialized by Asahi Breweries, Ltd., Tokyo, Japan, 0.1% (w/v) of sodium dihydrogen phosphate, dodecahydrate, 0.06% (w/v) of magnesium sulfate, dodecahydrate, and water was placed in a 500-ml Erlenmeyer flask in an amount of 100 ml, sterilized by autoclaving at 121° C. for 20 min, cooled, and then seeded with *Bacillus globisporus* C9 strain, FERM BP-7143, followed by culturing under rotary-shaking conditions at 27° C. and 230 rpm for 48 hours and centrifuging the resulting culture to remove cells to obtain a supernatant. The supernatant was autoclaved at 120° C. for 15 min and then cooled, and the resulting insoluble substances were removed by centrifugation to obtain a supernatant.

To examine the saccharides in the resulting supernatant, they were separated from the supernatant on silica gel thin-layer chromatography (abbreviated as "TLC" hereinafter) using, as a developer, a mixture solution of n-butanol, pyridine, and water (=6:4:1 by volume), and, as a thin-layer plate, "KIESELGEL 60", an aluminum plate (20×20 cm) for TLC commercialized by Merck & Co., Inc., Rahway, USA. Whole of the separated sugars and the reducing sugars among them were respectively examined by coloring with the sulfuric acid-methanol method and the diphenylamine-aniline method. The examination detected a non-reducing saccharide, positively detected on the former detection method at a position with an Rf value of about 0.31 but negative on the latter detection method.

About 90 ml of the above supernatant was adjusted to pH 5.0 and 45° C. and then treated for 24 hours with 1,500 units/g solids of "TRANSGLUCOSIDASE L AMANO™", an α-glucosidase commercialized by Amano Pharmaceutical Co., Ltd., Aichi, Japan, and 75 units/g solids of a glucoamylase commercialized by Nagase Biochemicals, Ltd., Kyoto, Japan. Then, the resulting mixture was adjusted to pH 12 by the addition of sodium hydroxide and boiled for two hours to decompose the remaining reducing sugars. After removing insoluble substances by filtration, the resulting solution was decolored and desalted with "DIAION PK218" and "DIAION WA30", cation exchange resins commercialized by Mitsubishi Chemical Industries, Ltd., Tokyo, Japan, and further desalted with "DIAION SK-1B", commercialized by Mitsubishi Chemical Industries, Ltd., Tokyo, Japan, and "AMBERLITE IRA411", an anion exchange resin commercialized by Japan Organo Co., Ltd., Tokyo, Japan, followed by successive decoloration with an activated charcoal, membrane filtration, concentration by an evaporator, and lyophilization in vacuo to obtain about 0.6 g, d.s.b., of a saccharide powder.

The analysis of the saccharide on high-performance liquid chromatography (abbreviated as "HPLC" hereinafter) detected only a single peak at an elution time of 10.84 min as shown in FIG. 1, revealing that the saccharide had a significantly high purity of 99.9% or higher. The HPLC was run using a column of "SHOWDEX KS-801", Showa Denko K.K., Tokyo, Japan, at a column temperature of 60° C. and a flow rate of 0.5 ml/min of water, and using "R1-8012", a differential refractometer commercialized by Tosoh Corporation, Tokyo, Japan.

When measured for reducing power on the Somogyi-Nelson's method, the specimen had a reducing power below a detectable level, revealing that the specimen was a substantially non-reducing saccharide.

Experiment 2

Structure Analysis of Cyclotetrasaccharide

Fast atom bombardment mass spectrometry (called "FAB-MS") on a non-reducing saccharide, obtained by the method in Experiment 1, clearly detected a proton-addition-molecular ion with a mass number of 649, revealing that the saccharide had a mass number of 648.

According to conventional manner, the saccharide was hydrolyzed with sulfuric acid and analyzed for sugar composition on gas chromatography. As a result, only D-glucose was detected, revealing that the saccharide tested was composed of D-glucose molecules. Based on the data and the above mass number, the saccharide was estimated to be a cyclotetrasaccharide, composed of four D-glucose molecules.

Figure 2:
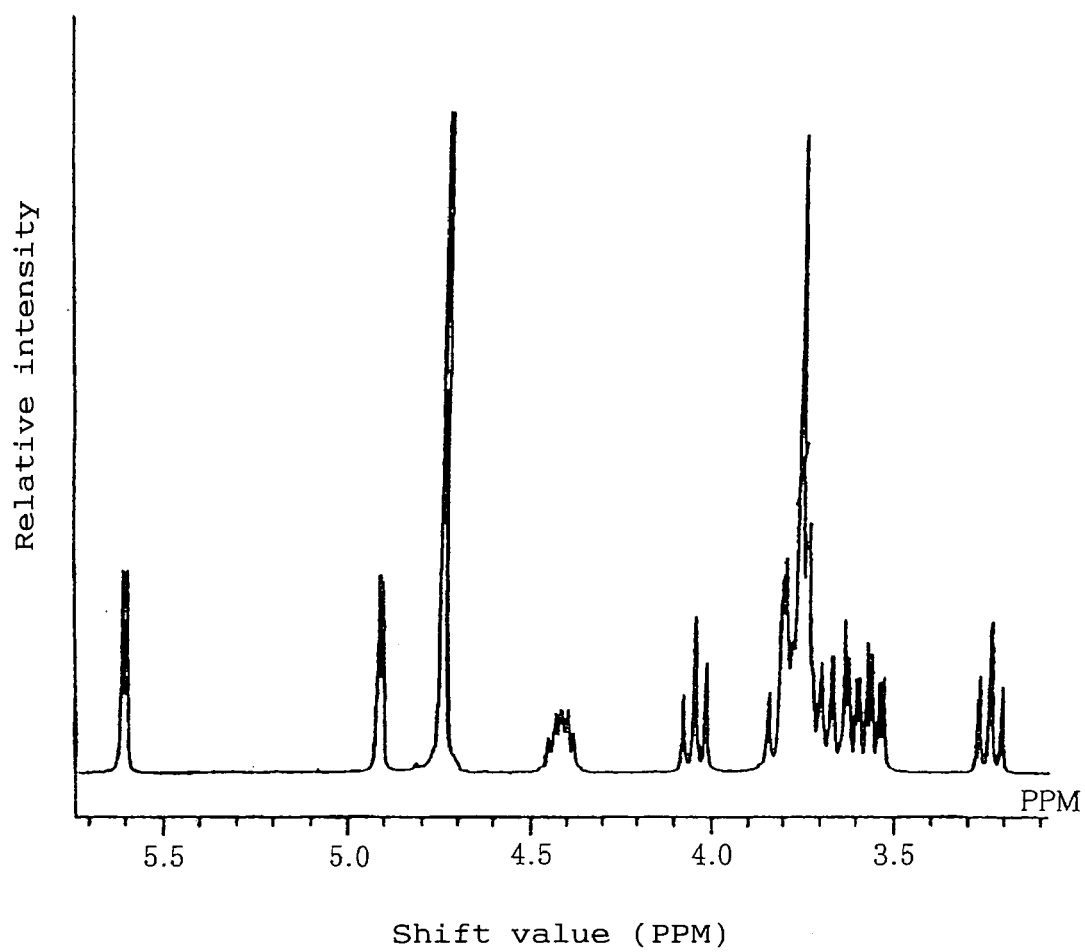
FIG. 2 is a nuclear resonance spectrum ($^1$H-NMR) of cyclotetrasaccharide, obtained by the enzymatic reaction with α-isomaltosyl-transferring enzyme.
Figure 3:
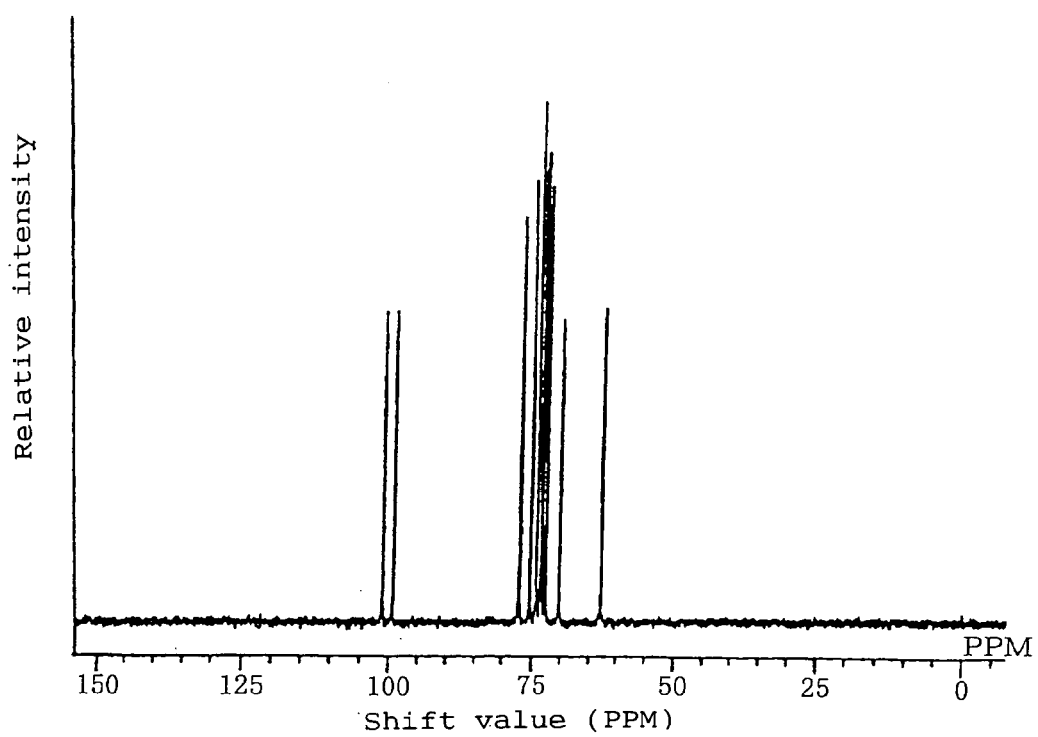
FIG. 3 is a nuclear resonance spectrum ($^{13}$C-NMR) of cyclotetrasaccharide, obtained by the enzymatic reaction with α-isomaltosyl-transferring enzyme.
Figure 4:
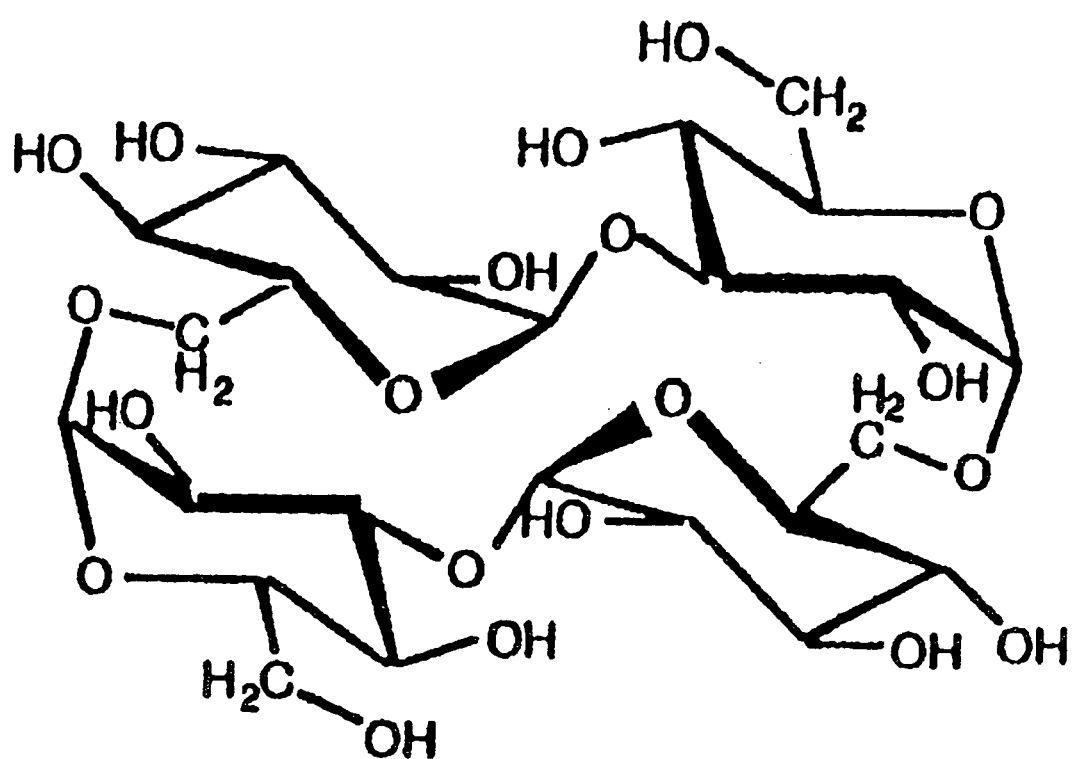
FIG. 4 shows that cyclotetrasaccharide has the structure of cyclo{→6)-α-D-glucopyranosyl-(1→3)-α-D-glucopyranosyl-(1→6)-α-D-glucopyranosyl-(1→3)-α-D-glucopyranosyl-(1→}.

Nuclear magnetic resonance analysis (called "NMR") on the saccharide gave a $^1$H-NMR spectrum in FIG. 2 and a $^{13}$C-NMR spectrum in FIG. 3, and these spectra were compared with those of authentic saccharides, revealing that they were coincided with a non-reducing cyclic saccharide, cyclo{→6)-α-D-glucopyranosyl-(1→3)-α-D-glucopyranosyl-(1→6)-α-D-glucopyranosyl-(1→3)-α-D-glucopyranosyl-(1→} as disclosed in "*European Journal of Biochemistry*", pp. 641–648 (1994). The data confirmed that the saccharide was a cyclotetrasaccharide in FIG. 4, i.e., cyclo{→6)-α-D-glucopyranosyl-(1→3)-α-D-glucopyranosyl-(1→6)-α-D-glucopyranosyl-(1→3)-α-D-glucopyranosyl-(1→}.

Experiment 3

Production of α-Isomaltosylglucosaccharide-Forming Enzyme from *Bacillus globisporus* C9 Strain A liquid culture medium consisting of 4.0% (w/v) of "PINE-DEX #4", a partial starch hydrolysate commercialized by Matsutani Chemical Ind., Tokyo, Japan, 1.8% (w/v) of "ASAHIMEAST", a yeast extract commercialized by Asahi Breweries, Ltd., Tokyo, Japan, 0.1% (w/v) of dipotassium phosphate, 0.06% (w/v) of sodium dihydrogen phosphate, dodecahydrate, 0.05% (w/v) magnesium sulfate, heptahydrate, and water was placed in 500-ml Erlenmeyer flasks respectively in an amount of 100 ml, sterilized by autoclaving at 121° C. for 20 min, cooled, and then seeded with a stock culture of *Bacillus globisporus* C9 strain, FERM BP-7143, followed by culturing under rotary-shaking conditions at 27° C. and 230 rpm for 48 hours for a seed culture.

About 20 L of a fresh preparation of the same liquid culture medium as used in the above seed culture was placed in a 30-L fermentor, sterilized by heating, and then cooled to 27° C. and inoculated with 1% (v/v) of the seed culture, followed by culturing at 27° C. and a pH of 6.0 to 8.0 for 48 hours under aeration-agitation conditions. After completion of the culture, the resulting culture, which had about 0.45 unit/ml of α-isomaltosylglucosaccharide-forming enzyme activity, about 1.5 units/ml of α-isomaltosyl-transferring enzyme activity, and about 0.95 unit/ml of cyclotetrasaccharide-forming enzyme activity, was centrifuged at 10,000 rpm for 30 min to obtain about 18 L of a supernatant. When measured for enzymatic activity, the supernatant had an activity of about 0.45 unit/ml of α-isomaltosylglucosaccharide-forming enzyme, i.e., a total enzyme activity of about 8,110 units; about 1.5 units/ml of α-isomaltosyl-transferring enzyme, i.e., a total enzyme activity of about 26,900 units; and about 0.95 unit/ml of cyclotetrasaccharide-forming activity, i.e., a total enzyme activity of about 17,100 units.

The activities of these enzymes were assayed as follows: The activity of α-isomaltosylglucosaccharide-forming enzyme was assayed by dissolving maltotriose in 100 mM acetate buffer (pH 6.0) to give a concentration of 2% (w/v) for a substrate solution, adding 0.5 ml of an enzyme solution to 0.5 ml of the substrate solution, enzymatically reacting the mixture solution at 35° C. for 60 min, boiling the reaction mixture for 10 min to suspend the enzymatic reaction, and quantifying maltose, among the isomaltosyl maltose and maltose formed in the reaction mixture, on HPLC as described in Experiment 1. One unit activity of the α-isomaltosylglucosaccharide-forming enzyme was defined as the enzyme amount that forms one micromole of maltose per minute under the above enzymatic reaction conditions.

The activity of α-isomaltosyl-transferring enzyme was assayed by dissolving panose in 100 mM acetate buffer (pH 6.0) to give a concentration of 2% (w/v) for a substrate solution, adding 0.5 ml of an enzyme solution to 0.5 ml of the substrate solution, enzymatically reacting the mixture solution at 35° C. for 30 min, boiling the reaction mixture for 10 min to suspend the enzymatic reaction, and quantifying glucose, among the cyclotetrasaccharide and glucose mainly formed in the reaction mixture, by the glucose oxidase method. One unit activity of the α-isomaltosyl-transferring enzyme was defined as the enzyme amount that forms one micromole of glucose per minute under the above reaction conditions.

The cyclotetrasaccharide-forming activity was assayed by dissolving "PINE-DEX #100", a partial starch hydrolysate commercialized by Matsutani Chemical Ind., Tokyo, Japan, in 50 mM acetate buffer (pH 6.0) to give a concentration of 2% (w/v) for a substrate solution, adding 0.5 ml of an enzyme solution to 0.5 ml of the substrate solution, enzymatically reacting the mixture solution at 35° C. for 60 min, boiling the reaction mixture at 100° C. for 10 min to suspend the enzymatic reaction, and then further adding to the resulting mixture one milliliter of 50 mM acetate buffer (pH 5.0) with 70 units/ml of "TRANSGLUCOSIDASE L AMANO™", an α-glucosidase commercialized by Amano Pharmaceutical Co., Ltd., Aichi, Japan, and 27 units/ml of glucoamylase commercialized by Nagase Biochemicals, Ltd., Kyoto, Japan, incubating the mixture at 50° C. for 60 min, inactivating the remaining enzymes by heating at 100° C. for 10 min, and quantifying cyclotetrasaccharide on HPLC described in Experiment 1. One unit of cyclotetrasaccharide-forming activity was defined as the enzyme amount that forms one micromole of cyclotetrasaccharide per minute under the above enzymatic reaction conditions.

Experiment 4

Preparation of Enzyme from *Bacillus globisporus* C9 Strain

Experiment 4-1

Purification of Enzyme from *Bacillus globisporus* C9 Strain

About 18 L of the supernatant in Experiment 3 was salted out under 80% saturated ammonium sulfate and allowed to stand at 4° C. for 24 hours, and the formed sediments were collected by centrifugation at 10,000 rpm for 30 min, dissolved in 10 mM phosphate buffer (pH 7.5), and dialyzed against a fresh preparation of the same buffer to obtain about 400 ml of a crude enzyme solution with 8,110 units of the α-isomaltosylglucosaccharide-forming enzyme, 24,700 units of α-isomaltosyl-transferring enzyme, and about 15,600 units of cyclotetrasaccharide-forming activity. The crude enzyme solution was subjected to ion-exchange chromatography using 1,000 ml of "SEPABEADS FP-DA13" gel, an ion-exchange resin commercialized by Mitsubishi Chemical Industries, Ltd., Tokyo, Japan. α-Isomaltosylglucosaccharide-forming enzyme and cyclotetrasaccharide were eluted as non-adsorbed fractions without adsorbing on the gel. The resulting enzyme solution was dialyzed against 10 mM phosphate buffer (pH 7.0) with 1 M ammonium sulfate, and the dialyzed solution was centrifuged to remove impurities, and subjected to affinity chromatography using 500 ml of "SEPHACRYL HR S-200", a gel commercialized by Amersham Corp., Div. Amersham International, Arlington Heights, Ill., USA. Enzymatically active components adsorbed on the gel and, when sequentially eluted with a linear gradient decreasing from 1 M to 0 M of ammonium sulfate and a linear gradient increasing from 0 mM to 100 mM of maltotetraose, α-isomaltosylglucosaccharide-forming enzyme and α-isomaltosyl-transferring enzyme were separately eluted, i.e., the former was eluted with the linear gradient of maltotetraose at about 30 mM and the latter was eluted with the linear gradient of ammonium sulfate at about 0 M. Fractions with α-isomaltosyl-transferring activity and those with α-isomaltosylglucosaccharide-forming activity were separatory collected. No cyclotetrasaccharide-forming activity was found in any of the above fractions and this revealed that a mixture solution of both of the above fractions with α-isomaltosylglucosaccharide-forming enzyme and α-isomaltosyl-transferring enzyme exhibited cyclotetrasaccharide-forming activity, showing that the activity of forming cyclotetrasaccharide from partial starch hydrolyzates was exerted by the coaction of the activities of the above two types of enzymes.

Methods for separatory purifying α-isomaltosylglucosaccharide-forming enzyme and α-isomaltosyl-transferring enzyme are explained below:

Experiment 4-2

Purification of α-Isomaltosylglucosaccharide-Forming Enzyme

A fraction of the α-isomaltosylglucosaccharide-forming enzyme, obtained in Experiment 4-1, was dialyzed against 10 mM phosphate buffer (pH 7.0) with 1 M ammonium sulfate. The dialyzed solution was centrifuged to remove insoluble substances, and the resulting supernatant was fed to hydrophobic chromatography using 350 ml of "BUTYL-TOYOPEARL 650 M", a gel commercialized by Tosoh Corporation, Tokyo, Japan. The enzyme adsorbed on the gel and was eluted therefrom at about 0.3 M ammonium sulfate with a linear gradient decreasing from 1 M to 0 M of ammonium sulfate, followed by collecting fractions with the enzyme activity. The fractions were pooled and dialyzed against 10 mM phosphate buffer (pH 7.0) with 1 M ammonium sulfate. The resulting dialyzed solution was centrifuged to remove insoluble substances and fed to affinity chromatography using "SEPHACRYL HR S-200" gel to purify the enzyme. The amount of enzyme activity, the specific activity, and the yield of the α-isomaltosylglucosaccharide-forming enzyme in each purification step are in Table 1.

TABLE 1

| Purification step | Enzyme* activity (unit) | Specific activity of enzyme* (unit/mg protein) | Yield (%) |
|---|---|---|---|
| Culture supernatant | 8,110 | 0.12 | 100 |
| Dialyzed solution after salting out with ammonium sulfate | 7,450 | 0.56 | 91.9 |
| Eluate from ion-exchange column chromatography | 5,850 | 1.03 | 72.1 |
| Eluate from affinity column chromatography | 4,040 | 8.72 | 49.8 |
| Eluate from hydrophobic column chromatography | 3,070 | 10.6 | 37.8 |
| Eluate from affinity column chromatography | 1,870 | 13.6 | 23.1 |

Note:
The symbol "*" means α-isomaltosylglucosaccharide-forming enzyme.

The finally purified α-isomaltosylglucosaccharide-forming enzyme specimen was assayed for purity on gel electrophoresis using a 7.5% (w/v) polyacrylamide gel and detected on the gel as a single protein band, meaning a high purity enzyme specimen.

Experiment 4-3

Purification of α-Isomaltosyl-Transferring Enzyme

A fraction with α-isomaltosyl-transferring enzyme, which had been separated from a fraction with α-isomaltosylglucosaccharide-forming enzyme by affinity chromatography in Experiment 4-1, was dialyzed against 10 mM phosphate buffer (pH 7.0) with 1 M ammonium sulfate. The resulting dialyzed solution was centrifuged to remove insoluble substances and subjected to affinity chromatography using 350 ml of "BUTYL-TOYOPEARL 650 M", a gel commercialized by Tosoh Corporation, Tokyo, Japan. The enzyme adsorbed on the gel and was eluted therefrom at about 0.3 M ammonium sulfate with a linear gradient decreasing from 1 M to 0 M of ammonium sulfate, followed by collecting fractions with the enzyme activity. The fractions were pooled and dialyzed against 10 mM phosphate buffer (pH 7.0) with 1 M ammonium sulfate. The resulting dialyzed solution was centrifuged to remove insoluble substances and fed to affinity chromatography using "SEPHACRYL HR S-200" gel to purify the enzyme. The amount of enzyme activity, the specific activity, and the yield of α-isomaltosyl-transferring enzyme in each purification step are in Table 2.

TABLE 2

| Purification step | Enzyme* activity (unit) | Specific activity of enzyme* (unit/mg protein) | Yield (%) |
|---|---|---|---|
| Culture supernatant | 26,900 | 0.41 | 100 |
| Dialyzed solution after salting out with ammonium sulfate | 24,700 | 1.85 | 91.8 |
| Eluate from ion-exchange column chromatography | 19,400 | 3.41 | 72.1 |
| Eluate from affinity column chromatography | 13,400 | 18.6 | 49.8 |
| Eluate from hydrophobic column chromatography | 10,000 | 21.3 | 37.2 |
| Eluate from affinity column chromatography | 6,460 | 26.9 | 24.0 |

Note:
The symbol "*" means α-isomaltosyl-transferring enzyme.

Experiment 5

Property of α-Isomaltosylglucosaccharide-Forming Enzyme and α-Isomaltosyl-Transferring Enzyme Experiment 5-1

Property of α-Isomaltosylglucosaccharide-Forming Enzyme

A purified specimen of α-isomaltosylglucosaccharide-forming enzyme, obtained by the method in Experiment 4-2, was subjected to SDS-PAGE using a 7.5% (w/v) of polyacrylamide gel and then determined for molecular weight in comparison with the dynamics of standard molecular markers electrophoresed in parallel, commercialized by Bio-Rad Laboratories Inc., Brussels, Belgium, revealing that the enzyme had a molecular weight of about 140,000±20,000 daltons.

A fresh preparation of the above purified specimen was subjected to isoelectrophoresis using a gel containing 2% (w/v) ampholine commercialized by Amersham Corp., Div. Amersham International, Arlington Heights, Ill., USA, and then measured for pHs of protein bands and gel to determine the isoelectric point of the enzyme, revealing that the enzyme had an isoelectric point of about 5.2±0.5.

Figure 5:
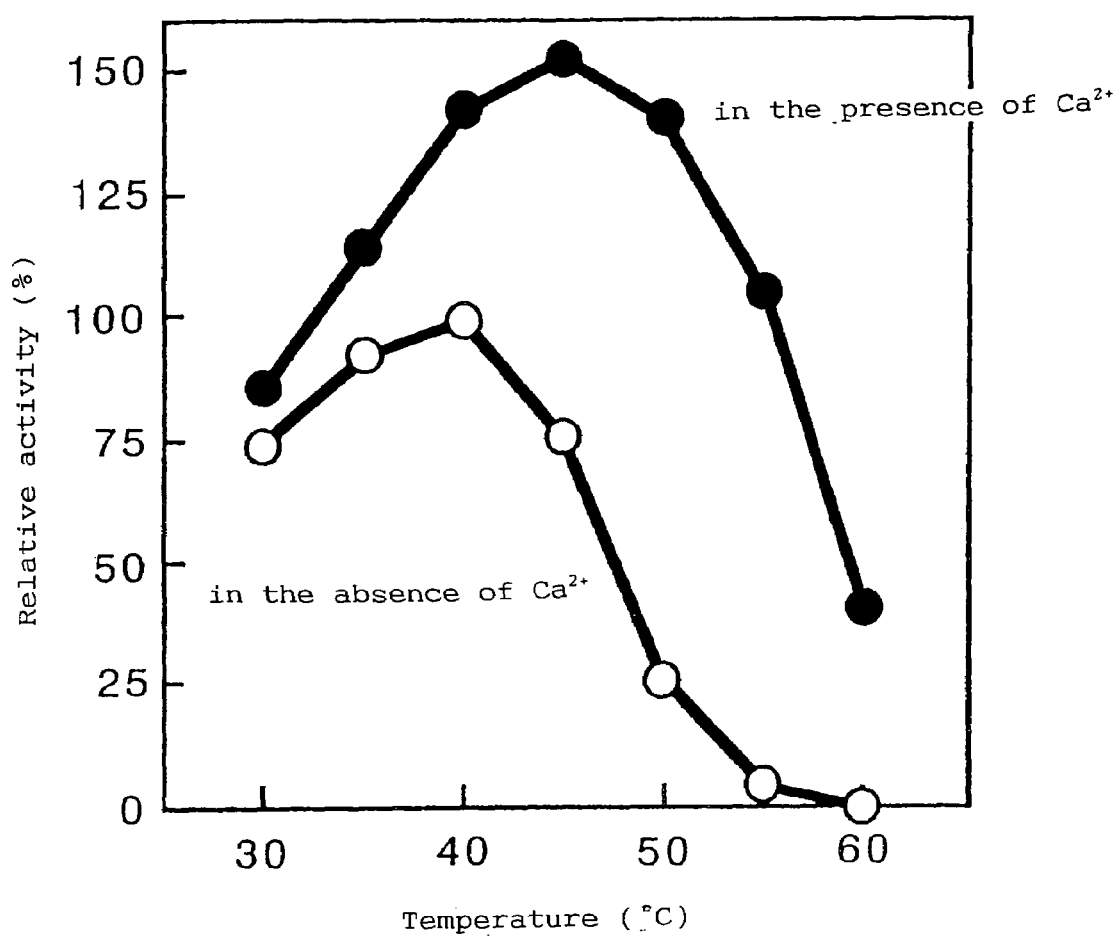
FIG. 5 shows the thermal influence on the enzymatic activity of α-isomaltosylglucosaccharide-forming enzyme from a microorganism of the species *Bacillus globisporus* C9 strain.
Figure 6:
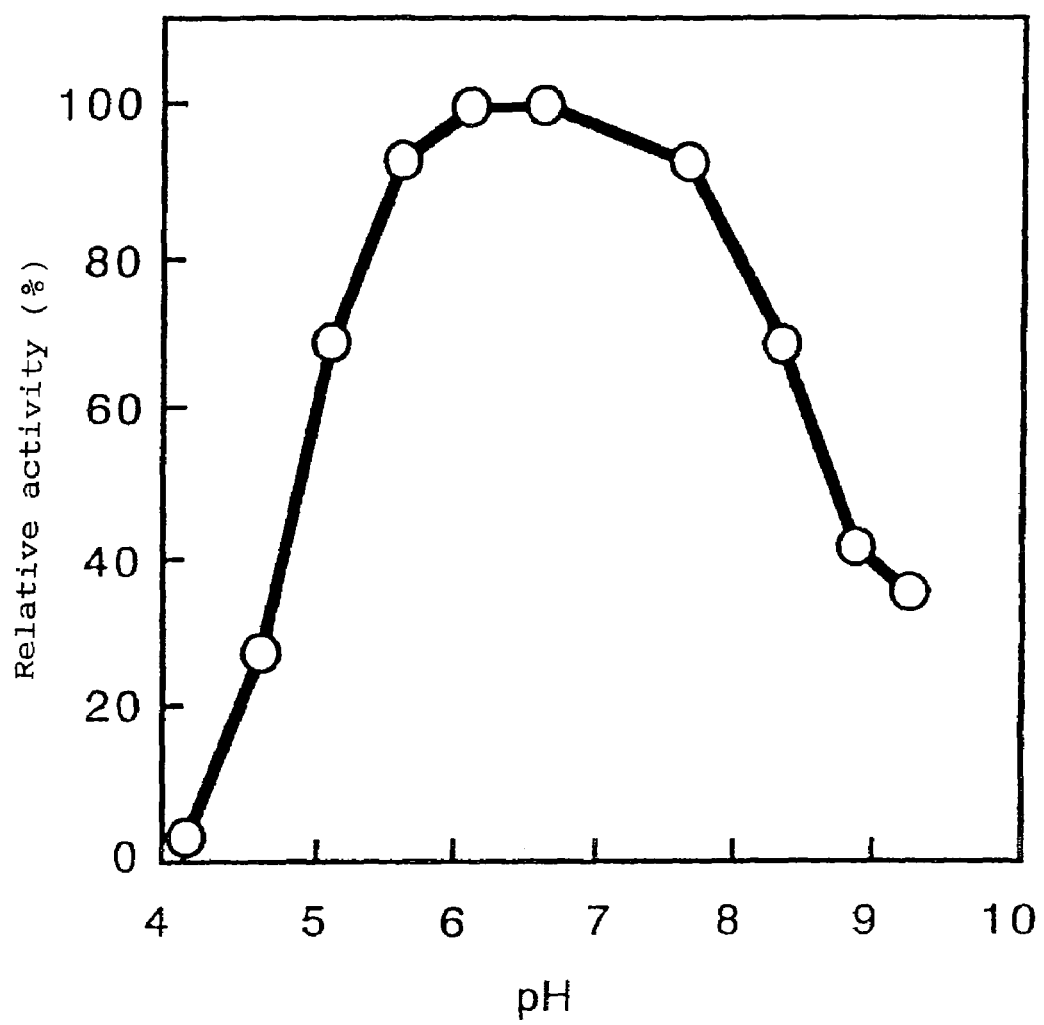
FIG. 6 shows the pH influence on the enzymatic activity of α-isomaltosylglucosaccharide-forming enzyme from a microorganism of the species *Bacillus globisporus* C9 strain.
Figure 7:
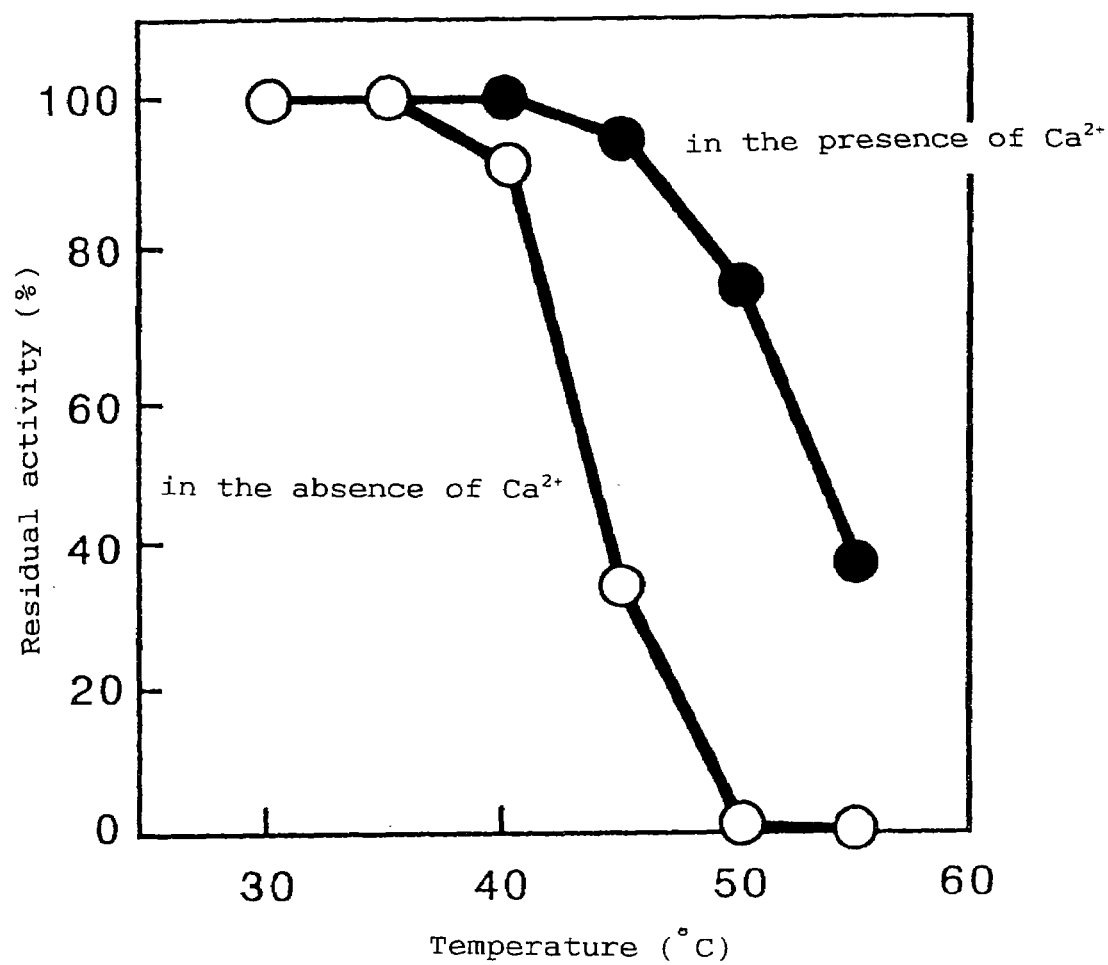
FIG. 7 shows the thermal stability of α-isomaltosylglucosaccharide-forming enzyme from a microorganism of the species *Bacillus globisporus* C9 strain.
Figure 8:
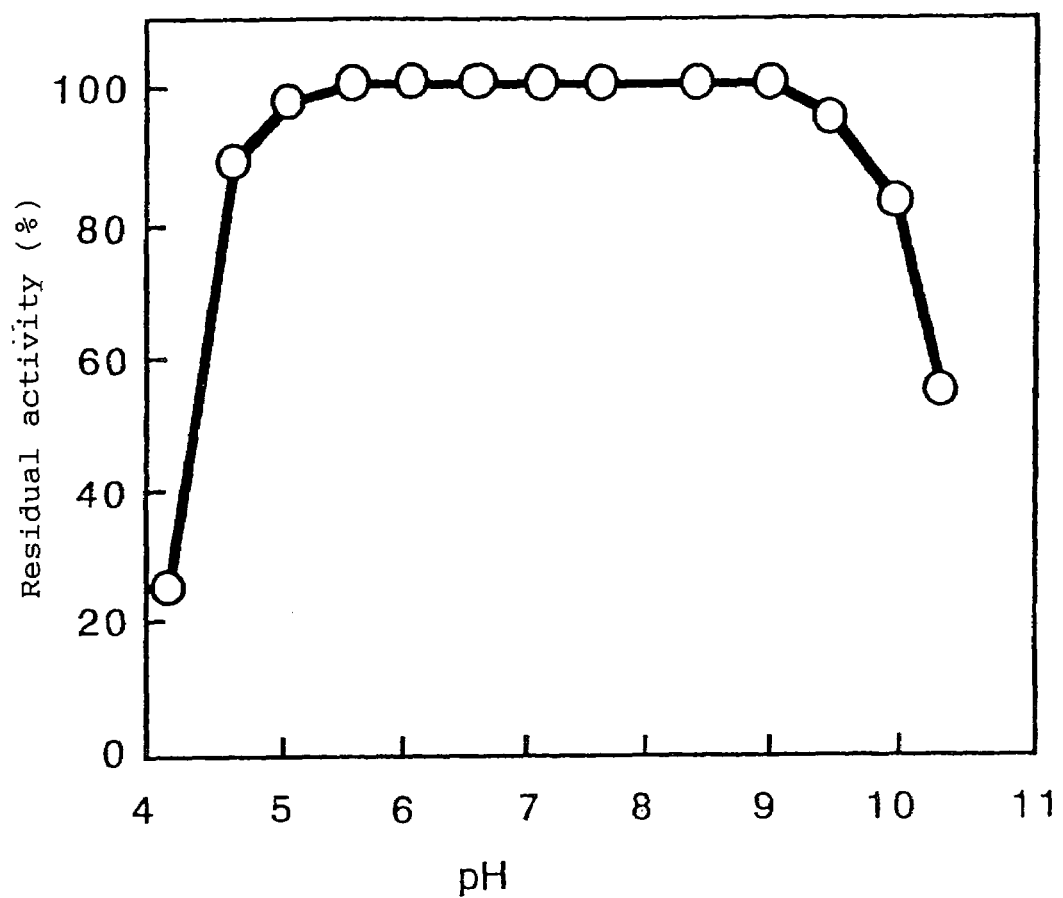
FIG. 8 shows the pH stability of α-isomaltosylglucosaccharide-forming enzyme from a microorganism of the species *Bacillus globisporus* C9 strain.

The influence of temperature and pH on the activity of α-isomaltosylglucosaccharide-forming enzyme was examined in accordance with the assay for the enzyme activity, where the influence of temperature was conducted in the presence or absence of 1 mM $Ca^{2+}$. These results are in FIG. 5 (influence of temperature) and FIG. 6 (influence of pH). The optimum temperature of the enzyme was about 40° C. (in the absence of $Ca^{2+}$) and about 45° C. (in the presence of 1 mM $Ca^{2+}$) when incubated at pH 6.0 for 60 min, and the optimum pH of the enzyme was about 6.0 to about 6.5 when incubated at 35° C. for 60 min. The thermal stability of the enzyme was determined by incubating it in 20 mM acetate buffers (pH 6.0) at prescribed temperatures for 60 min in the presence or absence of 1 mM $Ca^{2+}$, cooling the resulting enzyme solutions with water, and assaying the remaining enzyme activity for each solution. The pH stability of the enzyme was determined by keeping it in 50 mM buffers having prescribed pHs at 4° C. for 24 hours, adjusting the pH of each solution to 6.0, and assaying the remaining enzyme activity for each solution. These results are respectively in FIG. 7 (thermal stability) and FIG. 8 (pH stability). As a result, the enzyme was thermally stable up to about 35° C. in the absence of $Ca^{2+}$ and about 40° C. in the presence of 1 mM $Ca^{2+}$, and was stable at pHs from about 4.5 to about 9.0.

The influence of metal ions on the activity of α-isomaltosylglucosaccharide-forming enzyme was examined in the presence of 1 mM of any of metal salts according to the assay for the enzyme activity. The results are in Table 3.

TABLE 3

| Metal ion | Relative activity (%) | Metal ion | Relative activity (%) |
|---|---|---|---|
| None | 100 | $Hg^{2+}$ | 4 |
| $Zn^{2+}$ | 92 | $Ba^{2+}$ | 65 |
| $Mg^{2+}$ | 100 | $Sr^{2+}$ | 80 |
| $Ca^{2+}$ | 115 | $Pb^{2+}$ | 103 |
| $Co^{2+}$ | 100 | $Fe^{2+}$ | 98 |
| $Cu^{2+}$ | 15 | $Fe^{3+}$ | 97 |
| $Ni^{2+}$ | 98 | $Mn^{2+}$ | 111 |
| $Al^{3+}$ | 99 | EDTA | 20 |

As evident form the results in Table 3, the enzyme activity was significantly inhibited by $Hg^{2+}$, $Cu^{2+}$, and EDTA, and was also inhibited by $Ba^{2+}$ and $Sr^{2+}$. It was also found that the enzyme was activated by $Ca^{2+}$ and $Mn^{2+}$.

Amino acid analysis of the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ ID NO:1, i.e., tyrosine-valine-serine-serine-leucine-glycine-asparagine-leucine-isoleucine in the N-terminal region.

Experiment 5-2

Property of α-Isomaltosyl-Transferring Enzyme

A purified specimen of α-isomaltosyl-transferring enzyme, obtained by the method in Experiment 4-3, was subjected to SDS-PAGE using a 7.5% (w/v) of polyacrylamide gel and then determined for molecular weight in comparison with the dynamics of standard molecular markers electrophoresed in parallel, commercialized by Bio-Rad Laboratories Inc., Brussels, Belgium, revealing that the enzyme had a molecular weight of about 112,000±20,000 daltons.

A fresh preparation of the above purified specimen was subjected to isoelectrophoresis using a gel containing 2% (w/v) ampholine commercialized by Amersham Corp., Div. Amersham International, Arlington Heights, Ill., USA, and then measured for pHs of protein bands and gel to determine the isoelectric point of the enzyme, revealing that the enzyme had an isoelectric point of about 5.5±0.5.

Figure 9:
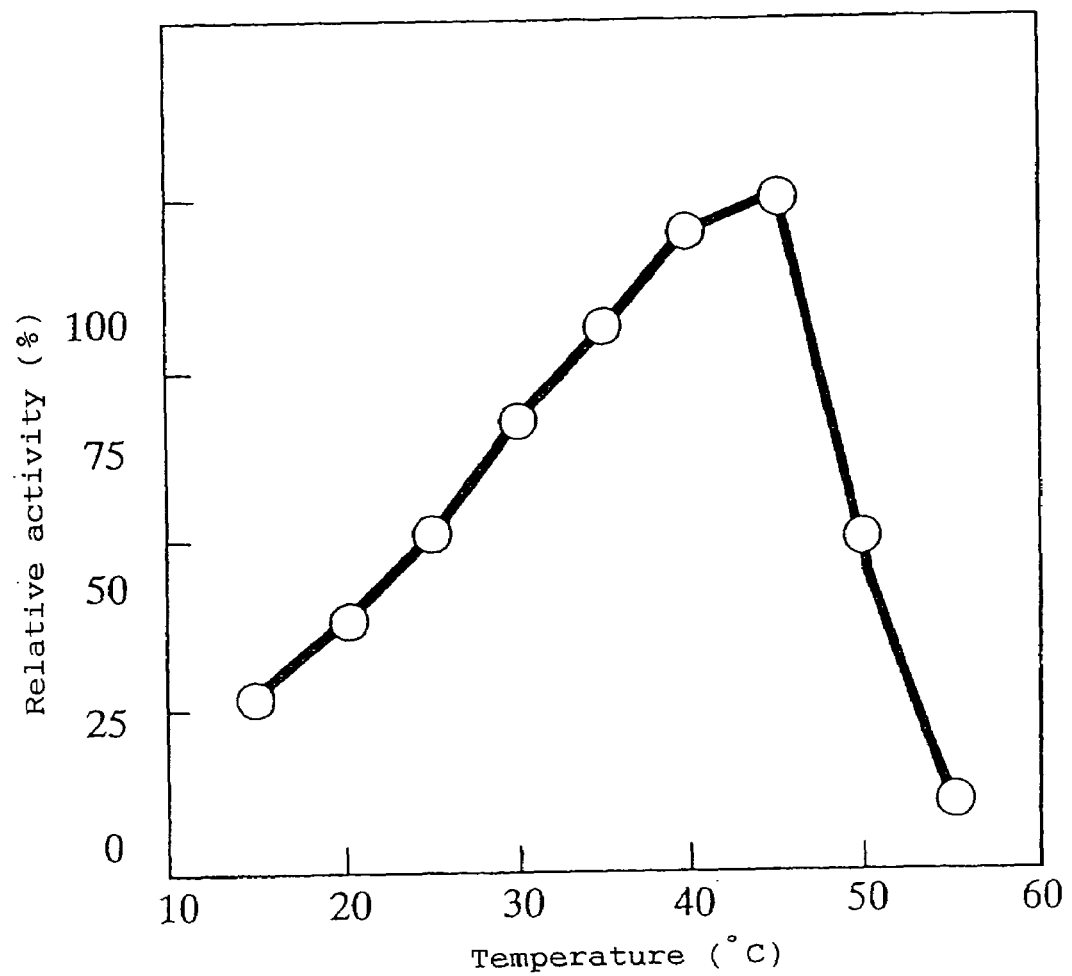
FIG. 9 shows the thermal influence on the enzymatic activity of α-isomaltosyl-transferring enzyme from a microorganism of the species *Bacillus globisporus* C9 strain.
Figure 10:
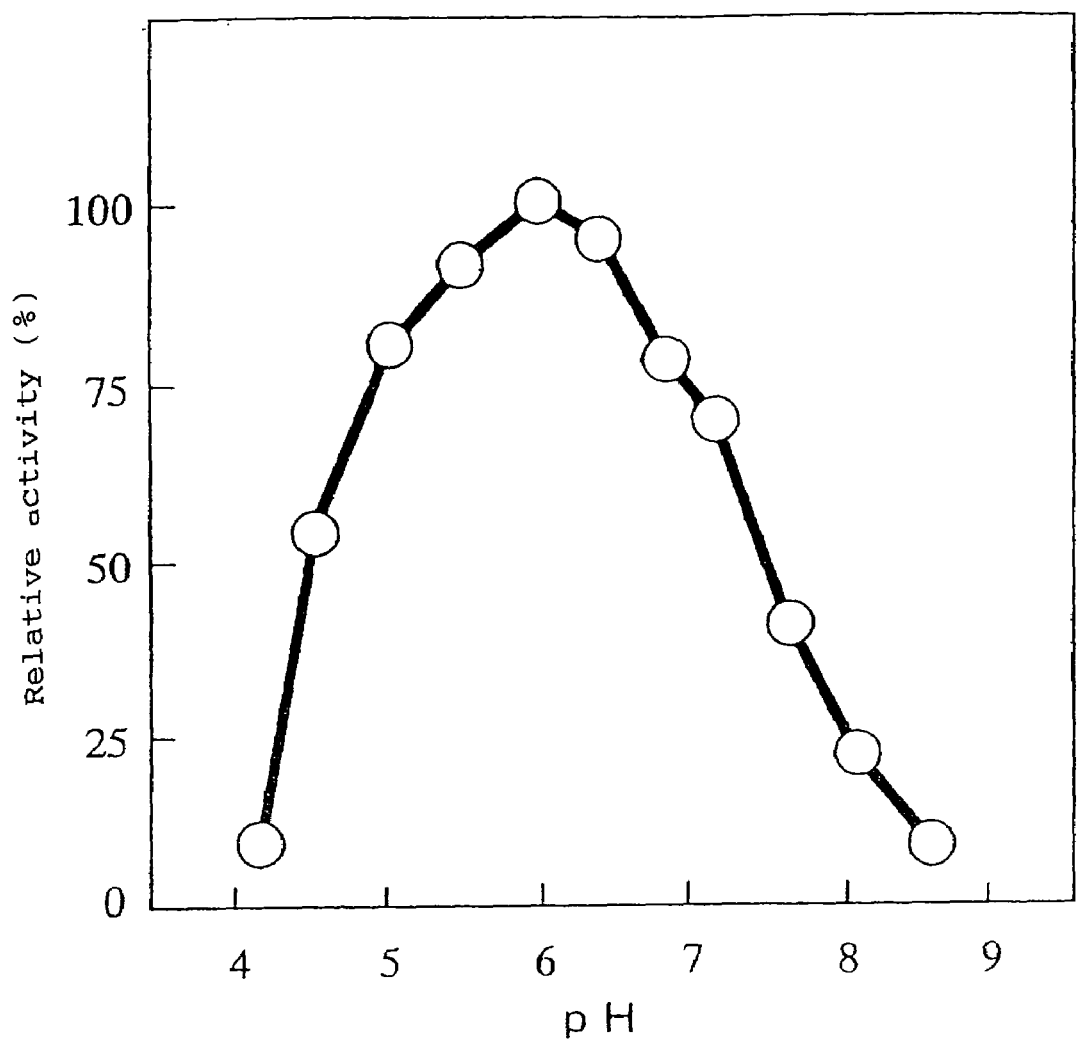
FIG. 10 shows the pH influence on the enzymatic activity of α-isomaltosyl-transferring enzyme from a microorganism of the species *Bacillus globisporus* C9 strain.
Figure 11:
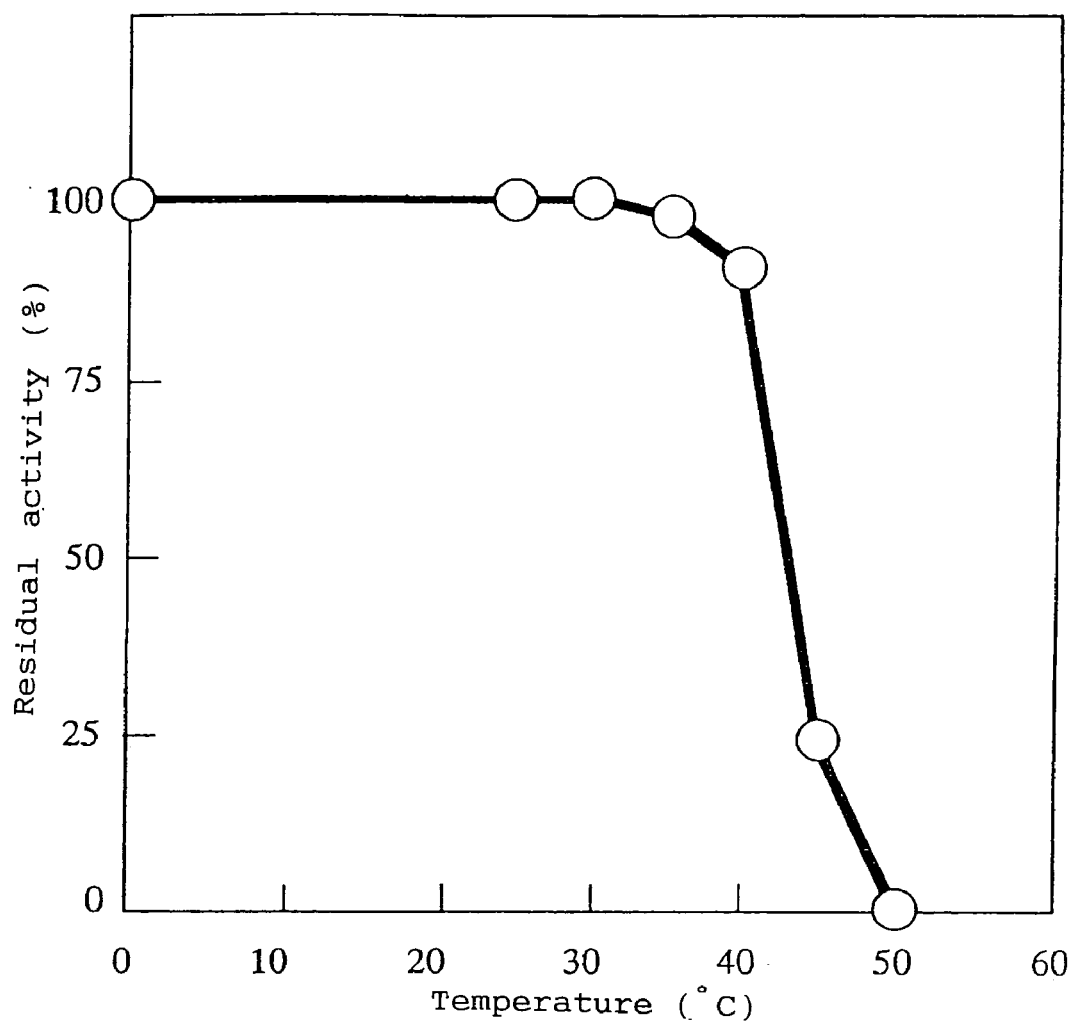
FIG. 11 shows the thermal stability of α-isomaltosyl-transferring enzyme from a microorganism of the species *Bacillus globisporus* C9 strain.
Figure 12:
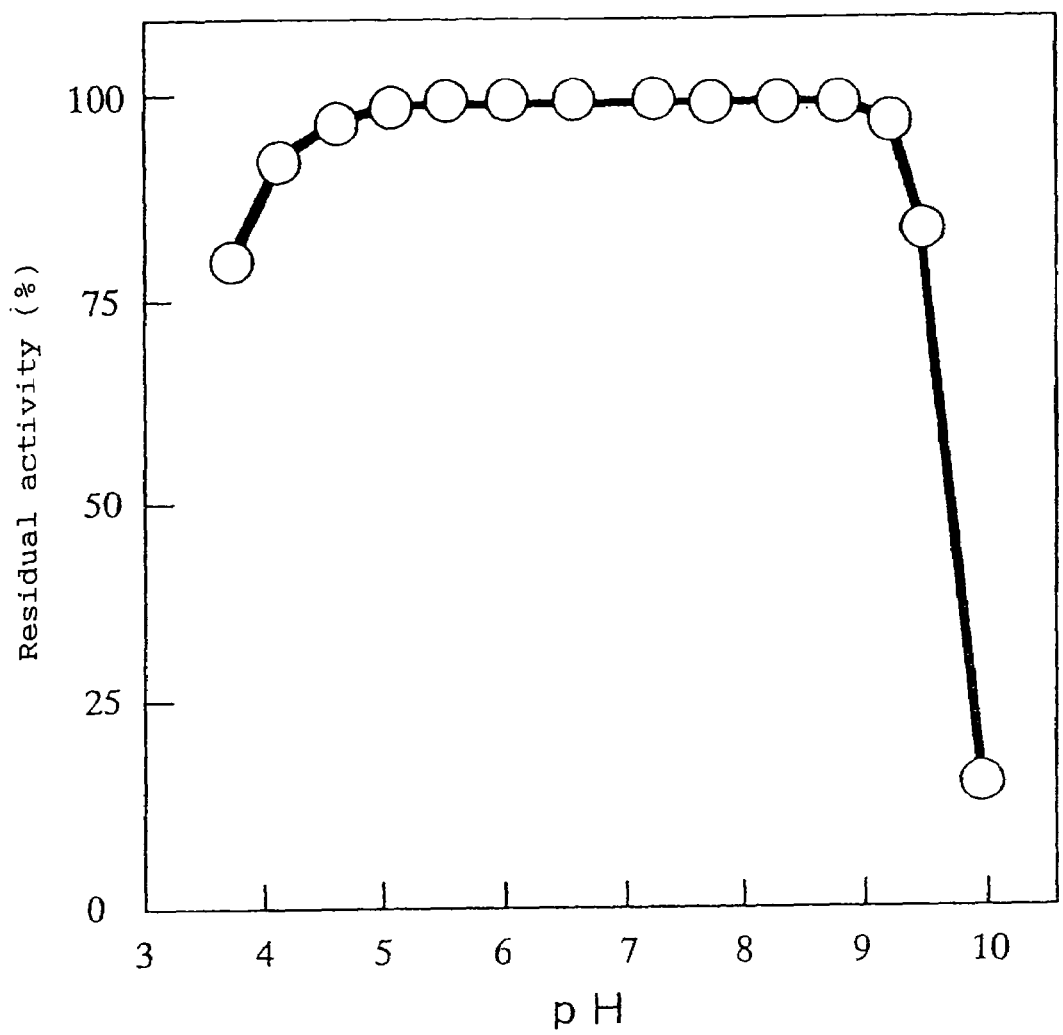
FIG. 12 shows the pH stability of α-isomaltosyl-transferring enzyme from a microorganism of the species *Bacillus globisporus* C9 strain.

The influence of temperature and pH on the activity of α-isomaltosyl-transferring enzyme was examined in accordance with the assay for the enzyme activity. These results are respectively in FIG. 9 (influence of temperature) and FIG. 10 (influence of pH). The optimum temperature of the enzyme was about 45° C. when incubated at pH 6.0 for 30 min, and the optimum pH of the enzyme was about 6.0 when incubated at 35° C. for 30 min. The thermal stability of the enzyme was determined by incubating it in 20 mM acetate buffers (pH 6.0) at prescribed temperatures for 60 min, cooling the resulting enzyme solutions with water, and assaying the remaining enzyme activity of each solution. The pH stability of the enzyme was determined by keeping it in 50 mM buffers having prescribed pHs at 4° C. for 24 hours, adjusting the pH of each solution to 6.0, and assaying the remaining enzyme activity for each solution. These results are respectively in FIG. 11 (thermal stability) and FIG. 12 (pH stability). As a result, the enzyme was thermally stable up to about 40° C. and was stable at pHs of about 4.0 to about 9.0.

The influence of metal ions on the activity of α-isomaltosyl-transferring enzyme was examined in the presence of 1 mM of any of metal salts according to the assay for the enzyme activity. The results are in Table 4.

TABLE 4

| Metal ion | Relative activity (%) | Metal ion | Relative activity (%) |
|---|---|---|---|
| None | 100 | $Hg^{2+}$ | 1 |
| $Zn^{2+}$ | 88 | $Ba^{2+}$ | 102 |
| $Mg^{2+}$ | 98 | $Sr^{2+}$ | 101 |
| $Ca^{2+}$ | 101 | $Pb^{2+}$ | 89 |
| $Co^{2+}$ | 103 | $Fe^{2+}$ | 96 |
| $Cu^{2+}$ | 57 | $Fe^{3+}$ | 105 |
| $Ni^{2+}$ | 102 | $Mn^{2+}$ | 106 |
| $Al^{3+}$ | 103 | EDTA | 104 |

As evident form the results in Table 4, the enzyme activity was significantly inhibited by $Hg^{2+}$ and was also inhibited by $Cu^{2+}$. It was also found that the enzyme was not activated by $Ca^{2+}$ and not inhibited by EDTA.

Amino acid analysis of the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ ID NO:2, i.e, isoleucine-aspartic acid-glycine-valine-tyrosine-histidine-alanine-proline-asparagine-glycine in the N-terminal region.

Experiment 6

Production of α-Isomaltosylglucosaccharide-Forming Enzyme from Bacillus globisporus C11 Strain A liquid nutrient culture medium, consisting of 4.0% (w/v) of "PINE-DEX #4", a partial starch hydrolysate, 1.8% (w/v) of "ASAHIMEAST", a yeast extract, 0.1% (w/v) of dipotassium phosphate, 0.06% (w/v) of sodium dihydrogen phosphate, dodecahydrate, 0.05% (w/v) magnesium sulfate, heptahydrate, and water was placed in 500-ml Erlenmeyer flasks respectively in an amount of 100 ml, autoclaved at 121° C. for 20 minutes to effect sterilization, cooled, inoculated with a stock culture of Bacillus globisporus C11 strain, FERM BP-7144, and incubated at 27° C. for 48 hours under rotary shaking conditions of 230 rpm. The resulting cultures were pooled and used as a seed culture.

About 20 L of a fresh preparation of the same nutrient culture medium as used in the above culture was placed in a 30-L fermentor, sterilized by heating, cooled to 27° C., inoculated with 1% (v/v) of the seed culture, and incubated for about 48 hours while stirring under aeration agitation conditions at 27° C. and pH 6.0 to 8.0. The resultant culture, having about 0.55 unit/ml of α-isomaltosylglucosaccharide-forming enzyme activity, about 1.8 units/ml of α-isomaltosyl-transferring enzyme activity, and about 1.1 units/ml of cyclotetrasaccharide-forming enzyme activity, was centrifuged at 10,000 rpm for 30 min to obtain about 18 L of a supernatant. Measurement of the supernatant revealed that it had about 0.51 unit/ml of α-isomaltosylglucosaccharide-forming enzyme activity, i.e., a total enzyme activity of about 9,180 units; about 1.7 units/ml of α-isomaltosyl-transferring enzyme activity, i.e., a total enzyme activity of about 30,400 units; and about 1.1 units/ml of cyclotetrasaccharide-forming enzyme activity, i.e., a total enzyme activity of about 19,400 units.

Experiment 7

Preparation of Enzyme from Bacillus globisporus C11 Strain

An 18 L of the supernatant obtained in Experiment 6 was salted out with an 80% saturated ammonium sulfate solution and allowed to stand at 4° C. for 24 hours. Then the salted out sediments were collected by centrifugation at 10,000 for 30 min, dissolved in 10 mM phosphate buffer (pH 7.5), dialyzed against a fresh preparation of the same buffer to obtain about 416 ml of a crude enzyme solution. The crude enzyme solution was revealed to have 8,440 units of the α-isomaltosylglucosaccharide-forming enzyme, about 28,000 units of α-isomaltosyl-transferring enzyme, and about 17,700 units of cyclotetrasaccharide-forming enzyme. When subjected to ion-exchange chromatography using "SEPABEADS FP-DA13" gel, disclosed in Experiment 4-1, any of the above three types of enzymes were eluted as non-adsorbed fractions without adsorbing on the gel. The non-adsorbed fractions with these enzymes were pooled and dialyzed against 10 mM phosphate buffer (pH 7.0) containing 1 M ammonium sulfate, and the dialyzed solution was centrifuged to remove insoluble substances. The resulting supernatant was fed to affinity chromatography using 500 ml of "SEPHACRYL HR S-200" gel to purify the enzymes. Active enzymes were adsorbed on the gel and sequentially eluted therefrom with a linear gradient decreasing from 1 M to 0 M of ammonium sulfate and a linear gradient increasing from 0 mM to 100 mM of maltotetraose, resulting in a separate elution of α-isomaltosyl-transferring enzyme or α-isomaltosylglucosaccharide-forming enzyme, where the former enzyme was eluted with the linear gradient of ammonium sulfate at a concentration of about 0.3 M and the latter enzyme was eluted with a linear gradient of maltotetraose at a concentration of about 30 mM. Then the fractions with α-isomaltosyl-transferring enzyme and those with α-isomaltosylglucosaccharide-forming enzyme were separately collected and recovered. Similarly as in the case of Bacillus globisporus C9 strain in Experiment 4, it was found that no cyclotetrasaccharide-forming activity was found in any fraction in this column chromatography, and that an enzyme mixture solution of both fractions of α-isomaltosyl-transferring enzyme and α-isomaltosylglucosaccharide-forming enzyme showed cyclotetrasaccharide-forming activity, revealing that the activity of forming cyclotetrasaccharide from partial starch hydrolyzates was exerted in collaboration with the enzyme activities of the two types of enzymes.

Methods for separately purifying α-isomaltosylglucosaccharide-forming enzyme and α-isomaltosyl-transferring enzyme are explained below:

Experiment 7-2

Purification of α-Isomaltosylglucosaccharide-Forming Enzyme

A fraction of α-isomaltosylglucosaccharide-forming enzyme was dialyzed against 10 mM phosphate buffer (pH 7.0) containing 1 M ammonium sulfate. The dialyzed solution was centrifuged to remove insoluble substances, and the resulting supernatant was fed to hydrophobic chromatography using 350 ml of "BUTYL-TOYOPEARL 650 M", a gel commercialized by Tosoh Corporation, Tokyo, Japan. The enzyme adsorbed on the gel was eluted therefrom at about 0.3 M ammonium sulfate with a linear gradient decreasing from 1 M to 0 M of ammonium sulfate, followed by collecting fractions with the enzyme activity. The fractions were pooled and dialyzed against 10 mM phosphate buffer (pH 7.0) containing 1 M ammonium sulfate. The resulting dialyzed solution was centrifuged to remove insoluble substances and fed to affinity chromatography using "SEPHACRYL HR S-200" gel to purify the enzyme. The amount of enzyme activity, the specific activity, and the yield of α-isomaltosylglucosaccharide-forming enzyme in each purification step are in Table 5.

TABLE 5

| Purification step | Enzyme* activity (unit) | Specific activity of enzyme* (unit/mg protein) | Yield (%) |
|---|---|---|---|
| Culture supernatant | 9,180 | 0.14 | 100 |
| Dialyzed solution after salting out with ammonium sulfate | 8,440 | 0.60 | 91.9 |
| Eluate from ion-exchange column chromatography | 6,620 | 1.08 | 72.1 |
| Eluate from affinity column chromatography | 4,130 | 8.83 | 45.0 |
| Eluate from hydrophobic column chromatography | 3,310 | 11.0 | 36.1 |
| Eluate from affinity column chromatography | 2,000 | 13.4 | 21.8 |

Note:
The symbol "*" means α-isomaltosylglucosaccharide-forming enzyme.

The finally purified α-isomaltosylglucosaccharide-forming enzyme specimen was assayed for purity on gel electrophoresis using a 7.5% (w/v) polyacrylamide gel and detected on the gel as a single protein band, meaning a high purity enzyme specimen.

Experiment 7-3

Purification of α-Isomaltosyl-Transferring Enzyme

A fraction of α-isomaltosyl-transferring enzyme, which had been separated from a fraction with α-isomaltosylglucosaccharide-forming enzyme by the affinity chromatography in Experiment 7-1, was dialyzed against 10 mM phosphate buffer (pH 7.0) containing 1 M ammonium sulfate. The dialyzed solution was centrifuged to remove insoluble substances, and the resulting supernatant was fed to hydrophobic chromatography using 350 ml of "BUTYL-TOYO-PEARL 650 M", a gel commercialized by Tosoh Corporation, Tokyo, Japan. The enzyme adsorbed on the gel and was eluted therefrom at about 0.3 M ammonium sulfate with a linear gradient decreasing from 1 M to 0 M of ammonium sulfate, followed by collecting fractions with the enzyme activity. The fractions were pooled and dialyzed against 10 mM phosphate buffer (pH 7.0) containing 1 M ammonium sulfate. The resulting dialyzed solution was centrifuged to remove insoluble substances and fed to affinity chromatography using "SEPHACRYL HR S-200" gel to purify the enzyme. The amount of enzyme activity, the specific activity, and the yield of the α-isomaltosyl-transferring enzyme in each purification step are in Table 6.

TABLE 6

| Purification step | Enzyme* activity (unit) | Specific activity of enzyme* (unit/mg protein) | Yield (%) |
|---|---|---|---|
| Culture supernatant | 30,400 | 0.45 | 100 |
| Dialyzed solution after salting out with ammonium sulfate | 28,000 | 1.98 | 92.1 |
| Eluate from ion-exchange column chromatography | 21,800 | 3.56 | 71.7 |

TABLE 6-continued

| Purification step | Enzyme* activity (unit) | Specific activity of enzyme* (unit/mg protein) | Yield (%) |
|---|---|---|---|
| Eluate from affinity column chromatography | 13,700 | 21.9 | 45.1 |
| Eluate from hydrophobic column chromatography | 10,300 | 23.4 | 33.9 |
| Eluate from affinity column chromatography | 5,510 | 29.6 | 18.1 |

Note:
The symbol "*" means α-isomaltosyl-transferring enzyme.

Experiment 8

Preparation of α-Isomaltosylglucosaccharide-Forming Enzyme

Experiment 8-1

Property of α-Isomaltosylglucosaccharide-Forming Enzyme

A purified specimen of α-isomaltosylglucosaccharide-forming enzyme, obtained by the method in Experiment 7-2, was subjected to SDS-PAGE using a 7.5% (w/v) of polyacrylamide gel and then determined for molecular weight in comparison with the dynamics of standard molecular markers electrophoresed in parallel, commercialized by Bio-Rad Laboratories Inc., Brussels, Belgium, revealing that the enzyme had a molecular weight of about 137,000±20,000 daltons.

A fresh preparation of the above purified specimen was subjected to isoelectrophoresis using a gel containing 2% (w/v) ampholine commercialized by Amersham Corp., Div. Amersham International, Arlington Heights, Ill., USA, and then measured for pHs of protein bands and gel to determine the isoelectric point of the enzyme, revealing that the enzyme had an isoelectric point of about 5.2±0.5.

Figure 13:
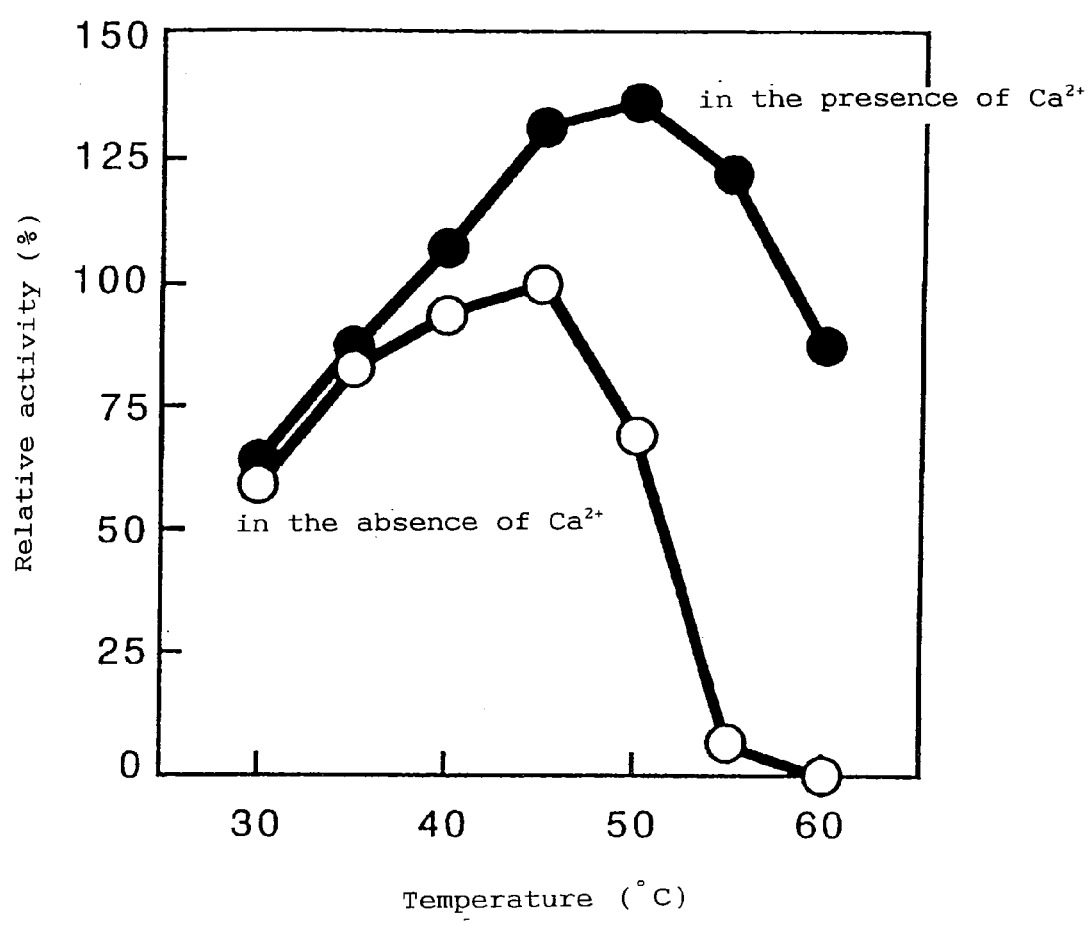
FIG. 13 shows the thermal influence on the enzymatic activity of α-isomaltosylglucosaccharide-forming enzyme from a microorganism of the species *Bacillus globisporus* C11 strain.
Figure 14:
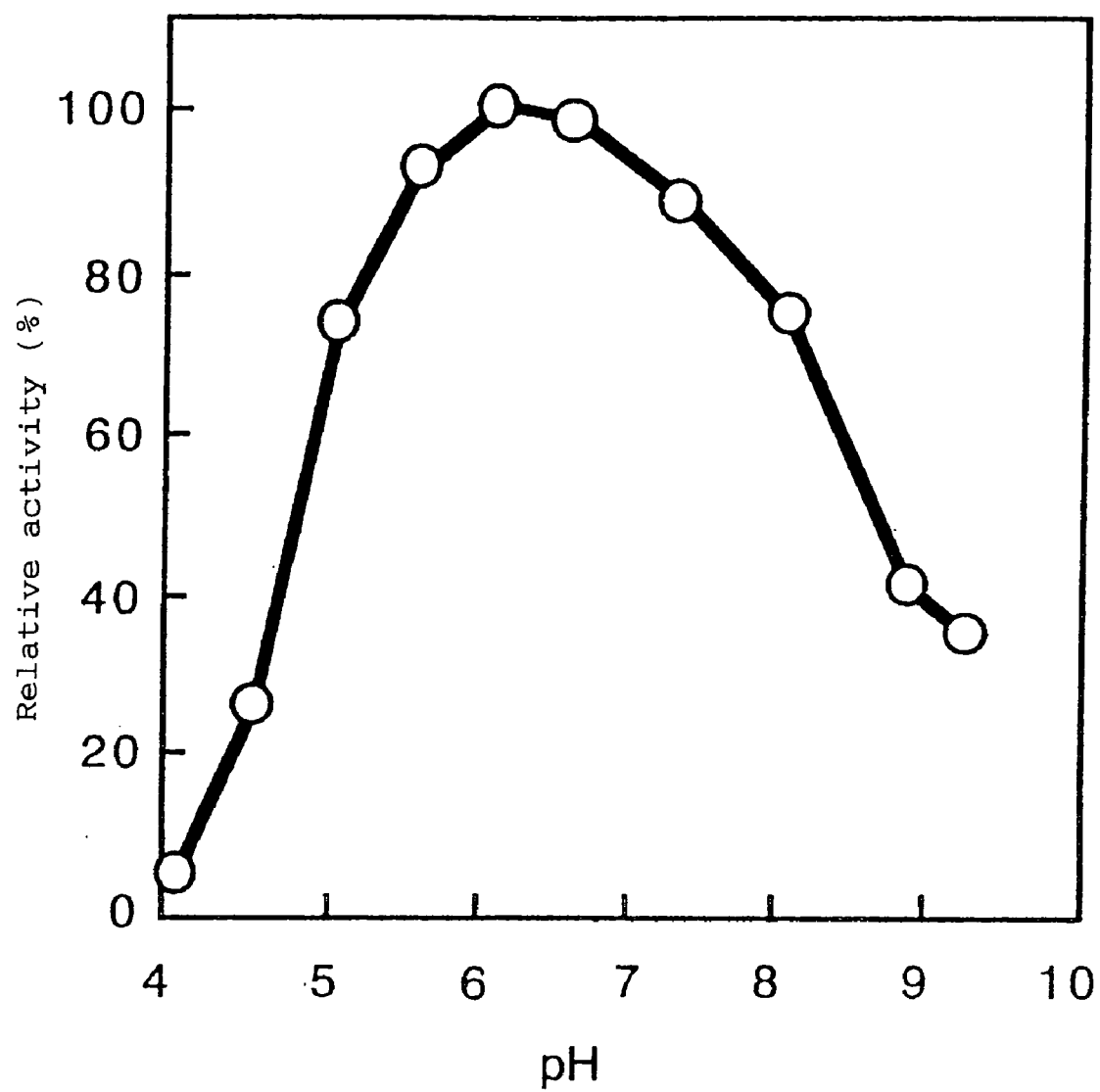
FIG. 14 shows the pH influence on α-isomaltosylglucosaccharide-forming enzyme from a microorganism of the species *Bacillus globisporus* C11 strain.
Figure 15:
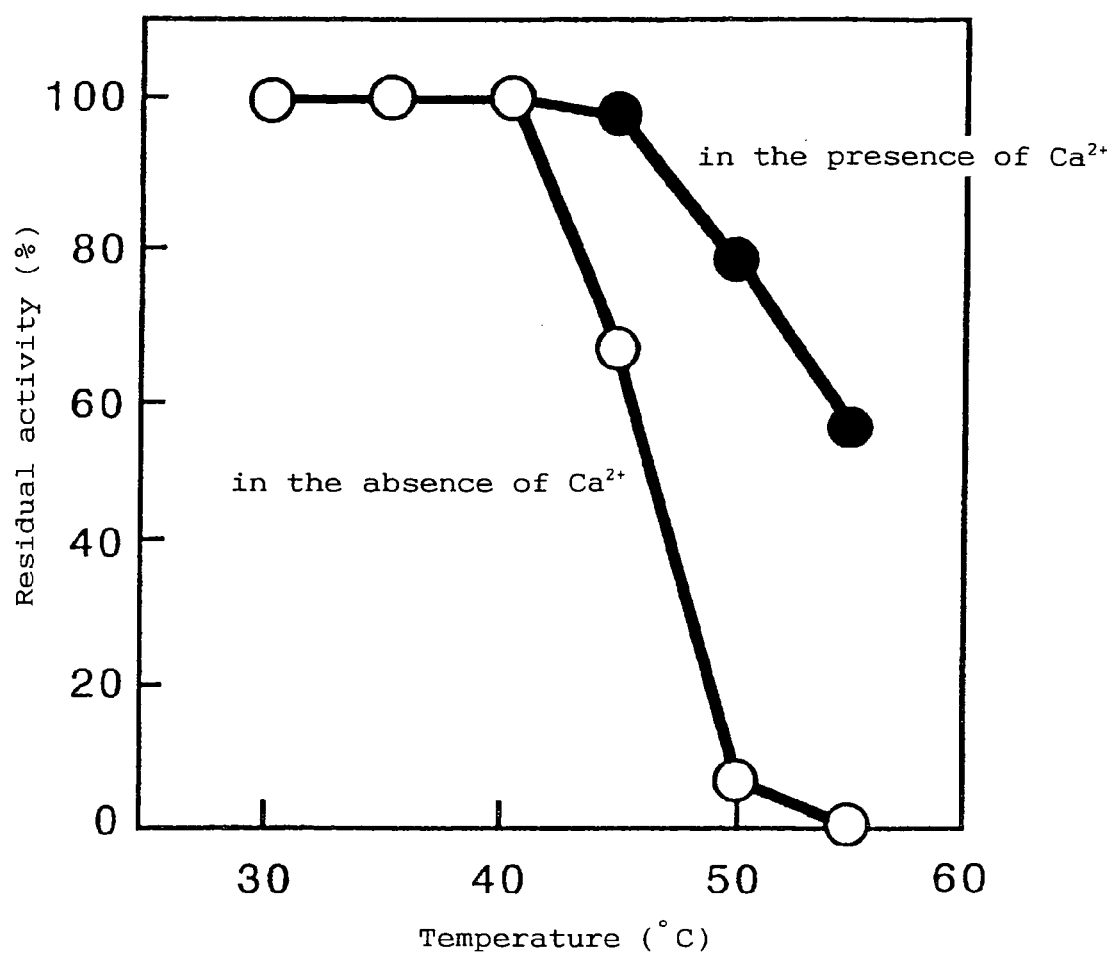
FIG. 15 shows the thermal stability of α-isomaltosylglucosaccharide-forming enzyme from a microorganism of the species *Bacillus globisporus* C11 strain.
Figure 16:
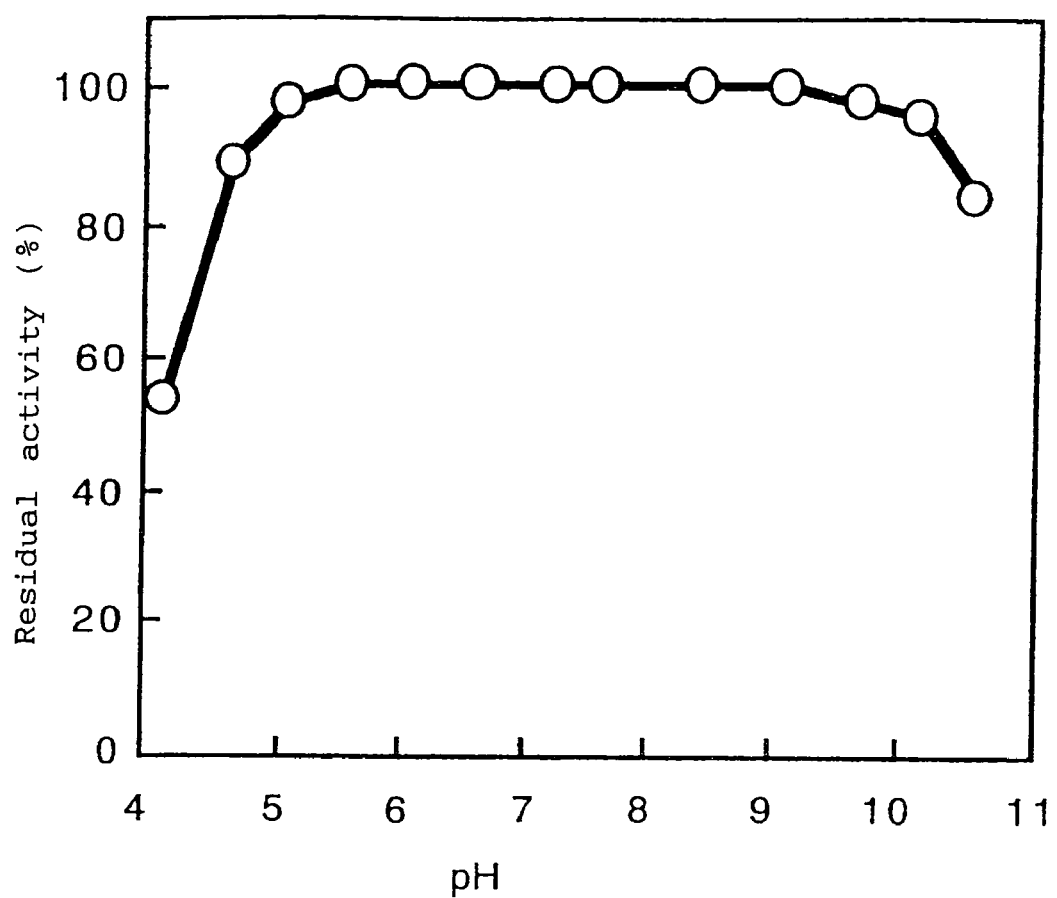
FIG. 16 shows the pH stability of α-isomaltosylglucosaccharide-forming enzyme from a microorganism of the species *Bacillus globisporus* C11 strain.

The influence of temperature and pH on the activity of α-isomaltosylglucosaccharide-forming enzyme was examined in accordance with the assay for the enzyme activity, where the influence of temperature was conducted in the presence or absence of 1 mM $Ca^{2+}$. These results are in FIG. 13 (influence of temperature) and FIG. 14 (influence of pH). The optimum temperature of the enzyme was about 45° C. in the absence of $Ca^{2+}$ and about 50° C. in the presence of 1 mM $Ca^{2+}$ when incubated at pH 6.0 for 60 min. The optimum pH of the enzyme was about 6.0 when incubated at 35° C. for 60 min. The thermal stability of the enzyme was determined by incubating it in 20 mM acetate buffers (pH 6.0) in the presence or absence of 1 mM $Ca^{2+}$ at prescribed temperatures for 60 min, cooling the resulting enzyme solutions with water, and assaying the remaining enzyme activity of each solution. The pH stability of the enzyme was determined by keeping it in 50 mM buffers having prescribed pHs at 4° C. for 24 hours, adjusting the pH of each solution to 6.0, and assaying the remaining enzyme activity of each solution. These results are respectively in FIG. 15 (thermal stability) and FIG. 16 (pH stability). As a result, the enzyme was thermally stable up to about 40° C. in the absence of $Ca^{2+}$ and about 45° C. in the presence of 1 mM $Ca^{2+}$. The pH stability of enzyme was in the range of about 5.0 to about 10.0.

The influence of metal ions on the activity of α-isomaltosylglucosaccharide-forming enzyme was examined in the presence of 1 mM of any of metal salts according to the assay for the enzyme activity. The results are in Table 7.

TABLE 7

| Metal ion | Relative activity (%) | Metal ion | Relative activity (%) |
|---|---|---|---|
| None | 100 | $Hg^{2+}$ | 4 |
| $Zn^{2+}$ | 91 | $Ba^{2+}$ | 65 |
| $Mg^{2+}$ | 98 | $Sr^{2+}$ | 83 |
| $Ca^{2+}$ | 109 | $Pb^{2+}$ | 101 |
| $Co^{2+}$ | 96 | $Fe^{2+}$ | 100 |
| $Cu^{2+}$ | 23 | $Fe^{3+}$ | 102 |
| $Ni^{2+}$ | 93 | $Mn^{2+}$ | 142 |
| $Al^{3+}$ | 100 | EDTA | 24 |

As evident form the results in Table 7, the enzyme activity was greatly inhibited by $Hg^{2+}$, $Cu^{2+}$, and EDTA and was also inhibited by $Ba^{2+}$ and $Sr^{2+}$. It was also found that the enzyme was activated by $Ca^{2+}$ and $Mn^{2+}$.

Amino acid analysis of the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ ID NO:1, i.e, tyrosine-valine-serine-serine-leucine-glycine-asparagine-leucine-isoleucine in the N-terminal region.

The comparison of the partial amino acid sequence in the N-terminal region with that derived from the α-isomaltosylglucosaccharide-forming enzyme from *Bacillus globisporus* C9 strain in Experiment 5-1 revealed that they were the same and that the N-terminal amino acid sequence, commonly found in α-isomaltosylglucosaccharide-forming enzymes, was an amino acid sequence of tyrosine-valine-serine-serine-leucine-glycine-asparagine-leucine-isoleucine of SEQ ID NO:1 in the N-terminal region.

Experiment 8-2

Property of α-Isomaltosyl-Transferring Enzyme

A purified specimen of α-isomaltosyl-transferring enzyme, obtained by the method in Experiment 7-3, was subjected to SDS-PAGE using a 7.5% (w/v) of polyacrylamide gel and then determined for molecular weight by comparing with the dynamics of standard molecular markers electrophoresed in parallel, commercialized by Bio-Rad Laboratories Inc., Brussels, Belgium, revealing that the enzyme had a molecular weight of about 102,000±20,000 daltons.

A fresh preparation of the above purified specimen was subjected to isoelectrophoresis using a gel containing 2% (w/v) ampholine commercialized by Amersham Corp., Div. Amersham International, Arlington Heights, Ill., USA, and then measured for pHs of protein bands and gel to determine the isoelectric point of the enzyme, revealing that the enzyme had an isoelectric point of about 5.6±0.5.

Figure 17:
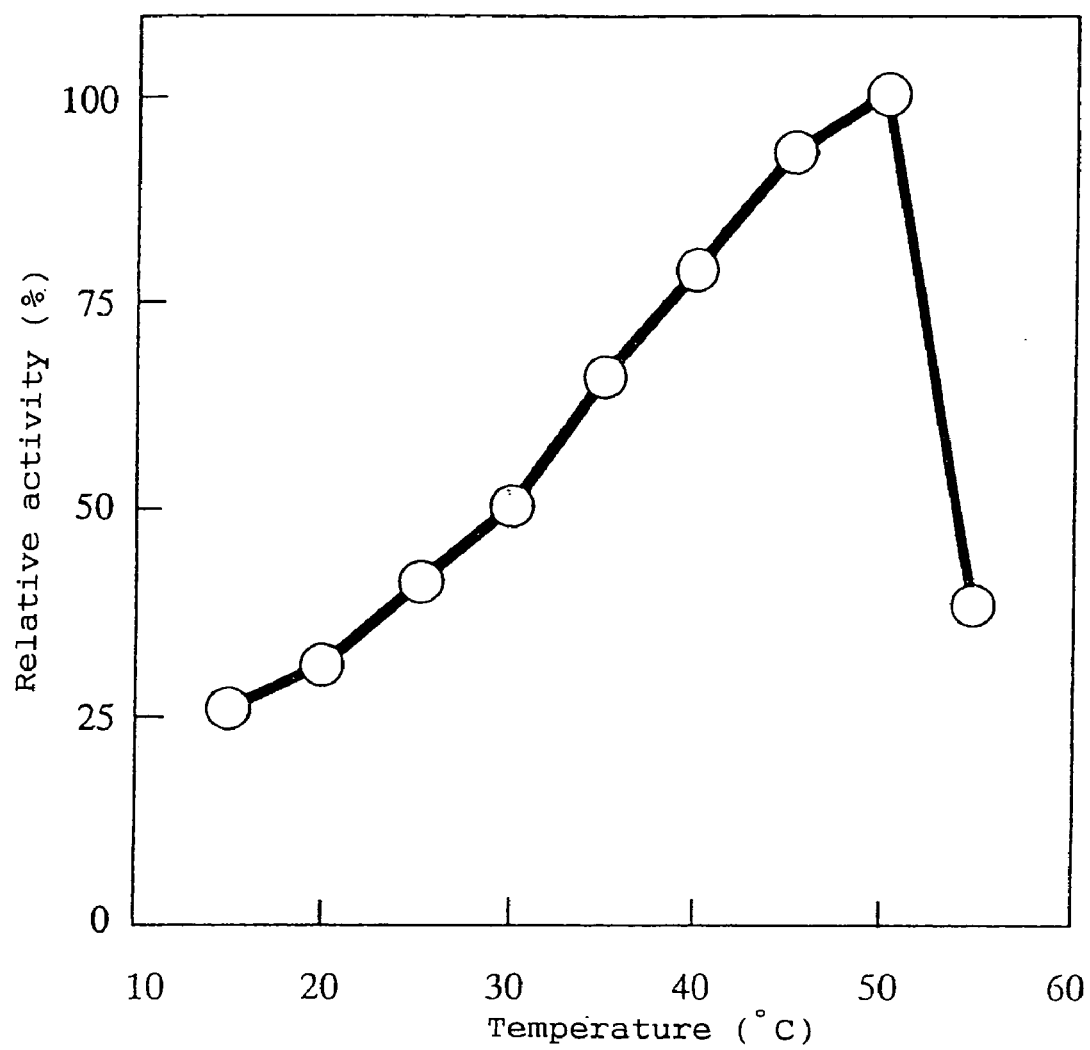
FIG. 17 shows the thermal influence on the enzymatic activity of α-isomaltosyl-transferring enzyme from a microorganism of the species *Bacillus globisporus* C11 strain.
Figure 18:
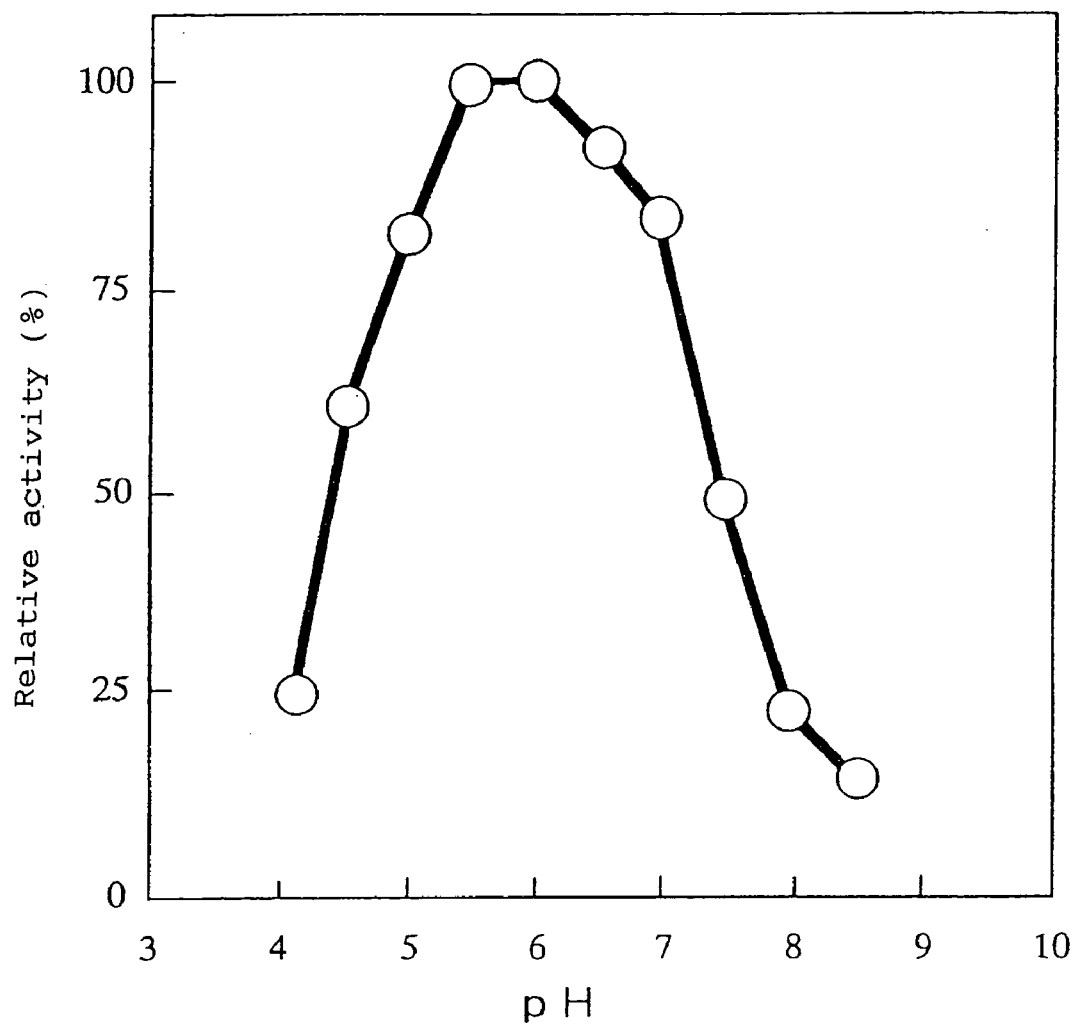
FIG. 18 shows the pH influence on the enzymatic activity of α-isomaltosyl-transferring enzyme from a microorganism of the species *Bacillus globisporus* C11 strain.
Figure 19:
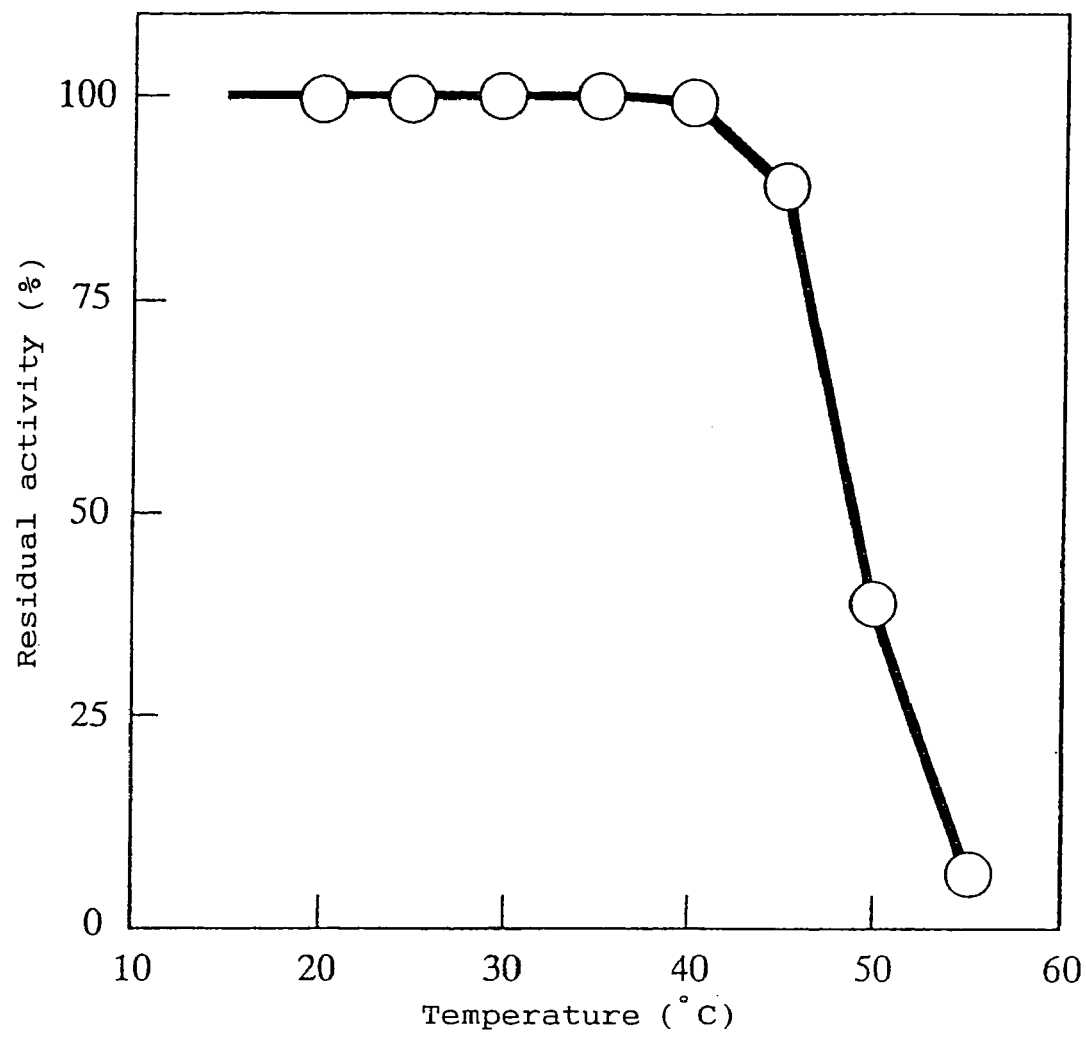
FIG. 19 shows the thermal stability of α-isomaltosyl-transferring enzyme from a microorganism of the species *Bacillus globisporus* C11 strain.
Figure 20:
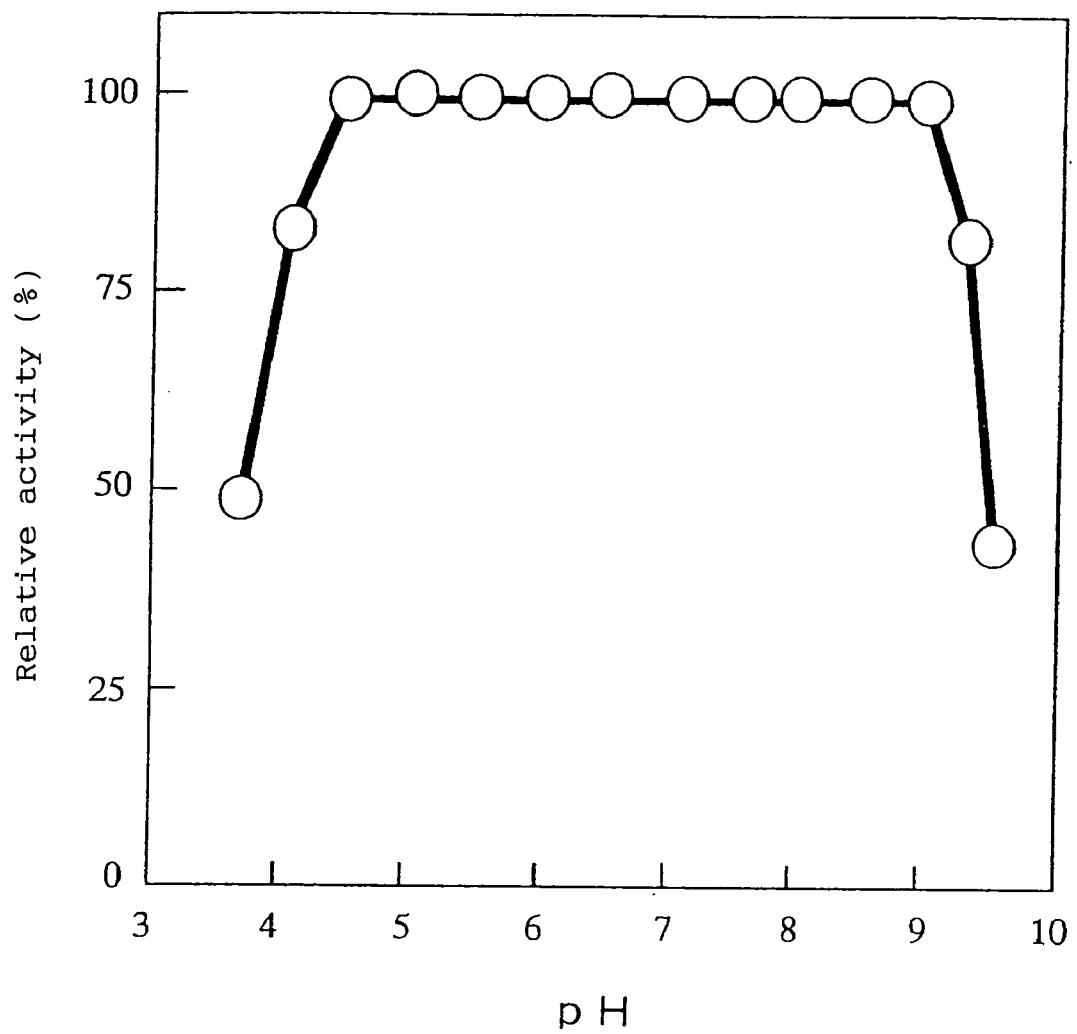
FIG. 20 shows the pH stability of α-isomaltosyl-transferring enzyme from a microorganism of the species *Bacillus globisporus* C11 strain.

The influence of temperature and pH on the activity of α-isomaltosyl-transferring enzyme was examined in accordance with the assay for the enzyme activity. These results are respectively in FIG. 17 (influence of temperature) and FIG. 18 (influence of pH). The optimum temperature of the enzyme was about 50° C. when incubated at pH 6.0 for 30 min. The optimum pH of the enzyme was about 5.5 to about 6.0 when incubated at 35° C. for 30 min. The thermal stability of the enzyme was determined by incubating it in 20 mM acetate buffers (pH 6.0) at prescribed temperatures for 60 min, cooling the resulting enzyme solutions with water, and assaying the remaining enzyme activity of each solution. The pH stability of the enzyme was determined by keeping it in 50 mM buffers having prescribed pHs at 4° C. for 24 hours, adjusting the pH of each solution to 6.0, and assaying the remaining enzyme activity of each solution. These results are respectively in FIG. 19 (thermal stability) and FIG. 20 (pH stability). As a result, the enzyme was thermally stable up to about 40° C. and was stable at pHs of about 4.5 to about 9.0.

The influence of metal ions on the activity of α-isomaltosyl-transferring enzyme was examined in the presence of 1 mM of any of metal salts according to the assay for the enzyme activity. The results are in Table 8.

TABLE 8

| Metal ion | Relative activity (%) | Metal ion | Relative activity (%) |
|---|---|---|---|
| None | 100 | $Hg^{2+}$ | 2 |
| $Zn^{2+}$ | 83 | $Ba^{2+}$ | 90 |
| $Mg^{2+}$ | 91 | $Sr^{2+}$ | 93 |
| $Ca^{2+}$ | 91 | $Pb^{2+}$ | 74 |
| $Co^{2+}$ | 89 | $Fe^{2+}$ | 104 |
| $Cu^{2+}$ | 56 | $Fe^{3+}$ | 88 |
| $Ni^{2+}$ | 89 | $Mn^{2+}$ | 93 |
| $Al^{3+}$ | 89 | EDTA | 98 |

As evident form the results in Table 8, the enzyme activity was significantly inhibited by $Hg^{2+}$ and was also inhibited by $Cu^{2+}$. It was also found that the enzyme was not activated by $Ca^{2+}$ and not inhibited by EDTA.

Amino acid analysis of the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ ID NO:3, i.e., isoleucine-aspartic acid-glycine-valine-tyrosine-histidine-alanine-proline-tyrosine-glycine in the N-terminal region.

The comparison of the partial amino acid sequence in the N-terminal region with that derived from the α-isomaltosyl-transferring enzyme from *Bacillus globisporus* C9 strain in Experiment 5-2 revealed that they had a common amino acid sequence of isoleucine-aspartic acid-glycine-valine-tyrosine-histidine-alanine-proline, as shown in SEQ ID NO:4 at the N-terminal region.

Experiment 9

Amino Acid Sequence of α-Isomaltosylglucosaccharide-Forming Enzyme

Experiment 9-1

Internal Amino Acid Sequence of α-Isomaltosylglucosaccharide-Forming Enzyme

A part of a purified specimen of α-isomaltosylglucosaccharide-forming enzyme, obtained by the method in Experiment 7-2, was dialyzed against 10 mM Tris-HCl buffer (pH 9.0), and the dialyzed solution was diluted with a fresh preparation of the same buffer to give a concentration of about one milligram per milliliter. One milliliter of the dilute as a test sample was admixed with 10 μg of a trypsin commercialized by Wako Pure Chemical Industries, Ltd., Tokyo, Japan, and incubated at 30° C. for 22 hours to hydrolyze into peptides. To isolate the peptides, the above hydrolyzates were subjected to reverse-phase HPLC using "μ-Bondapak C18 column" with a diameter of 2.1 mm and a length of 150 mm, a product of Waters Chromatography Div., MILLIPORE Corp., Milford, USA, at a flow rate of 0.9 ml/min and at ambient temperature, and using a liner gradient of acetonitrile increasing from 8% (v/v) to 40% (v/v) in 0.1% (v/v) trifluoracetate over 120 min. The peptides eluted from the column were detected by monitoring the absorbance at a wavelength of 210 nm. Three peptide specimens named P64 with a retention time of about 64 min, P88 with a retention time of about 88 min, and P99 with a retention time of about 99 min, which had been well separated from other peptides, were separately collected and dried in vacuo and then dissolved in 200 µl of a solution containing 0.1% (v/v) trifluoroacetate and 50% (v/v) acetonitrile. Each peptide specimen was subjected to a protein sequencer for analyzing amino acid sequence up to eight amino acid residues to obtain amino acid sequences of SEQ ID NOs: 5 to 7. The analyzed internal partial amino acid sequences are in Table 9.

TABLE 9

| Peptide name | Internal partial amino acid sequence |
| --- | --- |
| P64 | aspartic acid-alanine-serine-alanine-asparagine-valine-threonine-threonine |
| P88 | tryptophane-serine-leucine-glycine-phenylalanine-methionine-asparagine-phenylalanine |
| P99 | asparagine-tyrosine-threonine-aspartic acid-alanine-tryptophane-methionine-phenylalanine |

Experiment 9-2

Internal Amino Acid Sequence of α-Isomaltosyl-Transferring Enzyme

A part of a purified specimen of α-isomaltosyl-transferring enzyme, obtained by the method in Experiment 7-3, was dialyzed against 10 mM Tris-HCl buffer (pH 9.0), and the dialyzed solution was diluted with a fresh preparation of the same buffer to give a concentration of about one milligram per milliliter. One milliliter of the dilute as a test sample was admixed with 10 µg of "Lysyl Endopeptidase" commercialized by Wako Pure Chemical Industries, Ltd., Tokyo, Japan, and allowed to react at 30° C. for 22 hours to form peptides. The resultant mixtures were subjected to reverse-phase HPLC to separate the peptides using "µ-Bondapak C18 column" having a diameter of 2.1 mm and a length of 150 mm, a product of Waters Chromatography Div., MILLIPORE Corp., Milford, USA, at a flow rate of 0.9 ml/min and at ambient temperature, and using a liner gradient of acetonitrile increasing from 8% (v/v) to 40% (v/v) in 0.1% (v/v) trifluoroacetate over 120 min. The peptides eluted from the column were detected by monitoring the absorbance at a wavelength of 210 nm. Three peptide specimens named P22 with a retention time of about 22 min, P63 with a retention time of about 63 min, and P71 with a retention time of about 71 min, which had been well separated from other peptides, were separately collected and dried in vacuo and then dissolved in 200 µl of a solution of 0.1% (v/v) trifluoroacetate and 50% (v/v) acetonitrile. Each peptide specimen was subjected to a protein sequencer for analyzing amino acid sequence up to eight amino acid residues to obtain amino acid sequences of SEQ ID NOs:8 to 10. The analyzed internal partial amino acid sequences are in Table 10.

TABLE 10

| Peptide name | Internal partial amino acid sequence |
| --- | --- |
| P22 | glycine-asparagine-glutamic acid-methionine-arginine-asparagine-glutamine-tyrosine |
| P63 | isoleucine-threonine-threonine-tryptophane-proline-isoleucine-glutamic acid-serine |
| P71 | tryptophane-alanine-phenylalanine-glycine-leucine-tryptophane-methionine-serine |

Experiment 10

Action on Saccharides

It was tested whether the following saccharides could be used as substrates for α-isomaltosylglucosaccharide-forming enzyme. For the purpose, a solution of maltose, maltotriose, maltotetraose, maltopentaose, maltohexaose, maltoheptaose, isomaltose, isomaltotriose, panose, isopanose, α,α-trehalose, kojibiose, nigerose, neotrehalose, cellobiose, gentibiose, maltitol, maltotriitol, lactose, sucrose, erlose, selaginose, maltosyl glucoside, or isomaltosyl glucoside was prepared.

To each of the above solutions was added two units/g substrate of a purified specimen of α-isomaltosylglucosaccharide-forming enzyme from either *Bacillus globisporus* C9 strain obtained by the method in Experiment 4-2, or *Bacillus globisporus* C11 strain obtained by the method in Experiment 7-2, and the resulting solutions were adjusted to give a substrate concentration of 2% (w/v) and incubated at 30° C. and pH 6.0 for 24 hours. The enzyme solutions before and after the enzymatic reactions were respectively analyzed on TLC disclosed in Experiment 1 to confirm whether the enzymes act on these substrates. The results are in Table 11.

TABLE 11

| | Enzymatic action | | | Enzymatic action | |
| --- | --- | --- | --- | --- | --- |
| Substrate | Enzyme of C9 strain | Enzyme of C11 strain | Substrate | Enzyme of C9 strain | Enzyme of C11 strain |
| Maltose | + | + | Nigerose | + | + |
| Maltotriose | ++ | ++ | Neotrehalose | + | + |
| Maltotetraose | +++ | +++ | Cellobiose | − | − |
| Maltopentaose | +++ | +++ | Gentibiose | − | − |
| Maltohexaose | +++ | +++ | Maltitol | − | − |
| Maltoheptaose | +++ | +++ | Maltotriitol | + | + |
| Isomaltose | − | − | Lactose | − | − |
| Isomaltotriose | − | − | Sucrose | − | − |
| Panose | − | − | Erlose | + | + |
| Isopanose | ++ | ++ | Selaginose | − | − |

TABLE 11-continued

| Substrate | Enzymatic action | | Substrate | Enzymatic action | |
|---|---|---|---|---|---|
| | Enzyme of C9 strain | Enzyme of C11 strain | | Enzyme of C9 strain | Enzyme of C11 strain |
| α,α-Trehalose | – | – | Maltosylglucoside | ++ | ++ |
| Kojibiose | + | + | Isomaltosylglucoside | – | – |

Note:
Before and after the enzymatic reaction, the symbols "–", "+", "++", and "+++" mean that it showed no change, it showed a slight reduction of the color of substrate spot and the formation of other reaction product, it showed a high reduction of the color of substrate spot and the formation of other reaction product, and it showed a substantial disappearance of the color of substrate spot and the formation of other reaction product, respectively.

As evident from Table 11, it was revealed that the α-isomaltosylglucosaccharide-forming enzyme well acted on saccharides having a glucose polymerization degree of at least three and having a maltose structure at their non-reducing ends, among the saccharides tested. It was also found that the enzyme slightly acted on saccharides, having a glucose polymerization degree of two, such as maltose, kojibiose, nigerose, neotrehalose, maltotriitol, and erlose.

Experiment 11

Reaction Product from Maltooligosaccharide

Experiment 11-1

Preparation of Reaction Product

To an aqueous solution containing one percent (w/v) of maltose, maltotriose, maltotetraose, or maltopentaose as a substrate was added a purified specimen of α-isomaltosylglucosaccharide-forming enzyme obtained by the method in Experiment 7-2 in an amount of two units/g solid for maltose and maltotriose, 0.2 unit/g solid for maltotetraose for maltotetraose, and 0.1 unit/g solid for maltopentaose, followed by the incubation at 35° C. and pH 6.0 for eight hours. After a 10-min incubation at 100° C., the enzymatic reaction was suspended. The resulting reaction solutions were respectively measured for saccharide composition on HPLC using "YMC-PACK ODS-AQ303", a column commercialized by YMC Co., Ltd., Tokyo, Japan, at a column temperature of 40° C. and a flow rate of 0.5 ml/min of water, and using as a detector "RI-8012", a differential refractometer commercialized by Tosoh Corporation, Tokyo, Japan. The results are in Table 12.

TABLE 12

| Saccharide as reaction product | Substrate | | | |
|---|---|---|---|---|
| | Maltose | Maltotriose | Maltotetraose | Maltopentaose |
| Glucose | 8.5 | 0.1 | 0.0 | 0.0 |
| Maltose | 78.0 | 17.9 | 0.3 | 0.0 |
| Maltotriose | 0.8 | 45.3 | 22.7 | 1.9 |
| Maltotetraose | 0.0 | 1.8 | 35.1 | 19.2 |
| Maltopentaose | 0.0 | 0.0 | 3.5 | 34.4 |
| Maltohexaose | 0.0 | 0.0 | 0.0 | 4.6 |
| Isomaltose | 0.5 | 0.0 | 0.0 | 0.0 |
| Glucosylmaltose | 8.2 | 1.2 | 0.0 | 0.0 |
| Glucosylmaltotriose | 2.4 | 31.5 | 6.8 | 0.0 |
| X | 0.0 | 2.1 | 30.0 | 11.4 |
| Y | 0.0 | 0.0 | 1.4 | 26.8 |
| Z | 0.0 | 0.0 | 0.0 | 1.7 |
| Others | 0.6 | 0.1 | 0.2 | 0.0 |

Note:
In the table,
glucosylmaltose means α-isomaltosylglucose alias $6^2$-O-α-glucosylmaltose or panose;
glucosylmaltotriose means α-isomaltosylglucose alias $6^3$-O-α-glucosylmaltotriose;
X means the α-isomaltosylglucotriose in Experiment 11-2, alias $6^4$-O-α-glucosylmaltotetraose;
Y means the α-isomaltosylglucotetraose in Experiment 11-2, alias $6^5$-O-α-glucosylmaltopentaose; and
Z means an unidentified saccharide.

As evident from the results in Table 12, it was revealed that, after the action of the α-isomaltosylglucosaccharide-forming enzyme, glucose and α-isomaltosylglucose alias $6^2$-O-α-glucosylmaltose or panose were mainly formed from maltose as a substrate; and from maltotriose as a substrate, maltose and α-isomaltosylglucose alias $6^3$-O-α-glucosylmaltotriose were mainly formed along with small amounts of glucose, maltotetraose, α-isomaltosylglucose alias $6^2$-O-α-glucosylmaltose or panose, and the product X. Also, it was revealed that maltotriose and the product X were mainly formed from maltotetraose as a substrate along with small amounts of maltose, maltopentaose, α-isomaltosylglucose alias $6^3$-O-α-glucosylmaltotriose, and the product Y; and that maltotetraose and the product Y were mainly formed from maltopentaose as a substrate along with small amounts of maltotriose, maltohexaose, and the products X and Z.

The product X as a main product from maltotetraose as a substrate and the product Y as a main product from maltopentaose as a substrate were respectively isolated and purified as follows: The products X and Y were respectively purified on HPLC using "YMC PACK ODS-A R355-15S-15 12A", a separatory HPLC column commercialized by YMC Co., Ltd., Tokyo, Japan, to isolate a specimen of the product X having a purity of at least 99.9% from the reaction product of maltotetraose in a yield of about 8.3%, d.s.b., and a specimen of the product Y having a purity of at least 99.9% from the reaction product of maltopentaose in a yield of about 11.5%, d.s.b.

Experiment 11-2

Structural Analysis on Reaction Product

Figure 21:
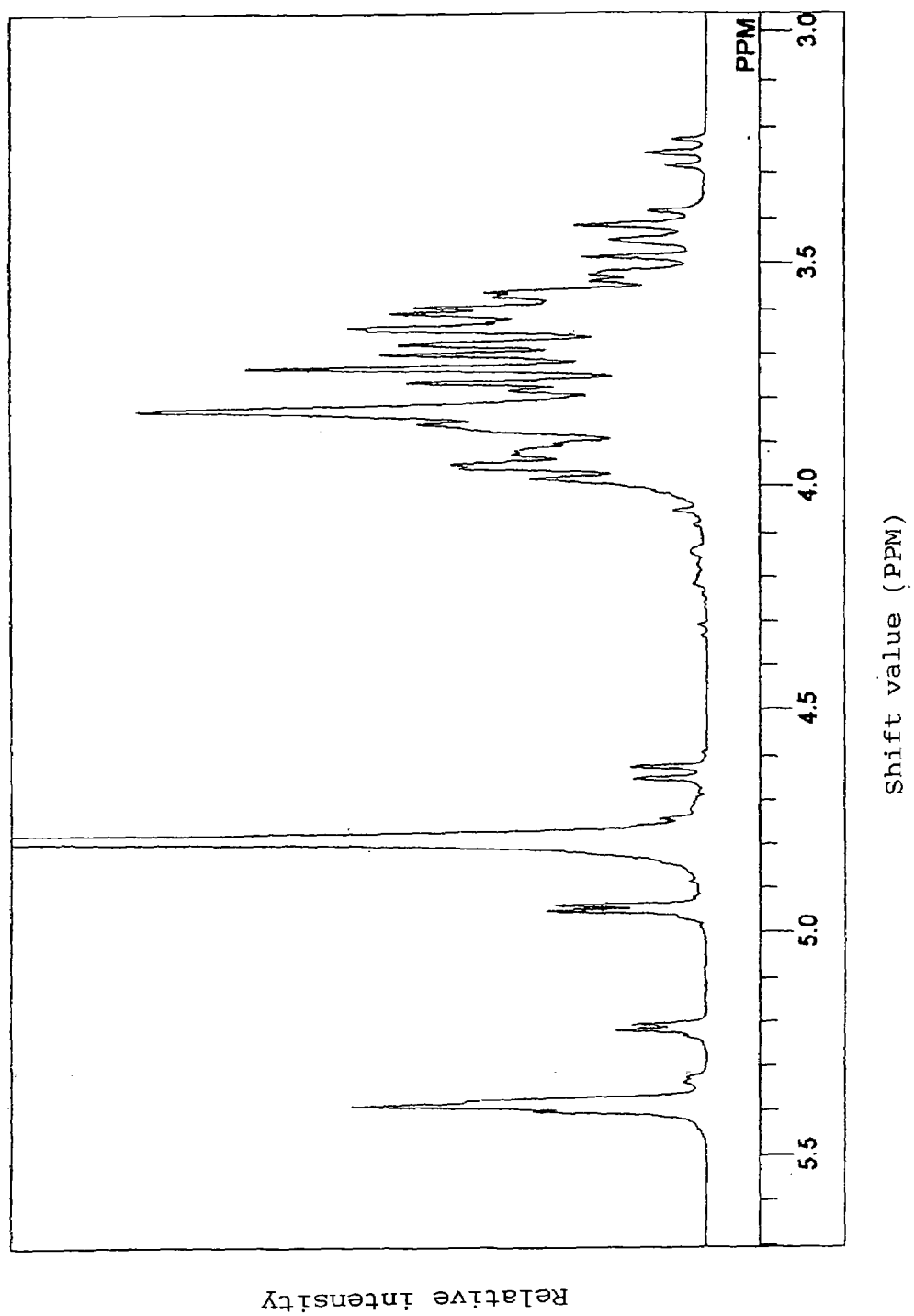
FIG. 21 is a nuclear resonance spectrum ($^1$H-NMR) of α-isomaltosylmaltotriose, obtained by the enzymatic reaction with α-isomaltosylglucosaccharide-forming enzyme.
Figure 22:
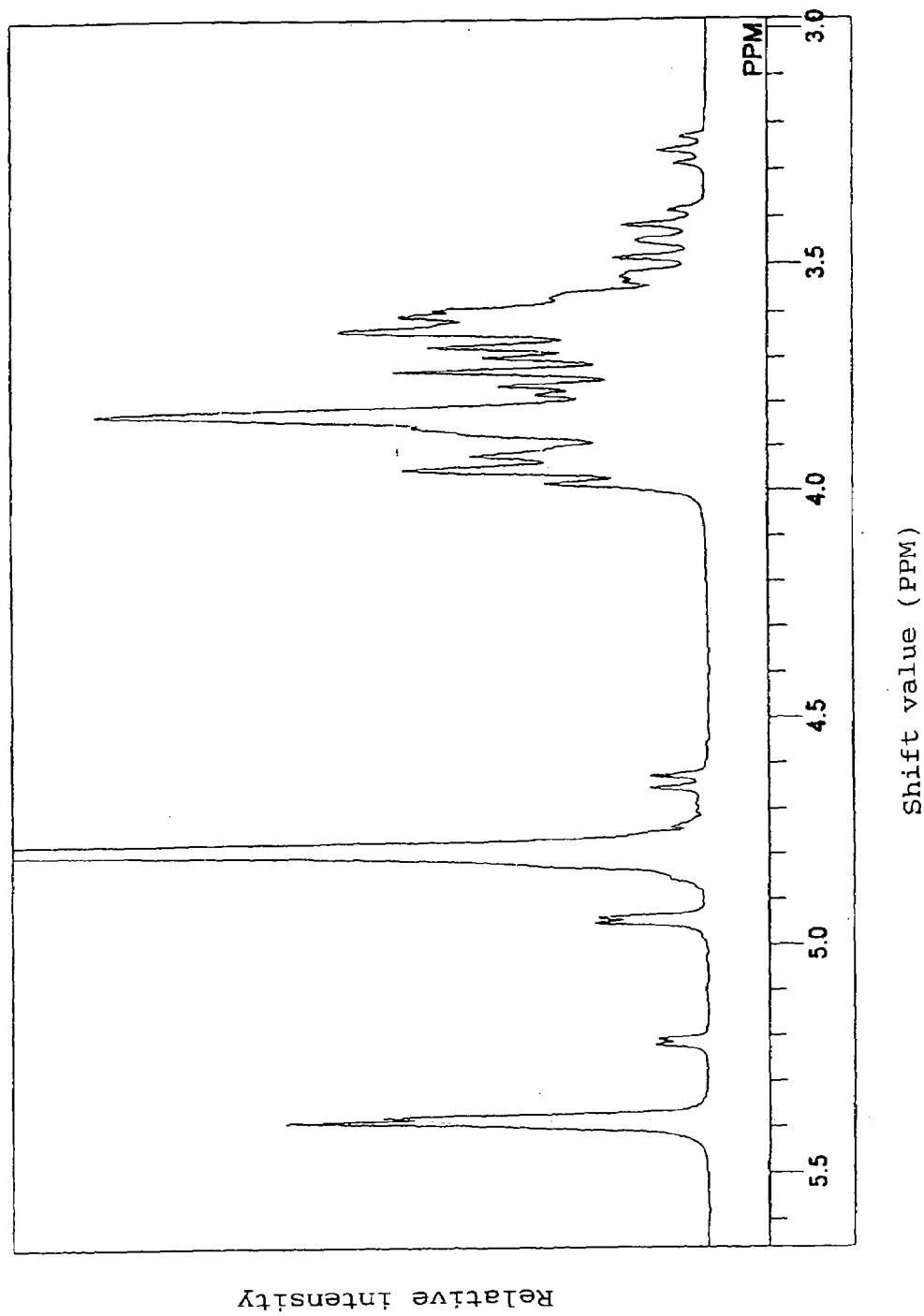
FIG. 22 is a nuclear resonance spectrum ($^1$H-NMR) of α-isomaltosylmaltotetraose, obtained by the enzymatic reaction with α-isomaltosylglucosaccharide-forming enzyme.
Figure 23:
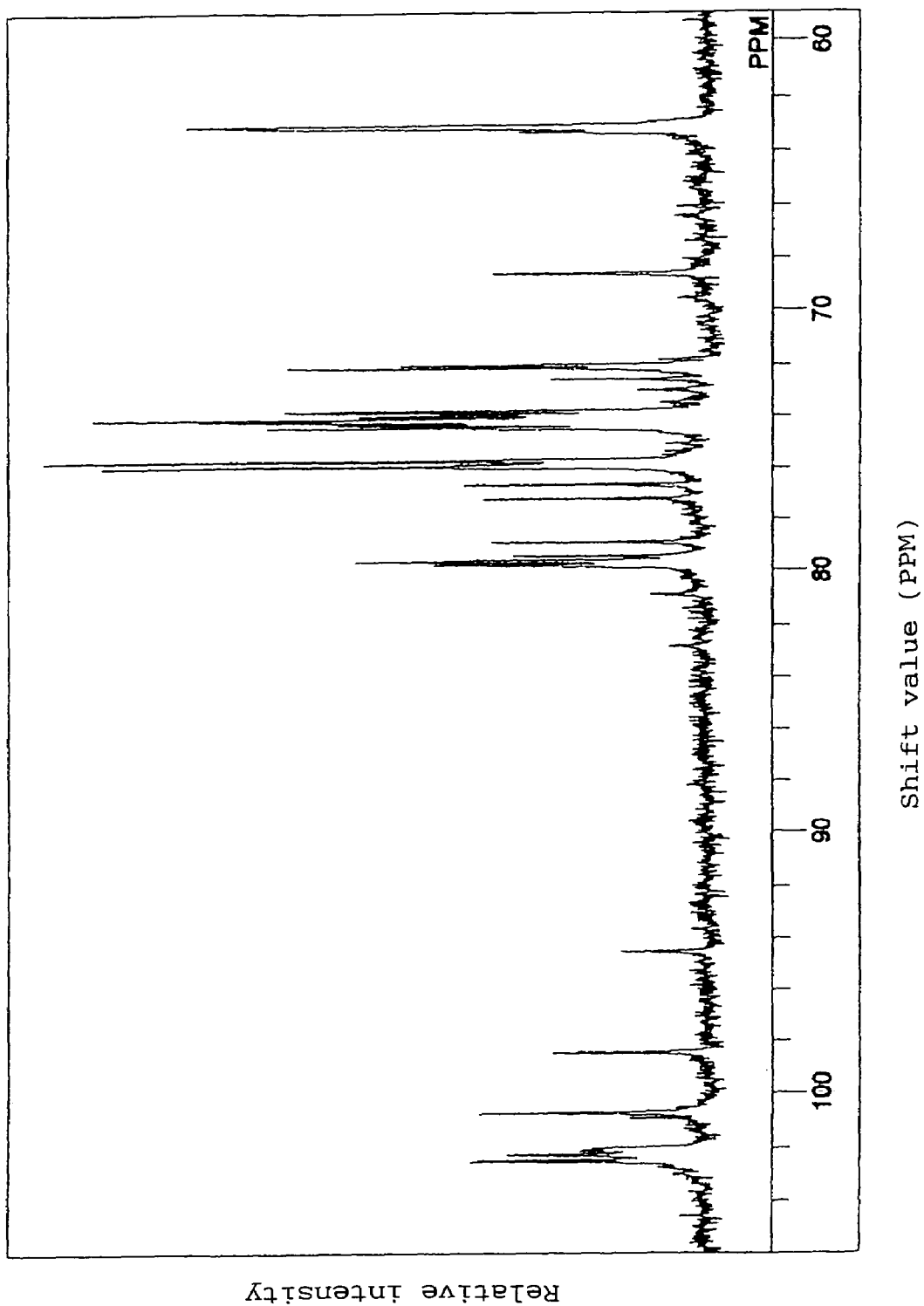
FIG. 23 is a nuclear resonance spectrum ($^{13}$C-NMR) of α-isomaltosylmaltotriose, obtained by the enzymatic reaction with α-isomaltosylglucosaccharide-forming enzyme.
Figure 24:
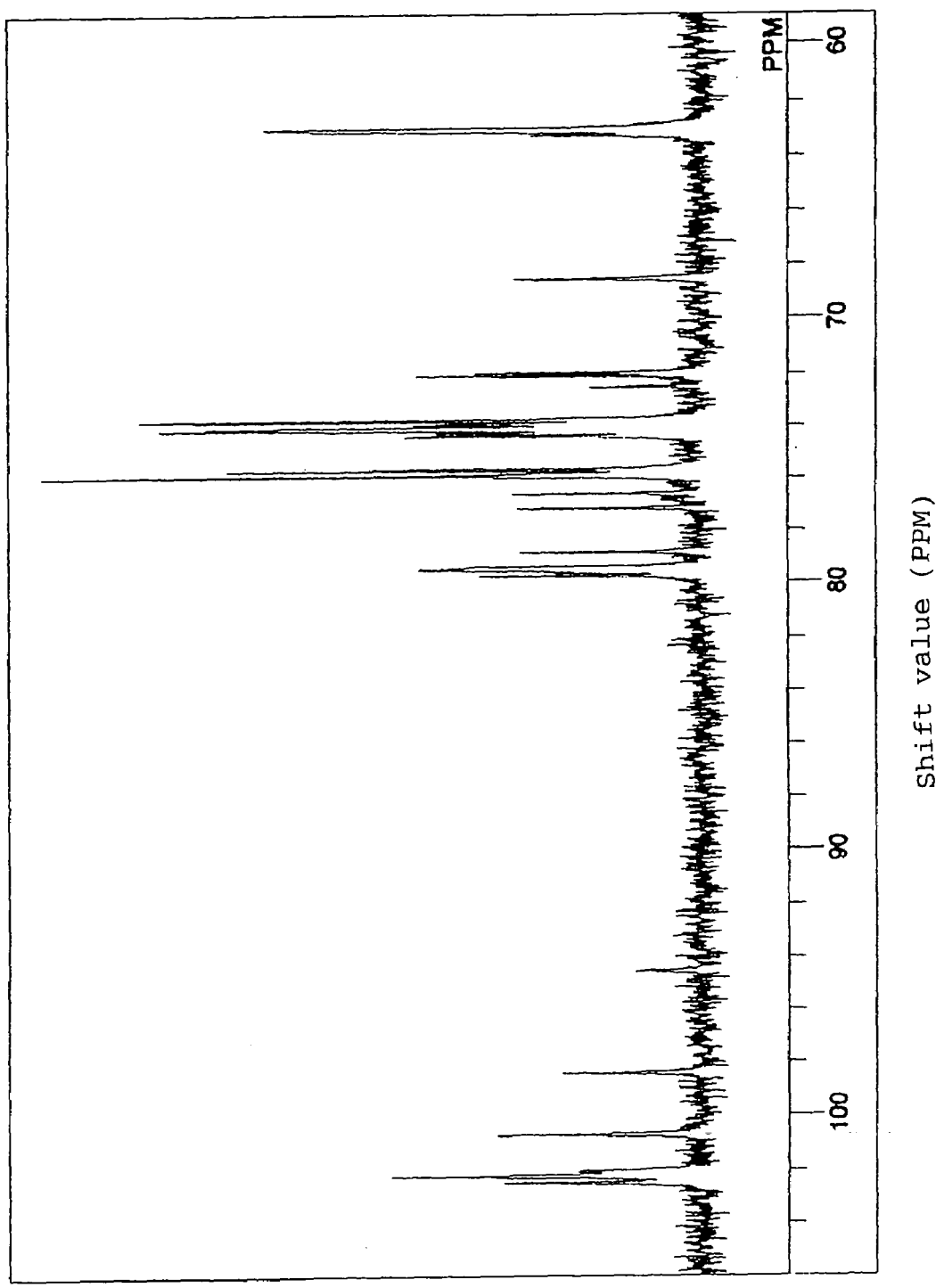
FIG. 24 is a nuclear resonance spectrum ($^{13}$C-NMR) of α-isomaltosylmaltotetraose, obtained by the enzymatic reaction with α-isomaltosylglucosaccharide-forming enzyme.

Using the products X and Y obtained by the method in Experiment 11-1, they were subjected to methyl analysis and NMR analysis in a usual manner. The results on their methyl analyses are in Table 13. For the results on their NMR analyses, FIG. 21 is a $^1$H-NMR spectrum for the product X and FIG. 22 is for the product Y. The $^{13}$C-NMR spectra for the products X and Y are respectively FIGS. 23 and 24. The assignment of the products X and Y are tabulated in Table 14.

TABLE 13

| Analyzed methyl compound | Ratio | |
|---|---|---|
| | Product X | Product Y |
| 2,3,4-Trimethyl compound | 1.00 | 1.00 |
| 2,3,6-Trimethyl compound | 3.05 | 3.98 |
| 2,3,4,6-Tetramethyl compound | 0.82 | 0.85 |

Based on these results, the product X, formed from maltotetraose via the action of the α-isomaltosylglucosaccharide-forming enzyme, was revealed as a pentasaccharide, in which a glucose residue bounds via the α-linkage to OH-6 of glucose at the non-reducing end of maltotetraose, i.e., α-isomaltosylmaltotriose alias $6^4$-O-α-glucosylmaltotetraose, represented by Formula 1.

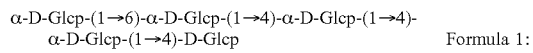

α-D-Glcp-(1→6)-α-D-Glcp-(1→4)-α-D-Glcp-(1→4)-α-D-Glcp-(1→4)-D-Glcp     Formula 1:

The product Y formed from maltopentaose was revealed as a hexasaccharide, in which a glucosyl residue bounds via the α-linkage to OH-6 of glucose at the non-reducing end of maltopentaose, i.e., α-isomaltosylmaltotetraose alias $6^5$-O-α-glucosylmaltopentaose, represented by Formula 2.

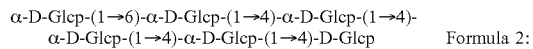

α-D-Glcp-(1→6)-α-D-Glcp-(1→4)-α-D-Glcp-(1→4)-α-D-Glcp-(1→4)-α-D-Glcp-(1→4)-D-Glcp     Formula 2:

TABLE 14

| Glucose number | Carbon number | Chemical shift on NMR (ppm) | |
|---|---|---|---|
| | | Product X | Product Y |
| a | 1a | 100.8 | 100.8 |
| | 2a | 74.2 | 74.2 |
| | 3a | 75.8 | 75.7 |
| | 4a | 72.2 | 72.2 |
| | 5a | 74.5 | 74.5 |
| | 6a | 63.2 | 63.1 |
| b | 1b | 102.6 | 102.6 |
| | 2b | 74.2 | 74.2 |
| | 3b | 75.8 | 75.7 |
| | 4b | 72.1 | 72.1 |
| | 5b | 74.0 | 74.0 |
| | 6b | 68.6 | 68.6 |
| c | 1c | 102.3 | 102.3 |
| | 2c | 74.2 | 74.2 |
| | 3c | 76.0 | 76.0 |
| | 4c | 79.6 | 79.5 |
| | 5c | 73.9 | 73.9 |
| | 6c | 63.2 | 63.1 |
| d | 1d | 102.2 | 102.3 |
| | 2d | 74.0(α), 74.4(β) | 74.2 |
| | 3d | 76.0 | 76.0 |
| | 4d | 79.8 | 79.5 |
| | 5d | 73.9 | 73.9 |
| | 6d | 63.2 | 63.1 |
| e | 1e | 94.6(α), 98.5(β) | 102.1 |
| | 2e | 74.2(α), 76.7(β) | 74.0(α), 74.4(β) |

TABLE 14-continued

| Glucose number | Carbon number | Chemical shift on NMR (ppm) | |
|---|---|---|---|
| | | Product X | Product Y |
| | 3e | 75.9(α), 78.9(β) | 76.0 |
| | 4e | 79.6(α), 79.4(β) | 79.8 |
| | 5e | 72.6(α), 77.2(β) | 73.9 |
| | 6e | 63.4(α), 63.4(β) | 63.1 |
| f | 1f | | 94.6(α), 98.5(β) |
| | 2f | | 74.2(α), 76.7(β) |
| | 3f | | 76.0(α), 78.9(β) |
| | 4f | | 79.6(α), 79.5(β) |
| | 5f | | 72.6(α), 77.2(β) |
| | 6f | | 63.3(α), 63.3(β) |

Based on these results, it was concluded that the α-isomaltosylglucosaccharide-forming enzyme acts on maltooligosaccharides as shown below:

(1) The enzyme acts on, as a substrate, a maltooligosaccharide having a glucose polymerization degree of at least two, where glucose residues are linked via the α-1,4 linkage; and catalyzes the intermolecular 6-glucosyl-transferring reaction in such a manner of transferring a glucosyl residue at the non-reducing end of a maltooligosaccharide molecule to C-6 of the glucosyl residue at the non-reducing end of another maltooligosaccharide molecule to form both an α-isomaltosylglucosaccharide alias 6-O-α-glucosylmaltooligosaccharide, having a 6-O-α-glucosyl residue and a higher glucose polymerization degree by one as compared with the intact substrate, and a maltooligosaccharide with a lower glucose polymerization degree by one as compared with the intact substrate; and (2) The enzyme slightly catalyzes the 4-glucosyl-transferring reaction and forms both a maltooligosaccharide, having a higher glucose polymerization degree by one as compared with the intact substrate, and a maltooligosaccharide having a lower glucose polymerization degree by one as compared with the intact substrate.

Experiment 12

Test on the Formation of Reducing Power

The following test was carried out to examine whether α-isomaltosylglucosaccharide-formation enzyme had an ability of forming reducing power. To a 1% (w/v) aqueous solution of maltotetraose as a substrate was added 0.25 unit/g substrate, d.s.b., of either of purified specimens of α-isomaltosylglucosaccharide-forming enzyme from *Bacillus globisporus* C9 strain obtained by the method in Experiment 4-2 and *Bacillus globisporus* C11 strain obtained by the method in Experiment 7-2, and incubated at 35° C. and pH 6.0. During the enzymatic reaction, a portion of each reaction solution was sampled at prescribed time intervals and measured for reducing powder after keeping the sampled solutions at 100° C. for 10 min to suspend the enzymatic reaction. Before and after the enzymatic reaction, the reducing saccharide content and the total sugar content were respectively quantified by the Somogyi-Nelson's method and the anthrone-sulfuric acid reaction method. The percentage of forming reducing power was calculated by the following equation:

Equation:

$$\text{Percentage of forming reducing power}(\%) = \left(\frac{AR}{AT} - \frac{BR}{BT}\right) \times 100$$

AR: Reducing sugar content after enzymatic reaction.

AT: Total sugar content after enzymatic reaction.

BR: Reducing sugar content before enzymatic reaction.

BT: Total sugar content before enzymatic reaction.

The results are in Table 15.

TABLE 15

| Reaction time (hour) | Percentage of forming reducing power (%) | |
|---|---|---|
| | Enzyme of C9 strain | Enzyme of C11 strain |
| 0 | 0.0 | 0.0 |
| 1 | 0.0 | 0.1 |
| 2 | 0.1 | 0.0 |
| 4 | 0.1 | 0.1 |
| 8 | 0.0 | 0.0 |

As evident from the results in Table 15, it was revealed that α-isomaltosylglucosaccharide-forming enzyme does not substantially increase the reducing power of the reaction product when allowed to act on maltotetraose as a substrate; the enzyme does not exhibit hydrolyzing activity or only has an undetectable level of such activity.

Experiment 13

Test on the Formation of Dextran

To study whether α-isomaltosylglucosaccharide-forming enzyme has the ability of forming dextran, it was tested in accordance with the method in *Bioscience Biotechnology and Biochemistry*, Vol. 56, pp. 169–173 (1992). To a 1% (w/v) aqueous solution of maltotetraose as a substrate was added 0.25 unit/g substrate, d.s.b., of either of purified specimens of α-isomaltosylglucosaccharide-forming enzyme from *Bacillus globisporus* C9 strain obtained by the method in Experiment 4-2 or *Bacillus globisporus* C11 strain obtained by the method in Experiment 7-2 and incubated at 35° C. and pH 6.0 for four or eight hours. After completion of the enzymatic reaction, the reaction was suspended by heating at 100° C. for 15 min. Fifty microliters of each of the reaction mixtures were placed in a centrifugation tube and then admixed and sufficiently stirred with 3-fold volumes of ethanol, followed by standing at 4° C. for 30 min. Thereafter, each of the resulting mixtures was centrifuged at 15,000 rpm for five minutes and, after removing the supernatant, the resulting sediment was admixed with one milliliter of 75% (v/v) ethanol solution and stirred for washing. The resulting each solution was centrifuged to remove supernatant, dried in vacuo, and then admixed and sufficiently stirred with one milliliter of deionized water. The total sugar content, in terms of glucose, of each resulting solution was quantified by the phenol-sulfuric acid method. As a control, the total sugar content was determined similarly as in the above except for using either of purified specimens of α-isomaltosylglucosaccharide-forming enzyme from *Bacillus globisporus* C9 strain and *Bacillus globisporus* C11 strain, which had been inactivated at 100° C. for 10 min. The content of dextran formed was calculated by the following equation:

Equation:

Content of dextran formed (mg/ml)=[(Total sugar content for test sample)−(Total sugar content for control sample)]×20

The results are in Table 16.

TABLE 16

| Reaction time (hour) | Content of dextran formed (mg/ml) | |
|---|---|---|
| | Enzyme of C9 strain | Enzyme of C11 strain |
| 4 | 0.0 | 0.0 |
| 8 | 0.0 | 0.0 |

As evident from the results in Table 16, it was revealed that the α-isomaltosylglucosaccharide-forming enzyme does not substantially have the action of forming dextran or only has an undetectable level of such activity because it did not form dextran when allowed to act on maltotetraose.

Experiment 14

Specificity of Transfer Acceptor

A variety of saccharides were tested whether they could be used as transferring-acceptors for the α-isomaltosylglucosaccharide-forming enzyme. A solution of D-glucose, D-xylose, L-xylose, D-galactose, D-fructose, D-mannose, D-arabinose, D-fucose, L-sorbose, L-rhamnose, methyl-α-glucopyranoside, methyl-β-glucopyranoside, N-acetyl-glucosamine, sorbitol, α,α-trehalose, isomaltose, isomaltotriose, cellobiose, gentibiose, maltitol, lactose, sucrose, α-cyclodextrin, β-cyclodextrin, or γ-cyclodextrin was prepared.

To each solution with a saccharide concentration of 1.6% was added "PINE-DEX #100", a partial starch hydrolysate, as a saccharide donor, to give a concentration of 4%, and admixed with one unit/g saccharide donor, d.s.b., of either of purified specimens of α-isomaltosylglucosaccharide-forming enzyme from *Bacillus globisporus* C9 strain obtained by the method in Experiment 4-2 and *Bacillus globisporus* C11 strain obtained by the method in Experiment 7-2, and incubated at 30° C. and pH 6.0 for 24 hours. The reaction mixtures after the enzymatic reactions were analyzed on gas chromatography (abbreviated as "GLC" hereinafter) for monosaccharides and disaccharides as acceptors, and on HPLC for trisaccharides and higher saccharides as acceptors to confirm whether these saccharides could be used as their transfer acceptors. In the case of performing GLC, the following apparatuses and conditions were used: GLC apparatus, "GC-16A" commercialized by Shimadzu Corporation, Tokyo, Japan; column, a stainless-steel column, 3 mm in diameter and 2 m in length, packed with 2% "SILICONE OV-17/CHROMOSOLV W", commercialized by GL Sciences Inc., Tokyo, Japan; carrier gas, nitrogen gas at a flow rate of 40 ml/min under temperature conditions of increasing from 160° C. to 320° C. at an increasing temperature rate of 7.5° C./min; and detection, a hydrogen flame ionization detector. In the case of HPLC analysis, the apparatuses and conditions used were: HPLC apparatus, "CCPD" commercialized by Tosoh Corporation, Tokyo, Japan; column, "ODS-AQ-303" commercialized by YMC Co., Ltd., Tokyo, Japan; eluent, water at a flow rate of 0.5 ml/min; and detection, a differential refractometer. The results are in Table 17.

TABLE 17

| Saccharide | Product of saccharide transferring reaction | | Saccharide | Product of saccharide transferring reaction | |
|---|---|---|---|---|---|
| | Enzyme of C9 strain | Enzyme of C11 strain | | Enzyme of C9 strain | Enzyme of C11 strain |
| D-Glucose | + | + | Sorbitol | − | − |
| D-Xylose | ++ | ++ | α,α-Trehalose | ++ | ++ |
| L-Xylose | ++ | ++ | Isomaltose | ++ | ++ |
| D-Galactose | + | + | Isomaltotriose | ++ | ++ |
| D-Fructose | + | + | Cellobiose | ++ | ++ |
| D-Mannose | − | − | Gentibiose | ++ | ++ |
| D-Arabinose | ± | ± | Maltitol | ++ | ++ |
| D-Fucose | + | + | Lactose | ++ | ++ |
| L-Sorbose | + | + | Sucrose | ++ | ++ |
| L-Rhamnose | − | − | α-Cyclodextrin | − | − |
| Methyl-α-glucopyranoside | ++ | ++ | β-Cyclodextrin | − | − |
| Methyl-β-glucopyranoside | ++ | ++ | γ-Cyclodextrin | − | − |
| N-Acetyl-glucosamine | + | + | | | |

Note:
In the table, the symbols "−", "±", "+", and "++" mean that no saccharide-transferred product was detected through transferring reaction to acceptor; a saccharide-transferred product was detected in an amount of less than one percent through transfer reaction to acceptor; a saccharide-transferred product was detected in an amount of at least one percent but less than ten percent through transferring reaction to acceptor; and a saccharide-transferred product was detected in an amount of at least ten percent through transferring reaction to acceptor.

As evident from the results in Table 17, it was revealed that the α-isomaltosylglucosaccharide utilizes different types of saccharides as transfer acceptors, particularly, the enzyme most preferably transfers a saccharide to D-/L-xylose, methyl-α-glucopyranoside, methyl-β-glucopyranoside, α,α-trehalose, isomaltose, isomaltotriose, cellobiose, gentibiose, maltitol, lactose, and sucrose; next to D-glucose, D-fructose, D-fucose, L-sorbose, and N-acetylglucosamine; and then to D-arabinose.

The properties of the α-isomaltosylglucosaccharide-forming enzyme described above were compared with those of a previously reported enzyme having 6-glucosyl-transferring action; a dextrin dextranase disclosed in "*Bioscience Biotechnology and Biochemistry*", Vol. 56, pp. 169–173 (1992); and a transglucosidase disclosed in "*Nippon Nogeikagaku Kaishi*", Vol. 37, pp. 668–672 (1963). The results are in Table 18.

TABLE 18

| Property | α-Isomaltosyl-glucosaccharide-forming enzyme | | Dextrin dextranase | Transglucosidase |
|---|---|---|---|---|
| | C9 strain | C11 strain | (Control) | (Control) |
| Hydrolysing ability | Negative | Negative | Negative | Significantly positive |
| Ability of forming dextran | Negative | Negative | Positive | Negative |
| Optimum pH | 6.0–6.5 | 6.0 | 4.0–4.2 | 3.5 |
| Inhibition by EDTA | Positive | Positive | Negative | Negative |

As evident from Table 18, the α-isomaltosylglucosaccharide-forming enzyme had outstandingly novel physicochemical properties completely different from those of known dextrin dextranase and transglucosidase.

Experiment 15

Formation of Cyclotetrasaccharide

Using different saccharides, the formation of cyclotetrasaccharide by α-isomaltosylglucosaccharide-forming enzyme and α-isomaltosyl-transferring enzyme was tested: It was prepared a solution of maltose, maltotriose, maltotetraose, maltopentaose, amylose, soluble starch, "PINE-DEX #100" (a partial starch hydrolyzate commercialized by Matsutani Chemical Ind., Tokyo, Japan), or glycogen from oyster commercialized by Wako Pure Chemical Industries Ltd., Tokyo, Japan. To each of these solutions with a respective concentration of 0.5% were added one unit/g solid of a purified specimen of α-isomaltosylglucosaccharide-forming enzyme from *Bacillus globisporus* C11 strain obtained by the method in Experiment 7-2, and 10 units/g solid of a purified specimen of α-isomaltosyl-transferring enzyme from *Bacillus globisporus* C11 strain obtained by the method in Experiment 7-3, and the resulting mixtures were subjected to an enzymatic reaction at 30° C. and pH 6.0. The enzymatic conditions were the following four systems:

(1) After 24-hour incubation of the α-isomaltosylglucosaccharide-forming enzyme with any of the saccharide solutions, the enzyme was inactivated by heating, and then the α-isomaltosyl-transferring enzyme was allowed to act on any of the resulting mixtures for 24 hours and inactivated by heating;

(2) After 24-hour simultaneous incubation of the α-isomaltosylglucosaccharide-forming enzyme and the α-isomaltosyl-transferring enzyme with any of the saccharide solutions, then the enzymes were inactivated by heating;

(3) After 24-hour incubation of the α-isomaltosylglucosaccharide-forming enzyme alone with any of the saccharide solutions, then the enzyme was inactivated by heating; and (4) After 24-hour incubation of the α-isomaltosyl-transferring enzyme alone with any of the saccharide solutions, then the enzyme was inactivated by heating.

To determine the formation level of cyclotetrasaccharide in each reaction mixture after the heating, the reaction mixtures were subjected to a similar treatment with α-glucosidase and glucoamylase as in Experiment 1 to hydrolyze the remaining reducing oligosaccharides, followed by the quantitation of cyclotetrasaccharide on HPLC. The results are in Table 19.

TABLE 19

| Substrate | Yield of cyclotetrasaccharide (%) | | | |
|---|---|---|---|---|
| | A | B | C | D |
| Maltose | 4.0 | 4.2 | 0.0 | 0.0 |
| Maltotriose | 10.2 | 12.4 | 0.0 | 0.0 |
| Maltotetraose | 11.3 | 21.5 | 0.0 | 0.0 |
| Maltopentaose | 10.5 | 37.8 | 0.0 | 0.0 |
| Amylose | 3.5 | 31.6 | 0.0 | 0.0 |
| Soluble starch | 5.1 | 38.2 | 0.0 | 0.0 |

TABLE 19-continued

| Substrate | Yield of cyclotetrasaccharide (%) | | | |
|---|---|---|---|---|
| | A | B | C | D |
| Partial starch hydrolyzate | 6.8 | 63.7 | 0.0 | 0.0 |
| Glycogen | 10.2 | 86.9 | 0.0 | 0.0 |

Note:
The symbols "A", "B", "C" and "D" mean that α-isomaltosylglucosaccharide-forming enzyme was first allowed to act on a substrate and then α-isomaltosyl-transferring enzyme was allowed acted on the resulting mixture, the α-isomaltosylglucosaccharide-forming enzyme and α-isomaltosyl-transferring enzyme were allowed to coact on a substrate, only α-isomaltosylglucosaccharide-forming enzyme was allowed to act on a substrate, and only α-isomaltosyl-transferring enzyme was allowed to act on a substrate.

As evident from the results in Table 19, no cyclotetrasaccharide was formed from any of the saccharides tested by the action of either of the α-isomaltosylglucosaccharide-forming enzyme or the α-isomaltosyl-transferring enzyme, but cyclotetrasaccharide was formed by the coaction of these enzymes. It was revealed that the formation level was relatively low as about 11% or lower when the α-isomaltosyl-transferring enzyme was allowed to act on the saccharides after the action of α-isomaltosylglucosaccharide-forming enzyme, while the level increased when the enzymes were simultaneously allowed to act on any of the saccharides tested, particularly, it increased to about 87% and about 64% when allowed to act on glycogen and partial starch hydrolyzate, respectively.

Based on the reaction properties of the α-isomaltosylglucosaccharide-forming enzyme and the α-isomaltosyl-transferring enzyme, the formation mechanism of cyclotetrasaccharide by the coaction of the above enzymes is estimated as follows:

(1) The α-isomaltosylglucosaccharide-forming enzyme acts on a glucose residue at the non-reducing end of an α-1,4 glucan chain of glycogen, partial starch hydrolyzates, etc., and intermolecularly transfers the glucose residue to OH-6 of a glucose residue at the non-reducing end of another intact α-1,4 glucan chain of glycogen, partial starch hydrolyzates, etc., to form an α-1,4 glucan chain having an α-isomaltosyl residue at the non-reducing end;

(2) The α-isomaltosyl-transferring enzyme acts on the α-1,4-glucan chain having an α-isomaltosyl residue at the non-reducing end and intermolecularly transfers the isomaltosyl residue to C-3 of glucose residue at the non-reducing end of another intact α-1,4 glucan chain having an isomaltosyl residue at the non-reducing end to form an α-1,4 glucan chain having an isomaltosyl-1,3-isomaltosyl residue at the non-reducing end;

(3) Then, the α-isomaltosyl-transferring enzyme acts on the α-1,4 glucan chain having an isomaltosyl-1,3-isomaltosyl residue at the non-reducing end and releases the isomaltosyl-1,3-isomaltosyl residue from the α-1,4 glucan chain via the intramolecular transferring reaction to cyclize the released isomaltosyl-1,3-isomaltosyl residue into cyclotetrasaccharide;

(4) From the remaining released α-1,4 glucan chain, cyclotetrasaccharide is formed through the sequential steps (1) to (3), resulting in an estimation that the coaction of α-isomaltosylglucosaccharide-forming enzyme and α-isomaltosyl-transferring enzyme in such a cyclic manner as indicated above increases the yield of cyclotetrasaccharide.

Experiment 16

Influence of Liquefaction Degree of Starch

A 15% corn starch suspension was prepared, admixed with 0.1% calcium carbonate, adjusted to pH 6.0, and then mixed with 0.2 to 2.0% per gram starch of "TERMAMYL 60L", an α-amylase commercialized by Novo Indutri A/S, Copenhagen, Denmark, followed by an enzymatic reaction at 95° C. for 10 min. Thereafter, the reaction mixture was autoclaved at 120° C. for 20 min, promptly cooled to about 35° C. to obtain a liquefied starch with a DE (dextrose equivalent) of 3.2 to 20.5. To the liquefied starch were added two units/g solid of a purified specimen of α-isomaltosylglucosaccharide-forming enzyme from *Bacillus globisporus* C11 strain obtained by the method in Experiment 7-2, and 20 units/g solid of a purified specimen of α-isomaltosyl-transferring enzyme from *Bacillus globisporus* C11 strain obtained by the method in Experiment 7-3, followed by the incubation at 35° C. for 24 hours. After completion of the reaction, the reaction mixture was heated at 100° C. for 15 min to inactivate the remaining enzymes. Then, the reaction mixture thus obtained was treated with α-glucosidase and glucoamylase similarly as in Experiment 1 to hydrolyze the remaining reducing oligosaccharides, followed by quantifying the formed cyclotetrasaccharide on HPLC. The results are in Table 20.

TABLE 20

| Amount of α-amylase per starch (%) | DE | Yield of cyclotetrasaccharide (%) |
|---|---|---|
| 0.2 | 3.2 | 54.5 |
| 0.4 | 4.8 | 50.5 |
| 0.6 | 7.8 | 44.1 |
| 1.0 | 12.5 | 39.8 |
| 1.5 | 17.3 | 34.4 |
| 2.0 | 20.5 | 30.8 |

As evident from the results in Table 20, it was revealed that the formation of cyclotetrasaccharide by the coaction of α-isomaltosylglucosaccharide-forming enzyme and α-isomaltosyl-transferring enzyme is influenced by the liquefaction degree of starch, i.e., the lower the liquefaction degree or the lower the DE, the higher the yield of cyclotetrasaccharide from starch becomes. On the contrary, the higher the liquefaction degree or the higher the DE, the lower the yield of cyclotetrasaccharide from starch becomes. It was revealed that a suitable liquefaction degree is a DE of about 20 or lower, preferably, a DE of about 12 or lower, more preferably, a DE of about 5 or lower.

Experiment 17

Influence of Concentration of Partial Starch Hydrolyzate

Aqueous solutions of "PINE-DEX #100", a partial starch hydrolyzate with a DE of about 2 to about 5, having a final concentration of 0.5 to 40%, were prepared and respectively admixed with one unit/g solid of a purified specimen of α-isomaltosylglucosaccharide-forming enzyme from *Bacillus globisporus* C11 strain obtained by the method in Experiment 7-2, and 10 units/g solid of a purified specimen of α-isomaltosyl-transferring enzyme from *Bacillus globisporus* C11 strain obtained by the method in Experiment 7-3, followed by the coaction of these enzymes at 30° C. and pH 6.0 for 48 hours. After completion of the reaction, each reaction mixture was heated at 100° C. for 15 min to inactivate the remaining enzymes, and then treated with α-glucosidase and glucoamylase similarly as in Experiment 1 to hydrolyze the remaining reducing oligosaccharides, followed by quantifying the formed cyclotetrasaccharide on HPLC. The results are in Table 18.

TABLE 18

| Concentration of PINE-DEX (%) | Yield of cyclotetrasaccharide (%) |
|---|---|
| 0.5 | 63.6 |
| 2.5 | 62.0 |
| 5 | 60.4 |
| 10 | 57.3 |
| 15 | 54.6 |
| 20 | 51.3 |
| 30 | 45.9 |
| 40 | 39.5 |

As evident from the results in Table 21, the yield of cyclotetrasaccharide was about 64% at a low concentration of 0.5%, while it was about 40% at a high concentration of 40%. The fact showed that the yield of cyclotetrasaccharide increases depending on the concentration of partial starch hydrolyzate as a substrate. The result revealed that the yield of cyclotetrasaccharide increases as the concentration of partial starch hydrolyzate decreases.

Experiment 18

Influence of the Addition of Cyclodextrin Glucanotransferase

Fifteen percent of aqueous solutions of "PINE-DEX #100", a partial starch hydrolyzate, were prepared and admixed with one unit/g solid of a purified specimen of α-isomaltosylglucosaccharide-forming enzyme from *Bacillus globisporus* C11 strain obtained by the method in Experiment 7-2, 10 units/g solid of a purified specimen of α-isomaltosyl-transferring enzyme from *Bacillus globisporus* C11 strain obtained by the method in Experiment 7-3, and 0–0.5 unit/g solid of a cyclodextrin glucanotransferase (CG-Tase) from a microorganism of the species *Bacillus stearothermophilus*, followed by the coaction of these enzymes at 30° C. and pH 6.0 for 48 hours. After completion of the reaction, the reaction mixture was heated at 100° C. for 15 min to inactivate the remaining enzymes, and then treated with α-glucosidase and glucoamylase similarly as in Experiment 1 to hydrolyze the remaining reducing oligosaccharides, followed by quantifying the formed cyclotetrasaccharide on HPLC. The results are in Table 22.

TABLE 22

| Amount of CGTase added (unit) | Yield of cyclotetrasaccharide (%) |
|---|---|
| 0 | 54.6 |
| 2.5 | 60.1 |
| 5 | 63.1 |
| 10 | 65.2 |

As evident from the Table 22, it was revealed that the addition of CGTase increases the yield of cyclotetrasaccharide.

Experiment 19

Preparation of Cyclotetrasaccharide

About 100 L of a 4% (w/v) aqueous solution of a corn phytoglycogen commercialized by Q.P. Corporation, Tokyo, Japan, was prepared, adjusted to pH 6.0 and 30° C., and then admixed with one unit/g solid of a purified specimen of α-isomaltosylglucosaccharide-forming enzyme from *Bacillus globisporus* C11 strain obtained by the method in Experiment 7-2, 10 units/g solid of a purified specimen of α-isomaltosyl-transferring enzyme from *Bacillus globisporus* C11 strain obtained by the method in Experiment 7-3, followed by the incubation for 48 hours. After completion of the reaction, the reaction mixture was heated at 100° C. for 10 min to inactivate the remaining enzymes, and a portion of the reaction mixture was sampled and then quantified on HPLC to calculate the yield of cyclotetrasaccharide, revealing that it contained 84% cyclotetrasaccharide with respect to saccharides, d.s.b. The reaction mixture was adjusted to pH 5.0 and 45° C., and then treated with α-glucosidase and glucoamylase similarly as in Experiment 1 to hydrolyze the remaining reducing oligosaccharides, etc. The resulting mixture was adjusted to pH 5.8 by the addition of sodium hydroxide and then incubated at 90° C. for one hour to inactivate the remaining enzymes and filtered to remove insoluble substances. The filtrate was concentrated using a reverse osmosis membrane to give a concentration of about 16%, d.s.b., and the concentrate was in a usual manner decolored, desalted, filtered, and concentrated to obtain about 6.2 kg of a saccharide solution with a solid content of about 3,700 g.

The saccharide solution was fed to a column packed with about 225 L of "AMBERLITE CR-1310 (Na-form)", an ion-exchange resin commercialized by Japan Organo Co., Ltd., Tokyo, Japan, and chromatographed at a column temperature of 60° C. and a flow rate of about 45 L/h. While the saccharide composition of the eluate from the column was being monitored by HPLC as described in Experiment 1, fractions of cyclotetrasaccharide with a purity of at least 98% were collected, and in a usual manner desalted, decolored, filtered, and concentrated to obtain about 7.5 kg of a saccharide solution with a solid content of about 2,500 g solids. HPLC measurement for saccharide composition of the saccharide solution revealed that it contained cyclotetrasaccharide with a purity of about 99.5%.

Experiment 20

Crystallization of Cyclotetrasaccharide in Aqueous Solution

Figure 25:
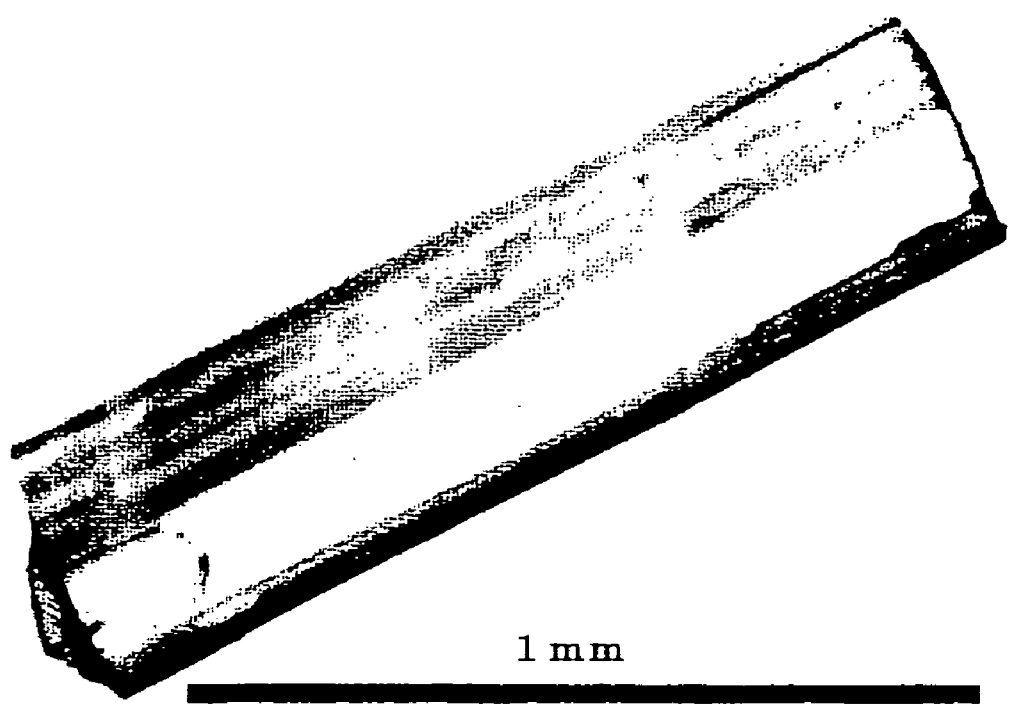
FIG. 25 is a visualized intermediate picture, displayed on a screen, of a microscopic photo for crystalline cyclotetrasaccharide, penta- or hexa-hydrate.

A fraction of cyclotetrasaccharide with a purity of at least 98%, obtained by the method in Experiment 19, was concentrated by evaporation to give a concentration of about 50%, d.s.b. About five kilograms of the concentrate was placed in a cylindrical plastic vessel and then crystallized to obtain a white crystalline powder by lowering the temperature of the concentrate from 65° C. to 20° C. over about 20 hours under gentle rotatory conditions. FIG. 25 is a microscopic photograph of such cyclotetrasaccharide. The above crystallized concentrate was separated by a centrifugal filter to obtain 1,360 g of a crystalline product by wet weight, which was then further dried at 60° C. for three hours to obtain 1,170 g of a crystalline powder of cyclotetrasaccharide. HPLC measurement of the crystalline powder revealed that it contained cyclotetrasaccharide with a quite high purity of 99.9% or over.

Figure 26:
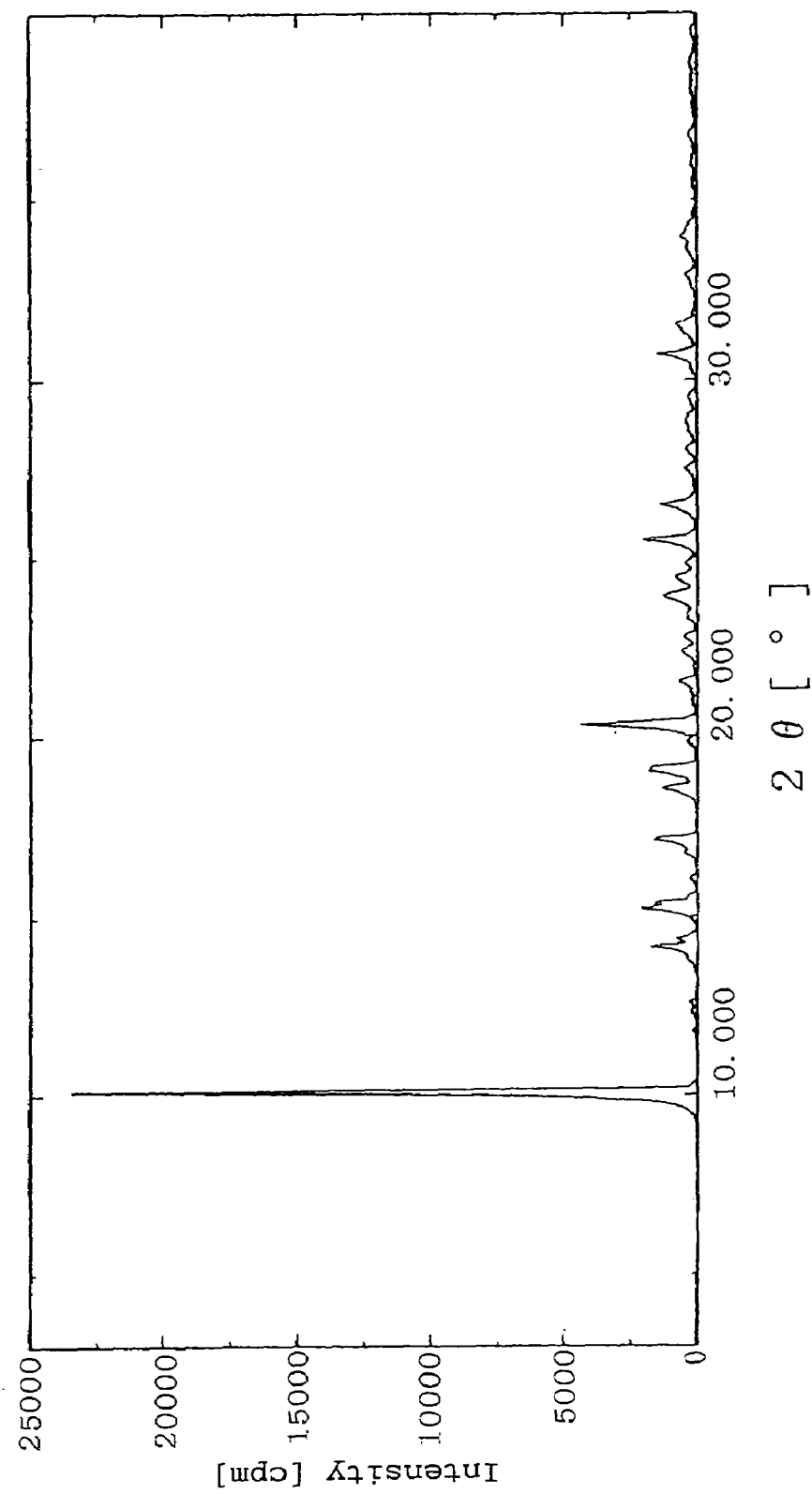
FIG. 26 is an x-ray diffraction spectrum for crystalline cyclotetrasaccharide, penta- or hexa-hydrate, when determined on x-ray powder diffraction analysis.

When analyzed on powder x-ray diffraction analysis, the cyclotetrasaccharide in a crystalline powder form had a diffraction spectrum having characteristic main diffraction angles ($2\theta$) of 10.1°, 15.2°, 20.3°, and 25.5° in FIG. 26. The Karl Fischer method of the crystalline powder revealed that it had a moisture content of 13.0%, resulting in a finding that it was a crystal of cyclotetrasaccharide having five or six moles of water per one mole of cyclotetrasaccharide.

Figure 27:
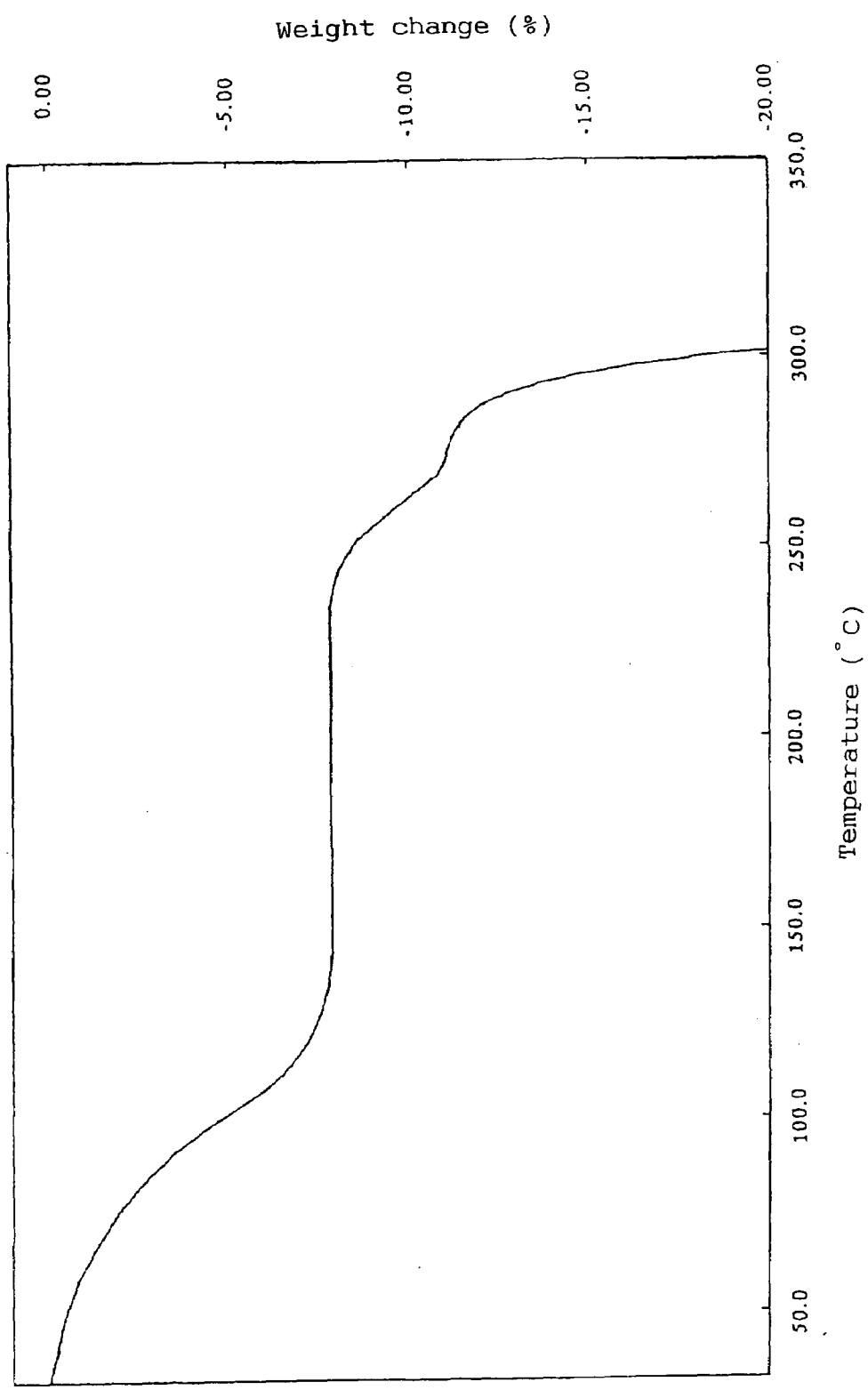
FIG. 27 is a thermogravimetric curve for crystalline cyclotetrasaccharide, penta- or hexa-hydrate, when determined on thermogravimetric analysis.

The thermogravimetric analysis of the cyclotetrasaccharide in a crystalline form gave a thermogravimetric curve in FIG. 27. Based on the relationship between the weight change and the temperature, it was successively found that the weight reduction corresponding to four or five moles of water was observed up to a temperature of 150° C., the weight reduction corresponding to one mole of water at around 250° C., and the weight reduction corresponding to the decomposition of cyclotetrasaccharide at a temperature of about 280° C. or higher. These results confirmed that the crystalline cyclotetrasaccharide, penta- or hexa-hydrate, of the present invention releases four or five moles of water to change into its crystalline monohydrate form when heated up to 150° C. at normal pressure, and further releases one mole of water to change into its anhydrous crystal form until reaching 250° C.

Experiment 21

Conversion into Crystalline Cyclotetrasaccharide, Monohydrate

Figure 28:
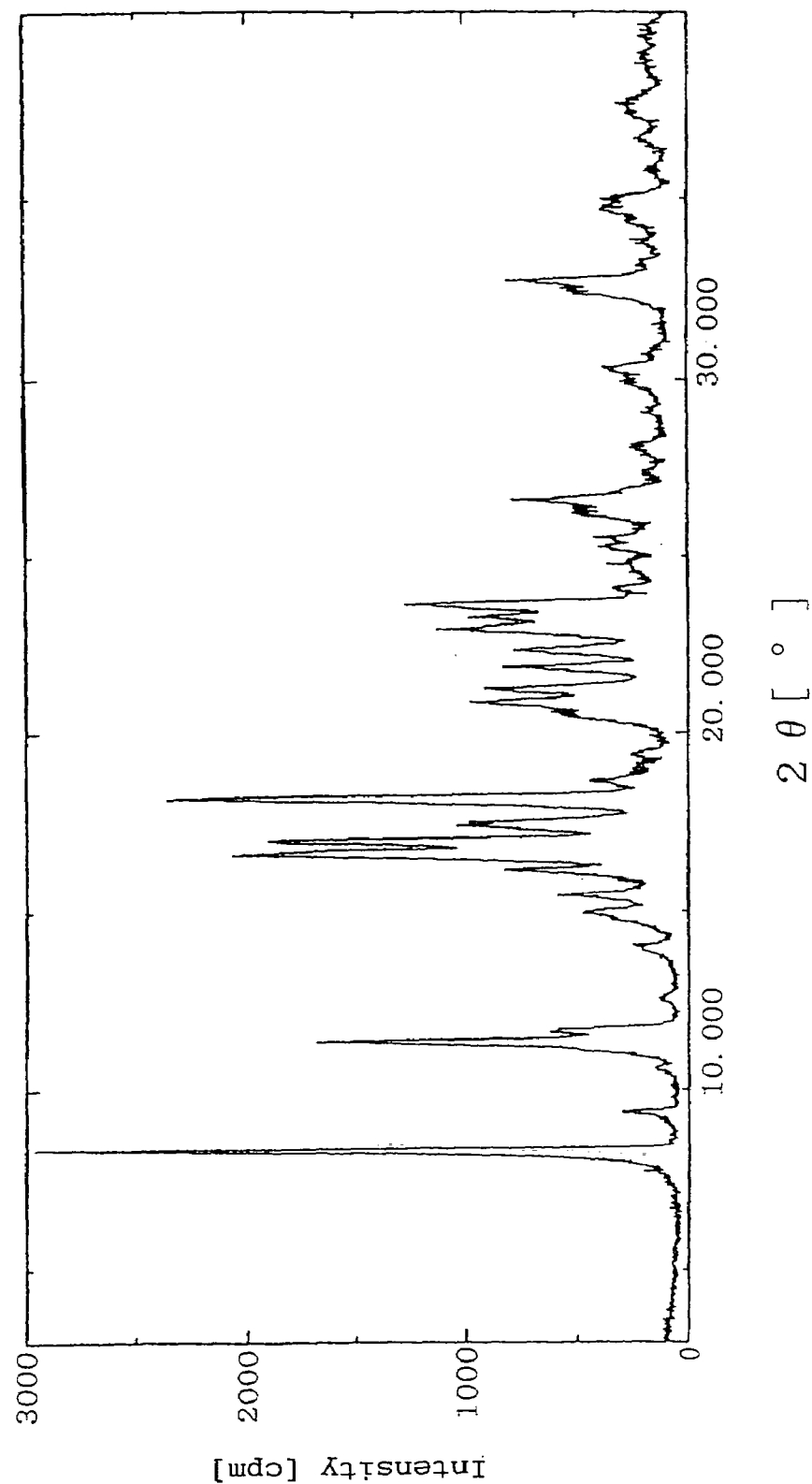
FIG. 28 is an x-ray diffraction spectrum for crystalline cyclotetrasaccharide, monohydrate, used in the present invention when determined on x-ray powder diffraction analysis.
Figure 29:
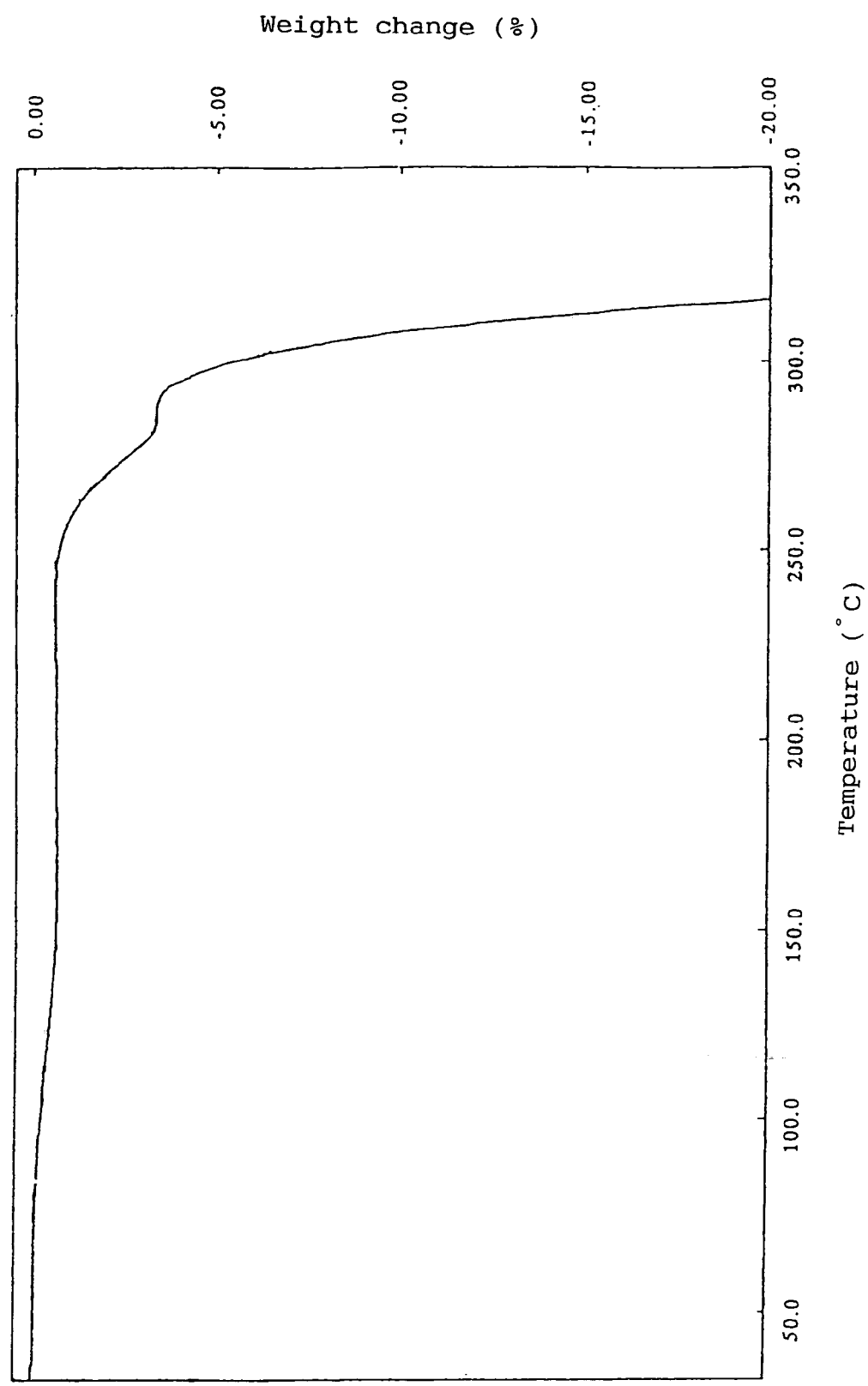
FIG. 29 is a thermogravimetric curve for crystalline cyclotetrasaccharide, monohydrate, used in the present invention when determined on thermogravimetric analysis.

Crystalline cyclotetrasaccharide, penta- or hexa-hydrate, in a powder form, obtained by the method in Experiment 20, was placed in a glass vessel, and kept in an oil bath, which had been preheated to 140° C., for 30 min. Being quite different from the result from the powder x-ray diffraction analysis of intact cyclotetrasaccharide, penta- or hexa-hydrate, free from heat treatment, the powder x-ray analysis of the cyclotetrasaccharide powder thus obtained gave a characteristic diffraction spectrum having main diffraction angles (2θ) of 8.3°, 16.6°, 17.0°, and 18.2° in FIG. 28. The Karl Fischer method of the crystalline powder revealed that it had a moisture content of about 2.7%, revealing that it was a crystal of cyclotetrasaccharide having one mole of water per one mole of cyclotetrasaccharide. The thermogravimetric analysis of the cyclotetrasaccharide in a crystalline powder form gave a thermogravimetric curve in FIG. 29. Based on the relationship between the weight change and the temperature, it was found that the weight reduction corresponding to one mole of water was observed at a temperature of about 270° C. and further observed the weight reduction corresponding to the decomposition of cyclotetrasaccharide per se at a temperature of about 290° C. or higher. These results confirmed that the cyclotetrasaccharide crystal in this experiment was crystalline cyclotetrasaccharide, monohydrate.

Experiment 22

Conversion into Anhydrous Crystal

Figure 30:
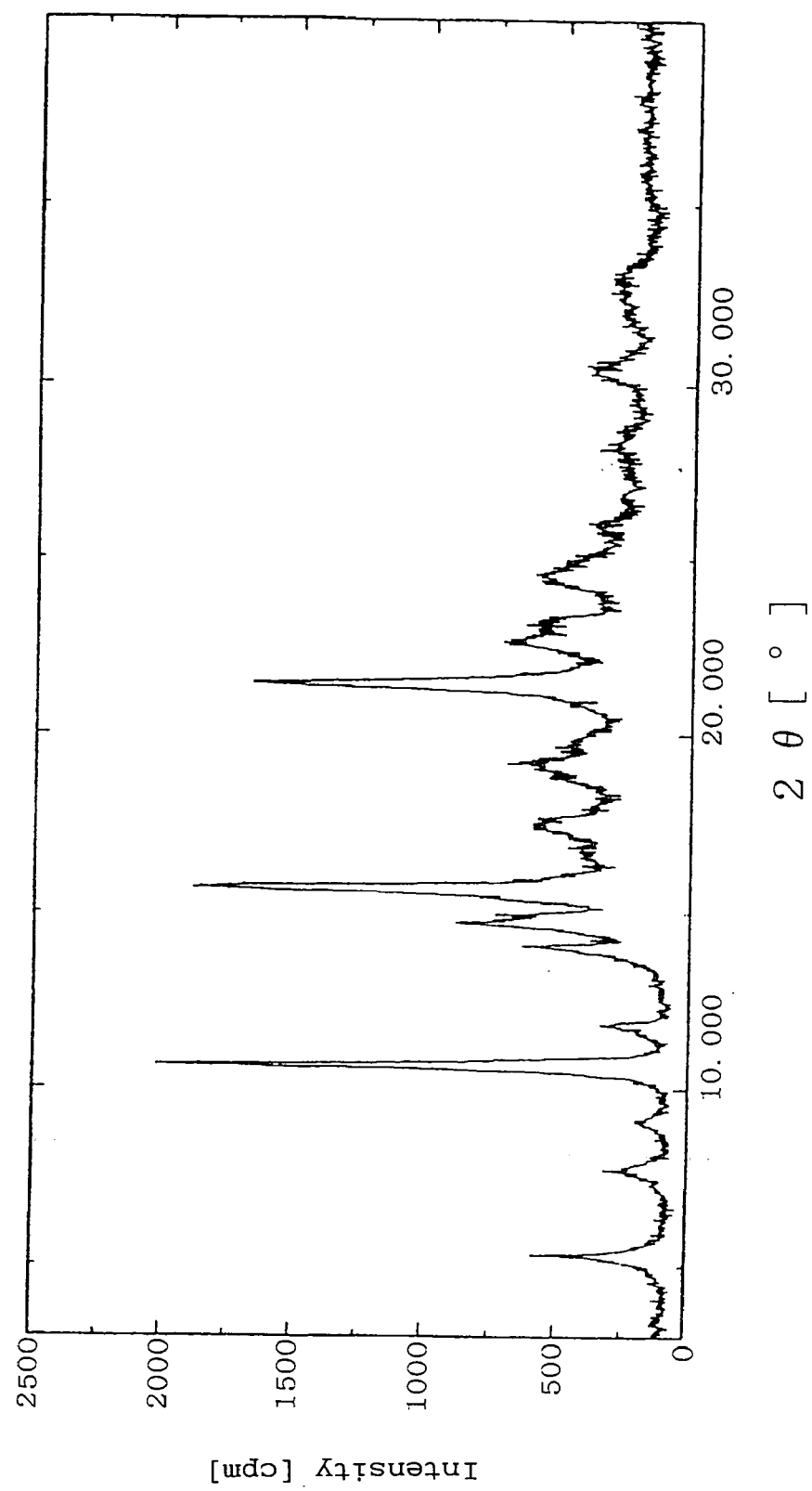
FIG. 30 is an x-ray diffraction spectrum for a powder of anhydrous crystalline cyclotetrasaccharide, obtained by drying in vacuo at 40° C. crystalline cyclotetrasaccharide, penta- or hexa-hydrate, when determined on x-ray powder diffraction analysis.
Figure 31:
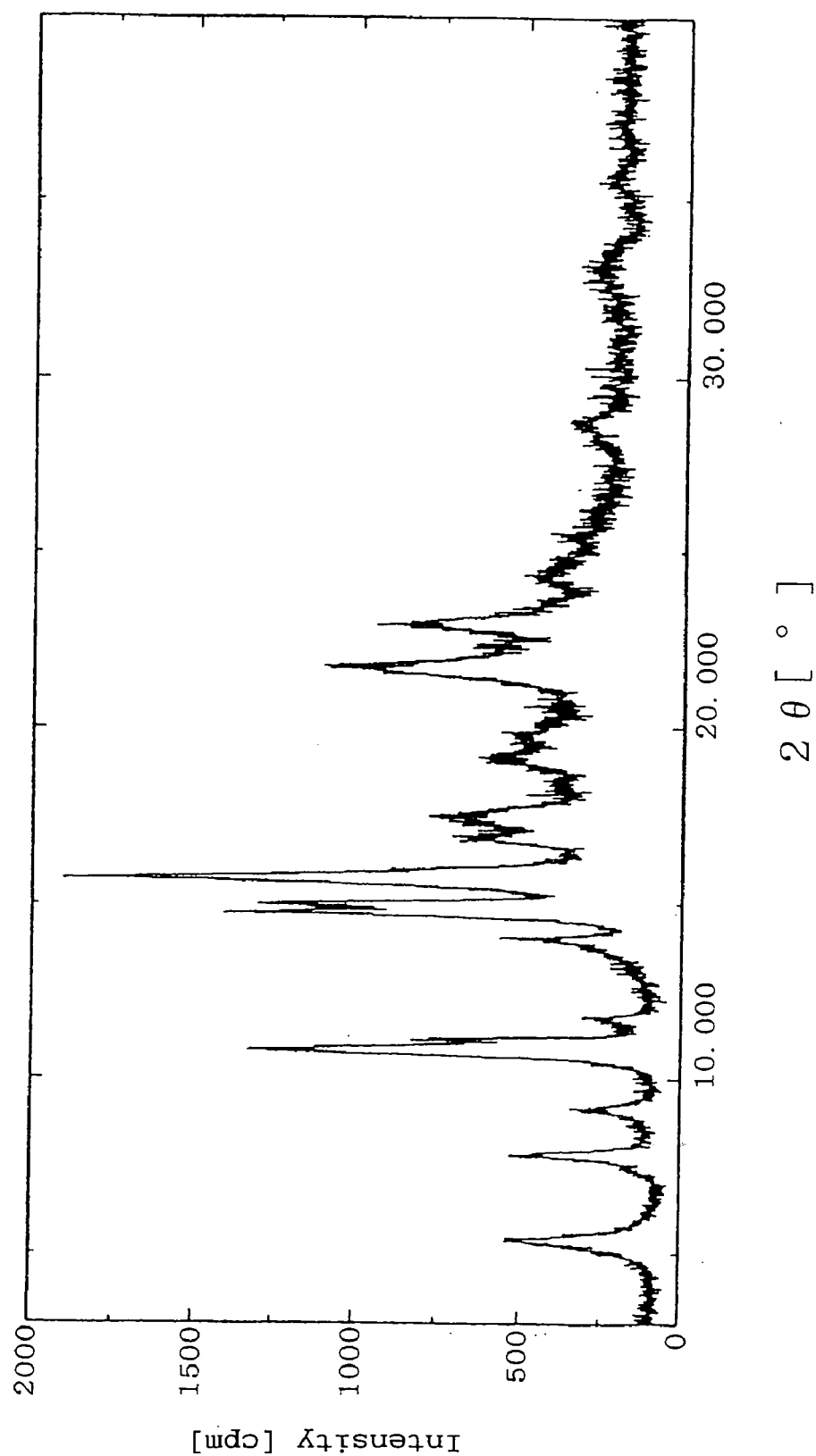
FIG. 31 is an x-ray diffraction spectrum for a powder of anhydrous crystalline cyclotetrasaccharide, obtained by drying in vacuo at 120° C. cyclotetrasaccharide crystal, penta- or hexa-hydrate, when determined on x-ray powder diffraction analysis.
Figure 32:
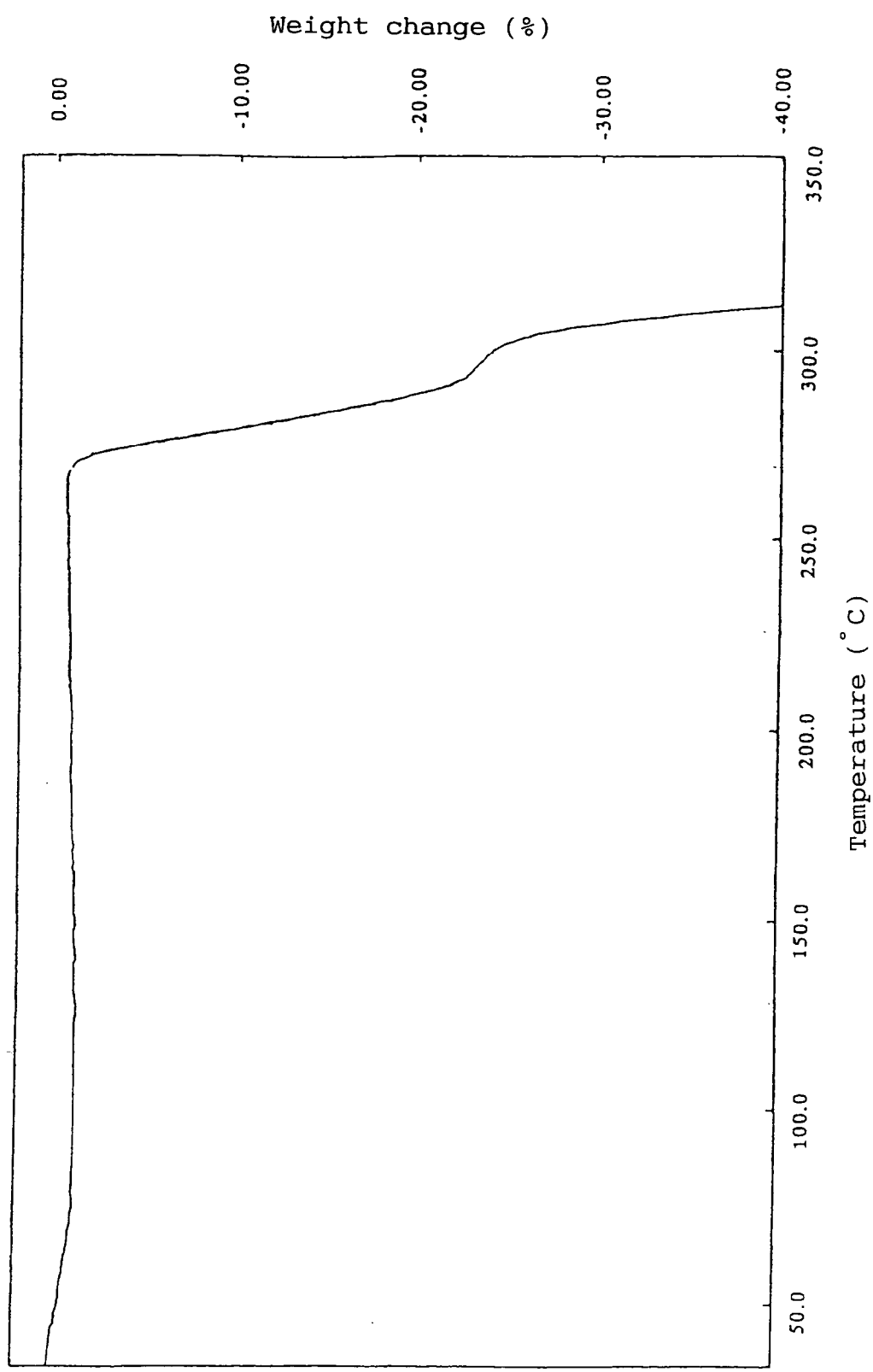
FIG. 32 is a thermogravimetric curve for an anhydrous crystalline cyclotetrasaccharide powder used in the present invention, when determined on thermogravimetric analysis.

Crystalline cyclotetrasaccharide, penta- or hexa-hydrate, in a powder form, obtained by the method in Experiment 20, was dried in vacuo at 40° C. or 120° C. for 16 hours. The Karl Fischer method of the resulting crystalline powders revealed that the one dried at 40° C. had a moisture content of about 4.2%, while the other dried at 120° C. had a moisture content of about 0.2%, meaning that it was substantially anhydrous. Being quite different from the results from the powder x-ray diffraction analyses of the crystalline cyclotetrasaccharide, penta- or hexa-hydrate, and the crystalline cyclotetrasaccharide, monohydrate, before drying in vacuo, the powder x-ray analysis of the above cyclotetrasaccharide, dried in vacuo at 40° C. and 120° C., gave characteristic diffraction spectra having main diffraction angles (2θ) of 10.8°, 14.7°, 15.0°, 15.7°, and 21.5° in FIG. 30 for 40° C. and FIG. 31 for 120° C. Although there found difference in peak levels between the two diffraction spectra, they had substantially the same peak diffraction angles and they were crystallographically judged to be substantially the same crystalline monohydrate. The fact that the base lines of the diffraction spectra exhibited a mountain-like pattern and the crystallinity of the crystalline monohydrate was lower than those of crystalline cyclotetrasaccharide, penta- or hexa-hydrate, and crystalline cyclotetrasaccharide, monohydrate, before drying in vacuo. This revealed the existence of an amorphous cyclotetrasaccharide. Based on this, the cyclotetrasaccharide powder with a moisture content of about 4.2%, obtained by drying in vacuo at 40° C., was estimated to be a mixture powder of an amorphous cyclotetrasaccharide with such a moisture content and anhydrous crystalline cyclotetrasaccharide. These data revealed that crystalline cyclotetrasaccharide, penta- or hexa-hydrate, was converted into those in an anhydrous amorphous- and an anhydrous crystalline-forms when dried in vacuo. The thermogravimetric analysis of anhydrous crystalline cyclotetrasaccharide with a moisture content of 0.2%, which was conducted similarly as in Experiment 20, observed only the weight reduction as shown in FIG. 32, deemed to be induced by the heat decomposition at a temperature of about 270° C. or higher.

Experiment 23

Saturation Concentration of Cyclotetrasaccharide in Water

To study the saturation concentration of cyclotetrasaccharide in water at 10–90° C., 10 ml of water was placed in a glass vessel with a seal cap, and then mixed with cyclotetrasaccharide, penta- or hexa-hydrate, obtained by the method in Experiment 20, in an excessive amount over a level of complete dissolution at respective temperatures, cap-sealed, and stirred for two days while keeping at respective temperatures of 10–90° C. until reaching saturation. The resulting each saturated solution of cyclotetrasaccharide was membrane filtered to remove undissolved cyclotetrasaccharide, and each filtrate was then examined for moisture content by the drying loss method to determine a saturation concentration of cyclotetrasaccharide at respective temperatures. The results are in Table 23.

TABLE 23

| Temperature (° C.) | Saturation concentration (%) |
|---|---|
| 10 | 30.3 |
| 30 | 34.2 |
| 50 | 42.6 |
| 70 | 53.0 |
| 90 | 70.5 |

Experiment 24

Thermostability

A crystalline cyclotetrasaccharide, penta- or hexa-hydrate, obtained by the method in Experiment 20, was dissolved in water into a 10% (w/v) aqueous cyclotetrasaccharide solution, and eight milliliter aliquots of which were placed in glass test tubes, followed by sealing and then heating the test tubes at 120° C. for 30 to 90 min. After the heating, the aqueous solutions were cooled under atmospheric conditions and measured for coloration degree and determined for purity on HPLC. The coloration degree of each solution was evaluated based on the absorbance in a cell with a 1-cm light pass at a wavelength of 480 nm. The results are in Table 24.

TABLE 24

| Heating time (min) | Coloration degree ($A_{480\ nm}$) | Purity (%) |
|---|---|---|
| 0 | 0.00 | 100 |
| 30 | 0.00 | 100 |

TABLE 24-continued

| Heating time (min) | Coloration degree ($A_{480\,nm}$) | Purity (%) |
|---|---|---|
| 60 | 0.00 | 100 |
| 90 | 0.00 | 100 |

As evident from the results in Table 24, it was revealed that cyclotetrasaccharide is a thermostable saccharide because an aqueous cyclotetrasaccharide solution was not colored, and the purity of the saccharide composition in the solution was not lowered even when heated at a high temperature of 120° C.

Experiment 25 pH Stability

A crystalline cyclotetrasaccharide, penta- or hexa-hydrate, obtained by the method in Experiment 20, was dissolved in 20 mM buffers with different pHs into 4% (w/v) cyclotetrasaccharide solutions with pHs of 2 to 10. Eight milliliters of each solution was placed in a glass test tube, followed by sealing and then heating the test tube at 100° C. for 24 hours. After the heating, each solution was cooled and measured for coloration degree and determined for purity on HPLC. The coloration degree was evaluated based on the absorbance in a cell with a 1-cm light pass at a wavelength of 480 nm. The results are in Table 25.

TABLE 25

| pH (type of buffer) | Coloration degree ($A_{480\,nm}$) | Purity (%) |
|---|---|---|
| 2.0 (Acetate buffer) | 0.00 | 93 |
| 3.0 (Acetate buffer) | 0.00 | 100 |
| 4.0 (Acetate buffer) | 0.00 | 100 |
| 5.0 (Acetate buffer) | 0.00 | 100 |
| 6.0 (Tris-HCl buffer) | 0.00 | 100 |
| 7.0 (Tris-HCl buffer) | 0.00 | 100 |
| 8.0 (Tris-HCl buffer) | 0.00 | 100 |
| 9.0 (Ammonium buffer) | 0.00 | 100 |
| 10.0 (Ammonium buffer) | 0.00 | 100 |

As evident from the results in Table 25, a cyclotetrasaccharide aqueous solution was not colored even when heated at 100° C. for 24 hours in a wide pH range from 2 to 10, and the purity of the saccharide composition in each solution was not lowered at all in a pH range from 3 to 10, even though the purity was slightly lowered at pH 2. These facts revealed that cyclotetrasaccharide is highly stable in a relatively wide pH range, i.e., an acid pH range from 3 to 5, a neutral pH range from 6 to 8, and an alkaline pH range from 9 to 10.

Experiment 26

Amino Carbonyl Reaction

A crystalline cyclotetrasaccharide, penta- or hexa-hydrate, obtained by the method in Experiment 20, was dissolved in water, and then admixed with a commercialized special grade glycine and phosphate buffer, and the resulting mixture was then adjusted to pH 7.0 with 50 mM phosphate buffer to obtain a 10% (w/v) cyclotetrasaccharide solution containing 1% (w/v) glycine. Four milliliter aliquots of the resulting solution were placed in glass test tubes, sealed, and heated at 120° C. for 30 to 90 min. After allowing to stand for cooling at ambient temperature, each of the resulting solutions was measured for coloration degree to examine their amino carbonyl reactivity. The coloration degree was evaluated based on the absorbance in a cell with 1-cm light pass at a wavelength of 480 nm. The results are in Table 26.

TABLE 26

| Heating time (min) | Coloration degree ($A_{480\,nm}$) |
|---|---|
| 0 | 0.00 |
| 30 | 0.00 |
| 60 | 0.00 |
| 90 | 0.00 |

As evident from the results in Table 26, cyclotetrasaccharide was not colored even when heated in the presence of glycine, meaning that the saccharide does not induce browning with glycine, i.e., cyclotetrasaccharide is a stable saccharide which does not induce the amino carbonyl reaction, also known as the Maillard reaction.

Experiment 27

Amino Carbonyl Reaction

A crystalline cyclotetrasaccharide, penta- or hexa-hydrate, obtained by the method in Experiment 20, and a polypeptone commercialized by Nihonseiyaku K.K., Tokyo, Japan, were dissolved in deionized water to obtain a 10% (w/v) cyclotetrasaccharide solution containing 5% (w/v) polypeptone. Four milliliter aliquots of the resulting solution were placed in glass test tubes, sealed, and heated at 100° C. for 30 to 90 min. After allowing to stand for cooling at ambient temperature, each of the resulting solution was measured for coloration degree to examine their amino carbonyl reactivity. In parallel, as a control, a solution with only polypeptone was provided and treated similarly as above. The coloration degree was evaluated based on the level of the absorbance, which had been measured in a cell with 1-cm light pass at a wavelength of 480 nm, minused that of the control. The results are in Table 27.

TABLE 27

| Heating time (min) | Coloration degree ($A_{480\,nm}$) |
|---|---|
| 0 | 0.00 |
| 30 | 0.00 |
| 60 | 0.00 |
| 90 | 0.00 |

As evident from the results in Table 27, it was revealed that cyclotetrasaccharide did not induce browning with polypeptone when heated in the presence of polypeptone, i.e., the saccharide is a stable saccharide which substantially does not induce the amino carbonyl reaction.

Experiment 28

Inclusion Action

A crystalline cyclotetrasaccharide, penta- or hexa-hydrate, obtained by the method in Experiment 20, was dissolved in deionized water into a 20% (w/v) aqueous cyclotetrasaccharide solution. To 100 g aliquots of the aqueous solution was added 2 g of methanol, 3 g of ethanol, or 4.6 g acetic acid to be included by the cyclotetrasaccharide. Thereafter, each of the resulting solutions was filtered to remove non-inclusion products, and the filtrates were dried in vacuo. As a control, similar inclusion products were prepared by using "ISOELITE™ P", a branched cyclodextrin commercialized by Maruha K.K., Tokyo, Japan, which were known to have inclusion ability.

To measure the amount of the inclusion products in the resulting lyophilized powders, one gram of each of the powders was dissolved in five milliliters of water and extracted after admixing with five milliliters of diethylether. The extraction was repeated, and the resulting extracts were quantified on gas chromatography. The results are in Table 28.

TABLE 28

| Inclusion product | Inclusion amount (mg/g lyophilized powder) | |
|---|---|---|
| | Cyclotetrasaccharide | ISOELITE P (control) |
| Methanol | 6.71 | 2.92 |
| Ethanol | 17.26 | 8.92 |
| Acetic acid | 67.74 | 30.57 |

As evident from the results in Table 28, it was revealed that cyclotetrasaccharide has an inclusion ability of about 2-folds higher than that of the branched cyclodextrin by weight.

Experiment 29

Sweetening Power

A crystalline cyclotetrasaccharide, penta- or hexa-hydrate, obtained by the method in Experiment 20, was dissolved in deionized water into a 10% (w/v) aqueous cyclotetrasaccharide solution for a standard solution. Varying the concentration of sucrose, e.g., a commercialized granulated sugar, a sensory test was done with five panelists. As a result, the sweetening power of cyclotetrasaccharide was about 20% of that of sucrose.

Experiment 30

Digestion Test

Using a crystalline cyclotetrasaccharide, penta- or hexa-hydrate, obtained by the method in Experiment 20, the digestibility of cyclotetrasaccharide in vitro by salivary amylase, synthetic gastric juice, amylopsin, or intestinal mucosal enzyme was tested in accordance with the method as reported by K. Okada et al. in *JOURNAL OF JAPANESE SOCIETY OF NUTRITION AND FOOD SCIENCE*, Vol. 43, No. 1, pp. 23–29 (1990). As a control, maltitol known as a substantially non-digestive saccharide was used. The results are in Table 29.

TABLE 29

| | Decomposition percentage (%) by digestive enzyme | |
|---|---|---|
| Digestive enzyme | Cyclotetrasaccharide | Maltitol (Control) |
| Salivary amylase | 0.0 | 0.0 |
| Synthetic gastric juice | 0.0 | 0.0 |
| Amylopsin | 0.0 | 0.0 |
| Small intestinal mucosal enzyme | 0.74 | 4.0 |

As evident from the results in Table 29, cyclotetrasaccharide was not completely digested by salivary amylase, synthetic gastric juice, and amylopsin, but slightly digested by intestinal mucosal enzyme in a digestibility level as low as 0.74% that corresponded to ⅕ of that of maltitol as a control. These results confirmed that cyclotetrasaccharide is a quite undigestible saccharide.

Experiment 31

Fermentation Test

Using a crystalline cyclotetrasaccharide, penta- or hexa-hydrate, obtained by the method in Experiment 20, the fermentability of cyclotetrasaccharide using an internal content of rat cecum was tested in accordance with the method by T. Oku in "*Journal of Nutritional Science and Vitaminology*", Vol. 37, pp. 529–544 (1991). The internal content of rat cecum was collected by anesthetizing a Wister male rat with ether, anatomizing the rat, collecting the internal content under anaerobic conditions, and suspending the resultant with 4-fold volumes of a 0.1 M aqueous solution of sodium bicarbonate. The cyclotetrasaccharide was added to the internal content of rat cecum in an amount of about 7% by weight, and the levels of cyclotetrasaccharide remained just after and 12 hours after the addition of the internal content were quantified on gas chromatography. As a result, the levels of cyclotetrasaccharide of the former and the latter were respectively 68.0 mg and 63.0 mg per one gram of the internal content of rat cecum, meaning that 93% of cyclotetrasaccharide remained intact. These data confirmed that cyclotetrasaccharide is a substantially non-fermentable saccharide.

Experiment 32

Assimilation Test

Using a crystalline cyclotetrasaccharide, penta- or hexa-hydrate, obtained by the method in Experiment 20, the assimilability of cyclotetrasaccharide by an internal content of rat cecum was studied in accordance with the method disclosed in "*Intestinal Flora and Dietary Factors*", edited by Tomotari MITSUOKA, published by Japan Scientific Societies Press, Tokyo, Japan, (1984). About $10^7$ CFU (colony forming units) of pre-cultured fresh microorganisms were inoculated into five milliliters of PYF medium with 0.5% cyclotetrasaccharide, and cultured at 37° C. for four days under anaerobic conditions. As a control, glucose was used as an easily assimilable saccharide. The assimilability was judged as negative (−) when the post culture had a pH of 6.0 or higher, and judged as positive (+) when the post culture had a pH of below 6.0. The judgement of assimilability was confirmed by measuring the content of saccharide, which remained in the culture, on the anthrone method to determine the reduction level of saccharide. The results are in Table 30.

TABLE 30

| Strain of intestinal microorganism | Assimilability | |
|---|---|---|
| | Cyclotetrasaccharide | Glucose (control) |
| *Bacteroides vulgatus* JCM 5826 | − | + |
| *Bifidobacterium adolescentis* JCM 1275 | − | + |
| *Clostridium perfringens* JCM 3816 | − | + |
| *Escherichia coli* IFO 3301 | − | + |
| *Eubacterium aerofaciens* ATCC 25986 | − | + |
| *Lactobacillus acidophilus* JCM 1132 | − | + |

As evident from the results in Table 30, it was confirmed that cyclotetrasaccharide was not assimilated by any of the strains tested, but glucose as a control was assimilated by all the strains tested. The data confirmed that cyclotetrasaccharide is a saccharide which is not substantially assimilated by intestinal microorganisms.

Experiment 33

Acute Toxicity Test

The acute toxicity of a crystalline cyclotetrasaccharide, penta- or hexa-hydrate, obtained by the method in Experiment 20, was tested by orally administering to mice. As a result, it was revealed that cyclotetrasaccharide had relatively low toxicity and did not cause the death of mice even when administered at the highest possible dose. Based on this, the $LD_{50}$ of cyclotetrasaccharide was at least 50 g/kg mouse body weight, though the value was so accurate.

Based on the results in Experiments 30 to 33, cyclotetrasaccharide is not substantially assimilated or absorbed by living bodies when orally taken, and it can be expected to be used as a non- or low-caloric edible material in diet sweeteners; fillers for sweeteners with a relatively high sweetening power; viscosity agents, fillers, and bodies for diet food products; and further it can be used as an edible fiber and a food material for substituting fats.

Experiment 34

Comparative Experiment on the Dehydration Degree of Moisture and Pulverization of Dehydrated Product by Non-Reducing Saccharide The non-reducing saccharides used in this experiment were anhydrous crystalline cyclotetrasaccharide; crystalline cyclotetrasaccharide, monohydrate; anhydrous amorphous cyclotetrasaccharide; crystalline cyclotetrasaccharide, penta- or hexa-hydrate; anhydrous crystalline α,α-trehaose, anhydrous amorphous α,α-trehaose; and crystalline α,α-trehaose, dihydrate. The crystalline cyclotetrasaccharide, penta- or hexa-hydrate, was prepared by the method in Experiment 20. The anhydrous crystalline cyclotetrasaccharide; crystalline cyclotetrasaccharide, monohydrate; and anhydrous amorphous cyclotetrasaccharide were respectively prepared by the methods in Examples A-1, A-2, and A-3. As the crystalline α,α-trehalose, dihydrate, a commercially available "TREHA®" commercialized by Hayashibara Shoji Inc., Okayama, Japan, was used. The anhydrous crystalline α,α-trehalose and the anhydrous amorphous α,α-trehalose used in this experiment were prepared from a commercialized crystalline α,α-trehalose, dihydrate, using the methods disclosed in Examples for Reference 1 and 3 in Japanese Patent Kokai No. 170,221/94.

To four parts by weight of a plain yogurt with a moisture content of about 77% was added either of the above saccharides in an amount of 11 to 16 parts by weight. The resultant mixtures were respectively placed in vats, allowed to stand at 25° C. for 24 hours, and macroscopically observed their change on standing. The judgement was conducted in such a manner of sufficiently dehydrating the resulting mixtures to be solidified, subjected to a pulverizer for pulverization, and evaluated as "○", when the solids were easily pulverized; "Δ", when the dehydration of the resulting mixtures was rather insufficient and the pulverization of solids was substantially difficult, though the resulting mixtures were solidified; and "x", when the dehydration of the resulting mixtures was insufficient and could not be pulverized by a pulverizer. The results are in Table 31.

TABLE 31

| Saccharide | Water content (before use) | Weight (part by weight) of saccharide to four parts by weight of plain yogurt with a moisture content of about 77% | | | | | |
|---|---|---|---|---|---|---|---|
| | | 11 | 12 | 13 | 14 | 15 | 16 |
| A | 0.2 | X | Δ | ○ | ○ | ○ | ○ |
| B | 2.7 | X | X | X | Δ | ○ | ○ |
| C | 0.3 | X | Δ | ○ | ○ | ○ | ○ |
| D | 13.0 | X | X | X | X | X | X |
| E | 0.3 | X | X | X | X | Δ | ○ |
| F | 0.8 | X | X | X | X | Δ | ○ |
| G | 9.7 | X | X | X | X | X | X |

Note:
The symbol "A" means anhydrous crystalline cyclotetrasaccharide;
B, crystalline cyclotetrasaccharide, monohydrate;
C, anhydrous amorphous cyclotetrasaccharide;
D, crystalline cyclotetrasaccharide, penta- or hexa-hydrate;
E, anhydrous crystalline α,α-trehalose;
F, anhydrous amorphous α,α-trehalose; and
G, crystalline α,α-trehalose, dihydrate.

As evident from the results in Table 31, it was revealed that anhydrous crystalline cyclotetrasaccharide; crystalline cyclotetrasaccharide, monohydrate; and anhydrous amorphous cyclotetrasaccharide solidified the plain yogurt in a lesser amount than those required in anhydrous crystalline α,α-trehalose and anhydrous amorphous α,α-trehalose; and facilitated the pulverization of the solidified yogurts. The resulting powders had satisfactory properties. Based on these, anhydrous crystalline cyclotetrasaccharide; crystalline cyclotetrasadcharide, monohydrate; and anhydrous amorphous cyclotetrasaccharide, which are the cyclotetrasaccharides with dehydrating ability, are suitably used as dehydrating agents, particularly, anhydrous crystalline cyclotetrasaccharide and anhydrous amorphous cyclotetrasaccharide have a superior dehydrating ability.

Experiment 35

Dehydrating Action by Cyclotetrasaccharide with Dehydrating Ability

Anhydrous crystalline cyclotetrasaccharide; crystalline cyclotetrasaccharide, monohydrate; anhydrous amorphous cyclotetrasaccharide; and crystalline cyclotetrasaccharide, penta- or hexa-hydrate were experimented in detail on their dehydrating actions, particularly, moisture absorption abilities against saccharides and changes on standing. As a control, anhydrous crystalline α,α-trehalose, anhydrous amorphous α,α-trehalose, and crystalline α,α-trehalose, dihydrate, were used as saccharides. The experiments were as follows: Cyclotetrasaccharide and α,α-trehalose preparations, prepared by the method in Experiment 34, were respectively sieved into a powder with a granular size of about 100–150 μm. One gram of each of the resulting powders was placed in a plastic petri dish, 5 cm in diameter, placed in a desiccator controlled at a relative humidity of 60% or 75%, and allowed to stand at 25° C. for a week while sampling the saccharides at a prescribed time interval for quantifying the moisture content (%) by the Karl Fisher method. The results are in Table 32.

TABLE 32

| Saccharide | Relative humidity (%) when treated | Days after treatment | | | | |
|---|---|---|---|---|---|---|
| | | 0 | 1 | 2 | 3 | 7 |
| A | 60 | 0.2 | 10.2 | 10.3 | 10.3 | 10.4 |
| | 75 | 0.2 | 13.9 | 14.4 | 14.4 | 14.3 |

TABLE 32-continued

| Saccharide | Relative humidity (%) when treated | Days after treatment | | | | |
|---|---|---|---|---|---|---|
| | | 0 | 1 | 2 | 3 | 7 |
| B | 60 | 2.7 | 2.7 | 2.8 | 2.8 | 2.9 |
| | 75 | 2.7 | 14.0 | 14.0 | 14.1 | 14.1 |
| C | 60 | 0.3 | 13.7 | 13.8 | 13.9 | 14.1 |
| | 75 | 0.3 | 14.2 | 13.6 | 13.7 | 13.7 |
| D | 60 | 13.0 | 13.1 | 13.1 | 13.1 | 13.2 |
| | 75 | 13.0 | 13.1 | 13.1 | 13.1 | 13.1 |
| E | 60 | — | — | — | — | — |
| | 75 | 0.3 | 9.7 | 9.6 | 9.8 | 9.8 |
| F | 60 | — | — | — | — | — |
| | 75 | 0.8 | 9.8 | 9.7 | 9.8 | 9.7 |
| G | 60 | — | — | — | — | — |
| | 75 | 9.7 | 9.7 | 9.7 | 9.8 | 9.8 |

Note:
The symbol "A" means anhydrous crystalline cyclotetrasaccharide;
B, crystalline cyclotetrasaccharide, monohydrate;
C, anhydrous amorphous cyclotetrasaccharide;
D, crystalline cyclotetrasaccharide, penta- or hexa-hydrate;
E, anhydrous crystalline α,α-trehalose;
F, anhydrous amorphous α,α-trehalose; and
G, crystalline α,α-trehalose, dihydrate.
The symbol "—" means "not tested".

As evident from the results in Table 32, both crystalline cyclotetrasaccharide, monohydrate; and crystalline cyclotetrasaccharide, penta- or hexa-hydrate, did not substantially absorb moisture even after 1-week standing at a relatively humidity of 60%, while anhydrous crystalline cyclotetrasaccharide and anhydrous amorphous cyclotetrasaccharide reached almost their saturated moisture absorption levels on day 1. The moisture absorption level of anhydrous crystalline cyclotetrasaccharide is about 10% of its weight, while that of anhydrous amorphous cyclotetrasaccharide is about 14% of its weight. Powder X-ray diffraction analysis of each saccharide after 1-week standing revealed that they showed the same predominant diffraction angles as those of them before standing tests and did not change in their crystalline forms. It was revealed that the saccharides absorbed moisture at a relative humidity of 60% or lower, but they did not contain water as a crystal water.

When allowed to stand at a relative humidity of 75%, anhydrous crystalline cyclotetrasaccharide, crystalline cyclotetrasaccharide, monohydrate, and anhydrous amorphous cyclotetrasaccharide reached almost their saturated moisture absorption levels after 1-day standing, similarly as in anhydrous crystalline α,α-trehalose and anhydrous amorphous α,α-trehalose. In this case, the moisture absorption levels of these cyclotetrasaccharides were about 14% of each of their weights, while that of α,α-trehalose was not higher than 10% of its weight, revealing that the former is superior to the latter. All the saccharides tested kept their powder forms and did not become sticky or flowing. Powder X-ray diffraction analysis of anhydrous crystalline cyclotetrasaccharide, crystalline cyclotetrasaccharide, monohydrate; and anhydrous amorphous cyclotetrasaccharide, penta- or hepta-hydrate, after 1-week standing revealed that these saccharides showed a different predominant diffraction pattern from those of them before standing tests, which corresponded to the diffraction pattern of crystalline cyclotetrasaccharide, penta- or hexa-hydrate. Based on the results, it was revealed that anhydrous cyclotetrasaccharides are converted into crystalline cyclotetrasaccharide, penta- or hexa-hydrate, after incorporating water as a crystal water at a relative humidity of at least 75%.

Thus, it was concluded that the cyclotetrasaccharide with an effective dehydrating ability according to the present invention can be advantageously used as a strong dehydrating agent for food products, pharmaceuticals, cosmetics, and their materials and processing intermediates.

Experiment 36

Comparison of the Effect of Anhydrous Crystalline Cyclotetrasaccharide and Crystalline Cyclotetrasaccharide, Penta- or Hexa-Hydrate, on Bacterial Contamination of Gelatinized Starch Four parts by weight of a rice flour were dissolved in six parts by weight of water, and the mixture was poured into a container surrounded with woods whose inner surface was covered with a wet cloth, and steamed at 105° C. for 10 min to obtain a gelatinized starch. To the resulting gelatinized starch was added six parts by weight of either crystalline cyclotetrasaccharide, penta- or hexa-hydrate, prepared by the method in Experiment 20, or anhydrous crystalline cyclotetrasaccharide prepared by the method in Example A-1. The mixture was mixed with a mixer and further mixed to homogeneity with two parts by weight of a starch hydrolyzate, shaped, and roughly dried for two hours, while blowing 40° C. hot air to the contents, to obtain "gyuhi" (a rice paste with sugar).

After allowed to stand at ambient temperature of 25° C. under open conditions, there were found colonies of *Aspergillus niger* in gyuhi prepared with crystalline cyclotetrasaccharide, penta- or hexa-hydrate, at 15 days on standing, but found no bacterial contamination in gyuhi with anhydrous crystalline cyclotetrasaccharide even at 30 days on standing.

Gyuhi, prepared with anhydrous cyclotetrasaccharide, at 30 days on standing was cut and macroscopically observed its cross section, revealing that the surface of the product slightly solidified and had crystallized cyclotetrasaccharide but the internal texture kept its semi-transparency, adequate gloss and viscosity similarly as in the product just after processed. Upon X-ray diffraction pattern of the crystal on the surface of the product revealed that anhydrous crystalline cyclotetrasaccharide was converted into crystalline cyclotetrasaccharide, penta- or hexa-hydrate.

Based on the results, it was concluded that the cyclotetrasaccharide with dehydrating ability acts as a dehydrating agent for, prevents bacterial contamination of, and inhibits the retrogradation of gelatinized starch. These characteristics can be advantageously used in products with gelatinized starch such as a gyuhi or flour paste.

The following Examples A explain the cyclotetrasaccharide with dehydrating ability used in the present invention, and Examples B explain the uses of the saccharide in detail:

EXAMPLE A-1

Process for Producing Anhydrous Crystalline Cyclotetrasaccharide

A microorganism of the species *Bacillus globisporus* C11 strain, FERM BP-7144, was cultured by a fermentor for 48 hours in accordance with the method in Experiment 6. After completion of the culture, the resulting culture was filtered with an SF membrane to remove cells and to collect about 18 L of a culture supernatant. Then the culture supernatant was concentrated with a UF membrane to collect about one liter of a concentrated enzyme solution containing 9.0 units/ml of α-isomaltosylglucosaccharide-forming enzyme and 30.2 units/ml of α-isomaltosyl-transferring enzyme. A tapioca starch was prepared into an about 25% starch suspension which was then admixed with 0.2% per gram starch, d.s.b., of "NEO-SPITASE", an α-amylase commercialized by Nagase Biochemicals, Ltd., Kyoto, Japan, and enzymatically reacted at 85° C. to 90° C. for about 20 min. Thereafter, the reaction mixture was autoclaved at 120° C. for 20 min and then promptly cooled to about 35° C. to obtain a liquefied solution with a DE of about four. To the liquefied solution was added 0.25 ml per gram starch, d.s.b., of the above concentrated enzyme solution, containing α-isomaltosylglucosaccharide-forming enzyme and α-isomaltosyl-transferring enzyme, and further added 10 units/g starch, d.s.b., of a CGTase commercialized by Hayashibara Biochemical Laboratories, Inc., Okayama, Japan, followed by the enzymatic reaction at pH 6.0 and 35° C. for 48 hours. The reaction mixture was heated to and kept at 95° C. for 30 min and then adjusted to pH 5.0 and 50° C. and admixed with 300 units/g starch, d.s.b., of "TRANSGLUCOSIDASE L AMANO™", an α-glucosidase commercialized by Amano Pharmaceutical Co., Ltd., Aichi, Japan, followed by an enzymatic reaction for 24 hours. Further, the reaction mixture was mixed with 30 units/g starch, d.s.b., "GLUCOZYME", a glucoamylase commercialized by Nagase Biochemicals, Ltd., Kyoto, Japan, and then enzymatically reacted for 17 hours. The reaction mixture thus obtained was heated to and kept at 95° C. for 30 min, and then cooled and filtered to obtain a filtrate. The resulting filtrate was in a conventional manner decolored with an activated charcoal, desalted and purified with ion exchangers in H- and OH-forms, and then concentrated to obtain a 60% cyclotetrasaccharide syrup in a yield of about 90% to the material starch, d.s.b. According to Experiment 19, the syrup containing cyclotetrasaccharide was subjected to a column packed with 225 L of "AMBERLITE CR-1310 (Na-form)", a strong-acid cation-exchange resin commercialized by Japan Organo Co., Ltd., Tokyo, Japan, and chromatographed at a flow rate of about 45 L/min while keeping the inner column temperature at 60° C. While the saccharide composition of the eluate was monitoring on HPLC described in Experiment 1, fractions rich in cyclotetrasaccharide were collected, pooled, and purified to obtain a high cyclotetrasaccharide content solution in a yield of about 21% to the material starch, d.s.b. The solution contained about 98% cyclotetrasaccharide, d.s.b. After concentrated into an about 90% solution, the resulting concentrate was placed in a crystallizer, admixed with two percent of anhydrous crystalline cyclotetrasaccharide as a seed, and dried in vacuo while keeping at 120° C. for 16 hours to obtain anhydrous crystalline cyclotetrasaccharide with a moisture content of about 0.2%. Since the product has a strong dehydrating ability, it can be advantageously used in dehydrating methods for food products, chemical products, pharmaceuticals, and their materials and processing intermediates.

EXAMPLE A-2

Process for Producing Crystalline Cyclotetrasaccharide, Monohydrate

A potato starch was prepared into an about 20% starch suspension, admixed with calcium carbonate to give a final concentration of 0.1%, adjusted to pH 6.5, further admixed with 0.3% per gram starch, d.s.b., of "TERMAMYL 60L", an α-amylase commercialized by Novo Industri A/S, Copenhagen, Denmark, and then enzymatically reacted at 95° C. for about 15 min. Thereafter, the mixture was autoclaved at 120° C. for 20 min and then promptly cooled to about 35° C. to obtain a liquefied solution with a DE of about four. To the liquefied solution were added 0.25 ml per gram starch, d.s.b., of a concentrated enzyme solution containing α-isomaltosylglucosaccharide-forming enzyme and α-isomaltosyl-transferring enzyme, and 10 units/g starch, d.s.b., of a CGTase commercialized by Hayashibara Biochemical Laboratories Inc., Okayama, Japan, followed by the enzymatic reaction at pH 6.0 and 35° C. for 48 hours. The reaction mixture was heated to and kept at 95° C. for 30 min and then adjusted to pH 5.0 and 50° C., followed by the enzymatic reaction for 24 hours after the addition of 300 units/g solid of "TRANSGLUCOSIDASE L AMANO™", an α-glucosidase commercialized by Amano Pharmaceutical Co., Ltd., Aichi, Japan, and then the enzymatic reaction for 17 hours after the addition of 30 units/g solid of "GLUCOZYME", a glucoamylase commercialized by Nagase Biochemicals, Ltd., Kyoto, Japan. The resulting reaction mixture was heated to and kept at 95° C. for 30 min, and then cooled and filtered. The filtrate thus obtained was in a conventional manner decolored with an activated charcoal, desalted, and purified with ion exchangers in H- and OH-forms, and then concentrated to obtain a 60% cyclotetrasaccharide syrup in a yield of about 90% to the material starch, d.s.b. According to the method in Example A-1, the syrup was chromatographed, followed by collecting fractions with a purity of cyclotetrasaccharide of at least 98%. Then, according to the method in Experiment 20, the fractions were pooled and concentrated by an evaporator into a concentrate having a solid concentration of about 50%. Five kilograms of the concentrate was placed in a cylindrical plastic container and cooled from 65° C. to 20° C. over about 20 hours under gentle stirring conditions to effect crystallization, followed by obtaining a powdery crystalline cyclotetrasaccharide, penta- or hexa-hydrate. The powder was placed in a glass container which was then kept in an oil bath, preheated to 140° C., for 30 min. The dried product was pulverized by a pulverizer to obtain a powdery crystalline cyclotetrasaccharide, monohydrate, with a moisture content of about 7%. Since the product has a strong dehydrating ability, it can be advantageously used in dehydrating methods for food products, chemical products, pharmaceuticals, and their materials and processing intermediates.

EXAMPLE A-3

Process for Producing Anhydrous Amorphous Cyclotetrasaccharide

Figure 33:
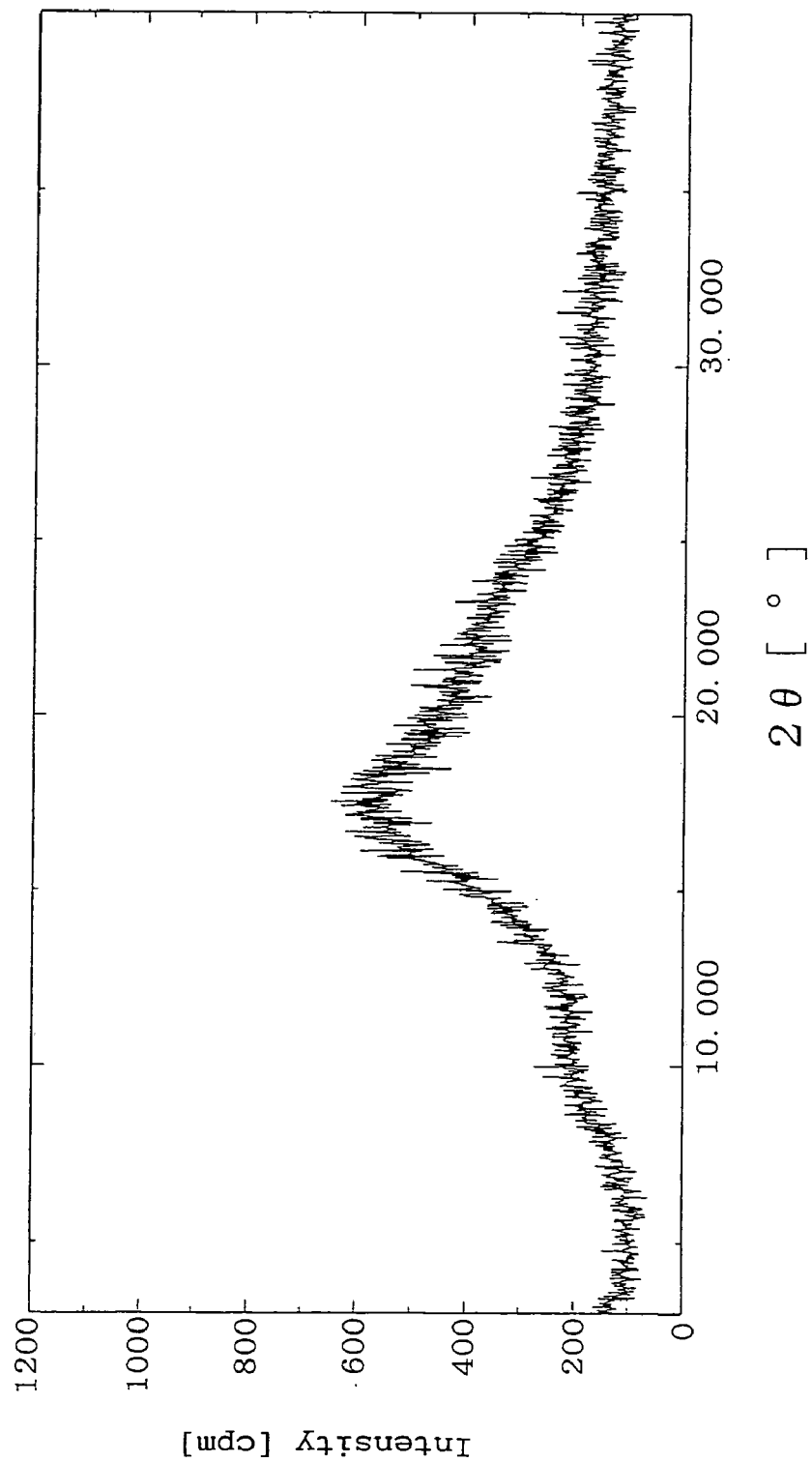
FIG. 33 is an x-ray diffraction spectrum for a powder of anhydrous crystalline cyclotetrasaccharide, obtained by lyophilizing and drying in vacuo an aqueous cyclotetrasaccharide solution.

Fractions containing cyclotetrasaccharide with a purity of at least 98%, obtained according to the method in Example A-1, were in a usual manner desalted, decolored, and filtered to obtain a concentrate having a solid concentration of 50%. The concentrate thus obtained was promptly freezed at −80° C., lyophilized, and further dried in vacuo at 80° C. for three hours. The resulting dried product was pulverized by a pulverizer to obtain a powdery anhydrous amorphous cyclotetrasaccharide with a moisture content of about 0.3%. FIG. 33 is an X-ray diffraction pattern of the powder. Since the product has a strong dehydrating ability, it can be advantageously used in dehydrating methods for food products, chemical products, pharmaceuticals, and their materials and processing intermediates.

EXAMPLE A-4

Process for Producing Anhydrous Crystalline Tetrasaccharide from Panose

About 100 L of an aqueous solution of panose, produced from starch and commercialized by Hayashibara Biochemical Laboratories Inc., Okayama, Japan, was adjusted to give a concentration of 4% (w/v), pH 6.0, and to 30° C., admixed with two units/g panose, d.s.b., of a purified α-isomaltosyl-transferring enzyme obtained by the method in Experiment 7, and enzymatically reacted for 48 hours. Thereafter, the reaction mixture was heated at 100° C. for 10 min to inactivate the remaining enzyme and sampled for analyzing the percentage of cyclotetrasaccharide in the saccharide composition on HPLC, and revealed to be about 44%. The reaction mixture after the heat treatment was adjusted to pH 5.0 and 45° C. and subjected to an enzymatic reaction for 24 hours after the addition of 1,500 units/g solid of "TRANS-GLUCOSIDASE L AMANO™", an α-glucosidase commercialized by Amano Pharmaceutical Co., Ltd., Aichi, Japan, and 75 units/g solid of "GLUCOZYME", a glucoamylase commercialized by Nagase Biochemicals, Ltd., Kyoto, Japan, to hydrolyze the remaining reducing oligosaccharides, etc. Thereafter, the resulting mixture was adjusted to pH 5.8 with sodium hydroxide, incubated at 90° C. for one hour to inactivate the remaining enzymes, and filtered to remove insoluble substances. The filtrate was concentrated to give a solid concentration of about 16% using a reverse osmotic membrane, and the concentrate was in a usual manner decolored, desalted, filtered, and concentrated to obtain about 6.1 kg of a saccharide solution with a solid content of about 3,650 g. The saccharide solution was chromatographed according to the method in Example A-1, followed by collecting fractions with a purity of cyclotetrasaccharide of at least 98%. The fractions were pooled and in a usual manner decolored, desalted, filtered, and concentrated to obtain about 3 kg of a saccharide solution with a solid content of about 1,000 g. HPLC analysis for saccharide composition of the saccharide solution revealed that the solution contained cyclotetrasaccharide with a purity of about 99.2%. The cyclotetrasaccharide solution thus obtained was concentrated by an evaporator into a concentrate having a solid concentration of about 50%. About two kilograms of the concentrate was placed in a cylindrical plastic container, and cooled from 65° C. to 20° C. over about 20 hours under gently rotatory conditions to effect crystallization, followed by drying the formed crystal to obtain crystalline cyclotetrasaccharide, penta- or hexa-hydrate. The crystal thus obtained was further dried in vacuo at 120° C. for 16 hours into anhydrous crystalline cyclotetrasaccharide with a moisture content of about 0.2%. Since the product has a strong dehydrating ability, it can be advantageously used in dehydrating methods for food products, chemical products, pharmaceuticals, and their materials and processing intermediates.

EXAMPLE B-1

Dehydrating Agent

Fifteen grams aliquots of a powdery anhydrous crystalline cyclotetrasaccharide, obtained by the method in Example A-1, were respectively injected into a moisture permeable small paper bag to obtain a dehydrating agent. The product is advantageously used as an agent for dehydrating the inner atmosphere of moisture-proof containers which house seasoned sea layers, cookies, etc., and also can be arbitrarily used in combination with a deoxidizer(s) in dried or oily food products to stably store them.

EXAMPLE B-2

Sugar with Dehydrating Agent

To 50 parts by weight of sugar was added one part by weight of a hydrous crystalline cyclotetrasaccharide powder obtained by the method in Example A-4, followed by mixing with a high-speed rotary mixer. One kilogram aliquots of the resulting mixture were respectively placed in a polyethylene bag, followed by deaerating the gas space in the bag, heat sealing the opening of the bag to obtain a sugar composition with a dehydrating agent. In the product, the dehydrating agent absorbs moisture on the surface of microcrystalline sugars, and this is credited with preventing them from adhering and solidifying, and with ensuring its stable shelf-life. The product can be used as a seasoning in preparing cooked/processed foods.

EXAMPLE B-3

Salt with Dehydrating Agent

To 100 parts by weight of salt was added one part by weight of a hydrous crystalline cyclotetrasaccharide powder obtained by the method in Example A-1, followed by mixing on a high-speed rotary mixer. One kilogram aliquots of the resulting mixture were respectively placed in a polyethylene bag, followed by deaerating the gas spaces of the bags and heat sealing their openings to obtain a salt composition with a dehydrating agent. In the product, the dehydrating agent absorbs moisture on the surface of microcrystalline salts, and this is credited with preventing them from adhering and solidifying and with ensuring its stable shelf-life. The product can be used as a seasoning in preparing cooked/processed foods.

EXAMPLE B-4

"Soboro-Gyuhi" (a Rice Paste Like Soboro "a Dried Fish Meat Flake")

Four parts by weight of a rice flour were dissolved in six parts by weight of water, poured into a container surrounded with woods whose inner surface was covered with a wet cloth, steamed at 100° C. for 20 min, kneaded with one part by weight of sugar and six parts by weight of an anhydrous crystalline cyclotetrasaccharide powder obtained by the method in Example A-1, and sufficiently mixed with two parts by weight of a hydrolyzed starch syrup. The mixture was shaped, allowed to stand at room temperature for 16 hours to convert the saccharide into crystalline cyclotetrasaccharide, penta- or hexa-hydrate, lightly rolled to make cracks on the surface of the resultant product to obtain the captioned product. The product has a satisfactory flavor and taste, is substantially free of bacterial contamination, and keeps its high quality for a relatively long period of time.

EXAMPLE B-5

Confectionery of Sweet Potato

A sweet potato was sliced into pieces of about 1-cm in thickness, steamed, cooled, and sprinkled with an anhydrous crystalline cyclotetrasaccharide powder obtained by the method in Example A-3 to convert the saccharide into crystalline cyclotetrasaccharide, penta- or hexa-hydrate. Thus, a confectionery of sweet potato, which the converted saccharide adhered unto the surface, was produced, and it had a satisfactory stability, flavor, and taste.

EXAMPLE B-6

Powdered Cream

One part by weight of a fresh cream and three parts by weight of an anhydrous crystalline cyclotetrasaccharide powder, obtained by the method in Example A-1, were mixed and transferred to a vat, and allowed to stand for two days to form a block while converting the saccharide into crystalline cyclotetrasaccharide, penta- or hexa-hydrate. The block was pulverized by a cutter and classified to obtain a powdered cream with a satisfactory flavor and taste. Thus, the product can be used to sweeten coffee and tea and used as a material for processing premixes, frozen desserts, cakes, and candies, as well as a therapeutic nutrition for intubation feedings.

EXAMPLE B-7

Powdered Brandy

Two parts by weight of a brandy were mixed with 10 parts by weight of pullulan and seven parts by weight of an anhydrous crystalline cyclotetrasaccharide powder obtained by the method in Example A-1. The resulting mixture was allowed to stand for two days to form a block while converting the saccharide into crystalline cyclotetrasaccharide, penta- or hexa-hydrate. The block was subjected to a cutter for pulverization and classified to obtain a powdered brandy with a satisfactory flavor and taste, i.e., a powdered flavor with an adequate sweetness and a sufficient flavor of brandy when tasted in your mouth. The product can be used for imparting flavor to tea and advantageously used as a material for confectioneries such as premixes and candies. Also the product can be shaped by a granulator or a tabletting machine into a granule or tablet for use.

EXAMPLE B-8

Powdered Miso

Two parts by weight of akamiso were mixed with four parts by weight of a powdery crystalline cyclotetrasaccharide, monohydrate, obtained by the method in Example A-1. The mixture was poured over a metal plate with a plural semispheric dimples, allowed to stand at ambient temperature overnight to solidify the contents. The solids were removed from the dimples to obtain solid misos, about four grams each, which were then subjected to a pulverizer to obtain the captioned product. The product can be arbitrarily used as a seasoning for instant soups and also used as a solid seasoning and a miso confectionery.

EXAMPLE B-9

Powdered Soy Sauce

While 3.5 parts by weight of an anhydrous crystalline cyclotetrasaccharide, obtained by the method in Example A-3, and 0.02 part by weight of crystalline cyclotetrasaccharide, penta- or hexa-hydrate, obtained by the method in Experiment 20, were freely-moved over a conveyer, one part by weight of "koikuchi-shoyu" (a pale-colored soy sauce) was sprayed over the mixture. The resulting mixture was transferred to an aging tower and allowed to stand at 30° C. overnight to obtain a powdered soy sauce while converting the saccharide into crystalline cyclotetrasaccharide, penta- or hexa-hydrate. The product can be arbitrarily used as a seasoning for instant soups.

EXAMPLE B-10

Powdered Egg Yolk

Yolks prepared from fresh eggs were sterilized by a plate heating sterilizer at 60 to 64° C., and one part by weight of the resulting liquid of egg yolks was mixed with 3.5 parts by weight of an anhydrous crystalline cyclotetrasaccharide, obtained by the method in Example A-1, and similarly as in Example B-7, the mixture was shaped into a block, followed by pulverizing the block into a powdered egg yolk. The product can be used as a material for confectioneries such as premixes, frozen deserts, and emulsifiers, as well as diets of weaning and therapeutic nutrients such as oral fluid diets and foods for intubation feedings. Also it can be used as a skin-beautifying agent or hair restorer.

EXAMPLE B-11

Powdered Yogurt

One part by weight of a plain yogurt was mixed with 3.6 parts by weight of an anhydrous amorphous cyclotetrasaccharide, obtained by the method in Example A-3 and, similarly as in Example B-7, the mixture was shaped into a block, followed by pulverizing the block into a powdered yogurt. The product can be used as a material for confectioneries such as premixes, frozen deserts, and emulsifiers, as well as diets of weaning and therapeutic nutrients such as oral fluid diets and foods for intubation feedings. Also it can be arbitrarily incorporated into margarines, whipping creams, spreads, cheese cakes, and jellies into yogurt-flavored products. The powdered yogurt in this example can be shaped by a granulator or a tabletting machine into a product with lactic acid bacteria for use as an intestinal controlling agent.

EXAMPLE B-12

Hot Cake Mix

To 200 parts by weight of wheat flour were added 60 parts by weight of a powdered egg yolk obtained by the method in Example B-10, 25 parts by weight of butter, 10 parts by weight of sugar, 12 parts by weight of a baking powder, and 0.5 part by weight of salt to obtain a hot cake mix. After dissolving in water or milk, the product can be baked to easily obtain a hot cake with a satisfactory taste and flavor.

EXAMPLE B-13

Powdered Ginseng Extract

A half part by weight of a ginseng extract was mixed with 1.2 parts by weight of an anhydrous crystalline cyclotetrasaccharide obtained by the method in Example A-1 and, similarly as in Example B-7, the mixture was shaped into a block and pulverized into a powdered ginseng extract. The product was subjected to a granulator together with adequate amounts of powders of vitamins $B_1$ and $B_2$ to obtain a vitamin-containing granule of ginseng extract. The product thus obtained can be advantageously used as an agent for recovering healthy conditions from fatigue and for tonic, pickup, or hair restorer.

EXAMPLE B-14

Powdered Propolis Extract

A material propolis was extracted with a 95% (v/v) aqueous ethanol solution in a usual manner, and the remaining residue was washed with a small amount of water. The resulting extract and the water used for washing the residues were pooled into an 80% (v/v) aqueous ethanol solution as a crude propolis extract with a solid content of about 20% (w/w), d.s.b., which was then diluted with water to lower the ethanol concentration to 50% (v/v). The resulting solution was kept at 50° C. for one hour to form an upper layer containing the effective ingredients of propolis and a lower layer containing viscus sediments, and allowed to stand at ambient temperature overnight, followed by separating and collecting the upper layer, i.e., a liquid propolis extract with a satisfactory color tint, flavor, and antimicrobial action in a yield of about 48%, d.s.b., to the crude propolis extract. One part by weight of the purified propolis extract was sprayed and mixed with 10 parts by weight of an anhydrous crystalline cyclotetrasaccharide obtained by the method in Example A-1, and the resulting mixture was dried into a powdered propolis extract with a satisfactory flavor and taste. The product can be used intact as an antiseptic, antioxidant, anti-inflammatory, immunoregulatory agent, or macrophage activating agent; and mixed with other appropriate materials for use in food products, cosmetics, and anti-susceptive diseases which can be treated and/or prevented with the propolis extract.

EXAMPLE B-15

Powdered Extract of Japanese Indigo Plant

Thirty kilograms of terrestrial parts of an indigo plant, an annual plant of the genus *Polygonum*, having a botanical name of *Polygonum tinctorium*, were crushed, extracted with a 90% (v/v) aqueous ethanol solution in a usual manner. The remaining residues were washed with a small amount of water. The resulting extract and the water used for washing the residues were pooled into an aqueous solution as a crude indigo extract which was then diluted with water to lower the ethanol concentration to 50% (v/v). One part by weight of the crude indigo extract was mixed with 12 parts by weight of crystalline cyclotetrasaccharide, monohydrate, obtained by the method in Example A-2. The mixture was transferred to a vat, allowed to stand for two days to form a block while converting the saccharide into crystalline cyclotetrasaccharide, penta- or hexa-hydrate. The resulting block was pulverized by a cutter and classified to obtain a powdered indigo extract. The product has diversified physiological actions such as an antiseptic-, antiviral-, antitumor-, radical entrapping-, apoptosis controlling-, and cytokine regulatory-actions, and can be arbitrarily used as a crude drug to be incorporated into food products, cosmetics, and pharmaceuticals.

EXAMPLE B-16

Powdered Coriander

Terrestrial parts of a coriander (*Coriandrum sativum* L.), a plant of the family Umbelliferae and the genus *Coriandrum*, were washed with water, drained, and cut into small pieces by a blender. The pieces were passed through a 150-mesh sieve using a centrifugal filtration separator, followed by collecting the extract and treated at 121° C. for 10 min to obtain a coriander extract containing 60 mg/ml solids. One part by weight of the extract was mixed with nine parts by weight of anhydrous crystalline cyclotetrasaccharide in Example A-4, and the mixture was transferred to a vat, allowed to stand for two days to form a block while converting the saccharide into crystalline cyclotetrasaccharide, penta- or hexa-hydrate. The resulting block was pulverized by a cutter and classified to obtain a powdered coriander extract. The product has an activity of inhibiting the adhesion of metals such as lead and can be advantageously used intact or in combination with food products or pharmaceuticals.

EXAMPLE B-17

Powdered Royal Jelly

One part by weight of an intact Brazilian royal jelly with a moisture content of 65% (w/w) was mixed with seven parts by weight of anhydrous crystalline cyclotetrasaccharide obtained by the method in Example A-1. The resulting mixture was transferred to a vat and allowed to stand for two days for forming a block while converting the saccharide into crystalline cyclotetrasaccharide, penta- or hexa-hydrate. The block was pulverized by a cutter into a powdered royal jelly which was then classified by passing through a 100-mesh sieve and tabletted by a tabletting machine to obtain tablets, 300 mg each. The product has a strong tonic action and cell activating action and stably retains the royal jelly susceptible to deterioration for a relatively long period of time even at ambient temperature. Since the product has an improved flavor and taste, as well as a mild sweetness and an adequate sour taste, it can be arbitrarily used as a health food for daily use.

EXAMPLE B-18

Solid Preparation for Fluid Food

A composition, consisting of 400 parts by weight of an anhydrous crystalline cyclotetrasaccharide powder obtained by the method in Example A-1, 270 parts by weight of a powdered egg yolk obtained by the method in Example B-7, 209 parts by weight of a skim milk powder, 4.4 parts by weight of sodium chloride, 1.85 parts by weight of potassium chloride, 0.01 part by weight of thiamine, 0.1 part by weight of sodium L-ascorbate, 0.6 part by weight of vitamin E acetate, and 0.04 part by weight of nicotinic acid amid, was prepared. Twenty-five grams aliquots of the composition were injected into moisture-proof laminated small bags which were then heat sealed to obtain a solid preparation for fluid foods.

The product, wherein the moisture content in its inner atmosphere is lowed, has a relatively long shelf-live without a need of cold storage. Also it has a satisfactory dispersibility and solubility in water. In use, one bag of the product is dissolved in about 150–300 ml water into a fluid food and then orally administered to a subject or intubationally administered to the nasal cavity, stomach, intestine, etc.

EXAMPLE B-19

Tablet Preparation for Medical Use

New born hamsters were injected with an antiserum prepared from rabbits by a conventional method to reduce their immunoreaction, subcutaneously transplanted with BALL-1 cells, and bred for three weeks in a usual manner.

Tumor masses formed subcutaneously were extracted, cut into pieces, and suspended in physiological saline. The resulting cell suspension was washed with RPMI 1640 medium (pH 7.2) free of serum, suspended in a fresh preparation of the same medium to give a cell density of about $2\times10^6$ cells/ml, and incubated at 35° C.

After the addition of 200 IU/ml of a partially purified human interferon-α, the cell suspension was incubated for about two hours and then admixed with about 300 HA/ml of sendai virus (HVJ) and incubated for 20 hours to induce human interferon-α. The resulting culture was centrifuged at 4° C. and about 1,000×g, followed by removing sediments. The resulting supernatant was membrane filtered, and the filtrate was in a conventional manner fed to a column immobilized with an anti-interferon-α antibody, followed by removing non-adsorbed fractions. The interferon adsorbed on the antibody was eluted as adsorbed fractions which were then concentrated with a membrane into a 4-ml concentrate, containing about 0.001% (w/v) proteins and a human interferon-α with a specific activity of about $2\times10^8$ IU/mg protein, per hamster.

One kilogram of anhydrous crystalline cyclotetrasaccharide, obtained by the method in Example A-1, was pulverized, passed through a 150-mesh sieve, and mixed to homogeneity with a dilute, which had been prepared by diluting 0.25 ml of the above concentrate having about $1\times10^6$ IU of interferon-α with 100 ml distilled water, while spraying the dilute over the saccharide powder. The resulting mixture was in a usual manner tabletted by a tabletting machine to obtain a 300 mg tablet with 150 IU of interferon-α. The process in this example easily dehydrates solutions of interferon-α only by spraying an anhydrous crystalline cyclotetrasaccharide powder, facilitates homogeneous mixing, and also effectively stabilizes the interferon-α.

Since the product easily dissolves in water, it can be advantageously used as an agent for anti-susceptive diseases, which can be treated and/or prevented with interferon-α, such as an antiviral-, antitumor-, antirheumatic-, and anti-immunopathic-agents in the form of an internal or oral agent. Also the product can be advantageously used as a reagent for examination.

EXAMPLE B-20

Granular Preparation for Medical Use

A stock culture of BALL-1 cell, a human lymphoblastoid cell line, was inoculated into Eagle's minimum essential medium (pH 7.4) supplemented with 20% (v/v), and in a usual manner subjected to an in vitro suspension culture at 37° C. The resulting cells were washed with Eagle's minimum essential medium (pH 7.4) free of serum and suspended in a fresh preparation of the same medium to give a cell density of about $1\times10^7$ cells/ml. HVJ was added to the cell suspension in an amount of about 1,000 HA/ml and incubated at 38° C. for one day to induce tumor necrosis factor-α (TNF-α). The resulting culture was centrifuged at 4° C. and about 1,000×g, and the supernatant was dialyzed for 15 hours against 0.01 M phosphate buffer (pH 7.2) in physiological saline, and membrane filtered. The filtrate was in a usual manner fed to a column of anti-interferon antibody, and the non-adsorbed fractions were subjected to affinity chromatography using a column packed with gels of anti-TNF-α monoclonal antibody to purify the formed TNF-α, followed by concentrating the desired fractions to obtain a concentrate having a protein concentration of about 0.01% (w/v) and TNF-α with a specific activity of about $2\times10^6$ JRU/mg protein in a yield of about $5\times10^4$ JRU per L of the culture after the induction and formation of TNF-α.

A half milliliter of the above TNF-α concentrate with TNF-α activity of about $1\times10^5$ JRU was diluted with 100 ml of distilled water and then mixed to homogeneity with a cyclotetrasaccharide powder, which had been prepared by pulverizing one kilogram of anhydrous crystalline cyclotetrasaccharide obtained by the method in Example A-1, and passing through a 150-mesh sieve, while spraying the dilute over the powder. The resulting mixture was then in a usual manner granulated by a granulator into a TNF-α preparation in the form of a granule, containing about 100 JRU/g of TNF-α. The process in this example easily dehydrates solutions of TNF-α only by spraying an anhydrous crystalline cyclotetrasaccharide powder, facilitates homogeneous mixing, and also effectively stabilizes the TNF-α.

Since the product easily dissolves in water, it can be advantageously used as an agent for anti-susceptive diseases, which can be prevented and/or treated with TNF-α, such as an antiviral-, antitumor-, antirheumatic-, and anti-immunopathic-agents in the form of an internal or oral agent. Also the product can be advantageously used as a reagent for examination.

EXAMPLE B-21

Ointment for Traumatherapy

Four hundred parts by weight of anhydrous crystalline cyclotetrasaccharide obtained by the method in Example A-1 were admixed with three parts by weigh of iodine dissolved previously in 50 parts by weight of methanol, and further admixed with 200 parts by weight of a 10% aqueous pullulan solution and 50 parts by weight of crystalline maltose hydrate. The resulting mixture was allowed to stand at ambient temperature overnight to convert the cyclotetrasaccharide into crystalline cyclotetrasaccharide, penta- or hexa-hydrate, to obtain an ointment for traumatherapy with an adequate adhesiveness and extendibility.

By applying to affected skin parts directly or after pasted on gauzes, oilpapers or the like, the product cures external injuries such as skin ulcers induced by cuts, excoriations, burns, and dermatophytosises (athlete's foot).

POSSIBILITY OF INDUSTRIAL APPLICABILITY

As evident from the above, the present invention relates to a dehydrating agent comprising a non-reducing cyclotetrasaccharide as an effective ingredient, particularly, cyclotetrasaccharide with dehydrating ability can be advantageously used, as the effective ingredient, to reduce the moisture content in the inner atmosphere of moisture-proof containers which house dried food products, etc., and in hydrous products such as food products, cosmetics, pharmaceuticals, industrial chemicals, and their materials and processing intermediates. The method of the present invention, which comprises a step of allowing a cyclotetrasaccharide with dehydrating ability to contact with hydrous matters to substantially reduce their moisture content through the conversion of the cyclotetrasaccharide into crystalline cyclotetrasaccharide, penta- or hexa-hydrate. Since the method does not need severe conditions such as heat drying, it can easily dehydrate the following hydrous matters and facilitates to produce high quality dehydrated products: Examples of the above hydrous matters include food products susceptible to deteriorating flavor and taste, and pharmaceuticals with effective ingredients susceptible to decomposing and lowering their activities. The dehydrated products, which are well prevented from bacterial contamination and which the denaturalization or deterioration such as hydrolysis, rancidity, and browning are inhibited, have a relatively long, stable shelf-life.

The present invention with such outstanding effects and functions is a significant invention that greatly contributes to this art.

The invention claimed is:

1. A method for producing a dehydrated product, which comprises a step of either incorporating, contacting or coexisting a saccharide having the structure of cyclo{6)-α-D-glucopyranosyl-(1 3)-α-D-glucopyransyl-(1 6)-α-D-glucopyranosyl-(1 3)-α-D-glucopyranosyl-(1}, into, with, or in a food product, cosmetic, pharmaceutical, or industrial chemical containing water, wherein said saccharide is in a crystalline anhydrous form, crystalline monohydrous form or anhydrous amorphous form.

2. The method of claim 1, where the saccharide is in an amount of in the range of 0.001–200 parts by weight to one part by weight of the food product, cosmetic, pharmaceutical, or industrial chemical containing water.

* * * * *

```
                        SEQUENCE LISTING

<160> NUMBER OF SEQ ID NOS: 10

<210> SEQ ID NO 1
<211> LENGTH: 9
<212> TYPE: PRT
<213> ORGANISM: Bacillus globisporus

<400> SEQUENCE: 1

Tyr Val Ser Ser Leu Gly Asn Leu Ile
 1               5

<210> SEQ ID NO 2
<211> LENGTH: 10
<212> TYPE: PRT
<213> ORGANISM: Bacillus globisporus

<400> SEQUENCE: 2

Ile Asp Gly Val Tyr His Ala Pro Asn Gly
 1               5                  10

<210> SEQ ID NO 3
<211> LENGTH: 10
<212> TYPE: PRT
<213> ORGANISM: Bacillus globisporus

<400> SEQUENCE: 3

Ile Asp Gly Val Tyr His Ala Pro Tyr Gly
 1               5                  10

<210> SEQ ID NO 4
<211> LENGTH: 8
<212> TYPE: PRT
<213> ORGANISM: Bacillus globisporus

<400> SEQUENCE: 4

Ile Asp Gly Val Tyr His Ala Pro
 1               5

<210> SEQ ID NO 5
<211> LENGTH: 8
<212> TYPE: PRT
<213> ORGANISM: Bacillus globisporus

<400> SEQUENCE: 5

Asp Ala Ser Ala Asn Val Thr Thr
 1               5

<210> SEQ ID NO 6
<211> LENGTH: 8
<212> TYPE: PRT
<213> ORGANISM: Bacillus globisporus

<400> SEQUENCE: 6

Trp Ser Leu Gly Phe Met Asn Phe
 1               5
```

<210> SEQ ID NO 7
<211> LENGTH: 8
<212> TYPE: PRT
<213> ORGANISM: Bacillus globisporus

<400> SEQUENCE: 7

Asn Tyr Thr Asp Ala Trp Met Phe
 1               5

<210> SEQ ID NO 8
<211> LENGTH: 8
<212> TYPE: PRT
<213> ORGANISM: Bacillus globisporus

<400> SEQUENCE: 8

Gly Asn Glu Met Arg Asn Gln Tyr
 1               5

<210> SEQ ID NO 9
<211> LENGTH: 8
<212> TYPE: PRT
<213> ORGANISM: Bacillus globisporus

<400> SEQUENCE: 9

Ile Thr Thr Trp Pro Ile Glu Ser
 1               5

<210> SEQ ID NO 10
<211> LENGTH: 8
<212> TYPE: PRT
<213> ORGANISM: Bacillus globisporus

<400> SEQUENCE: 10

Trp Ala Phe Gly Leu Trp Met Ser
 1               5